United States Patent [19]
Benoit et al.

[11] Patent Number: 5,902,773
[45] Date of Patent: May 11, 1999

[54] PYRAZOLO-(1,5A)-PYRIMIDINES, PROCESS FOR PREPARING THE SAME AND THEIR USE

[75] Inventors: Remy Benoit, Neustadt; Thomas Grote, Göttingen; Herbert Bayer, Mannheim; Bernd Müller, Frankenthal; Klaus Oberdorf, Heidelberg; Hubert Sauter, Mannheim; Eberhard Ammermann, Heppenheim; Gisela Lorenz, Hambach; Siegfried Strathmann, Limburgerhof, all of Germany

[73] Assignee: BASF Aktiengesellschaft, Ludwigshafen, Germany

[21] Appl. No.: 08/945,609

[22] PCT Filed: Apr. 26, 1996

[86] PCT No.: PCT/EP96/01774

§ 371 Date: Oct. 28, 1997

§ 102(e) Date: Oct. 28, 1997

[87] PCT Pub. No.: WO96/35690

PCT Pub. Date: Nov. 14, 1996

[30] Foreign Application Priority Data

May 9, 1995 [DE] Germany ............... 195 16 843
Jan. 20, 1996 [DE] Germany ............... 196 02 072

[51] Int. Cl.$^6$ ............ C07D 487/04; A01N 43/54

[52] U.S. Cl. ............ 504/240; 504/241; 544/253; 544/278; 544/279

[58] Field of Search ............ 504/240, 241; 544/253, 278, 279

[56] References Cited

FOREIGN PATENT DOCUMENTS

| 278 959 | 8/1988 | European Pat. Off. . |
| 254426 | 11/1988 | European Pat. Off. . |
| 398 692 | 11/1990 | European Pat. Off. . |
| 38 25 043 | 2/1989 | Germany . |

*Primary Examiner*—Jose' G. Dees
*Assistant Examiner*—Sabiha N. Qazi
*Attorney, Agent, or Firm*—Keil & Weinkauf

[57] ABSTRACT

Pyrazolo pyrimidines of the formula I

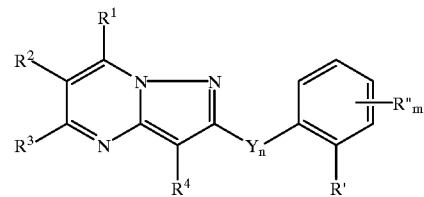

where the indices and the substituents have the meanings defined in the specification, processes for their preparation and their use are described.

11 Claims, No Drawings

PYRAZOLO-(1,5A)-PYRIMIDINES, PROCESS FOR PREPARING THE SAME AND THEIR USE

This application has been filed under 35 USC 371 as a national stage application of PCT/EP96/01774 filed Apr. 26, 1996.

The present invention relates to pyrazolo[1,5a] pyrimidines of the formula I

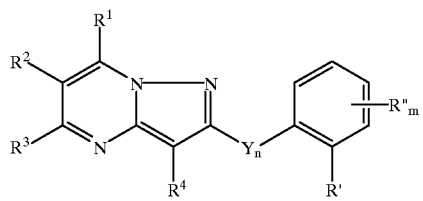

where the indices and the substituents have the following meanings:

n is 0 or 1;

Y is O, S, $NR^a$, $OCH_2^*$, $SCH_2^*$, $NR^aCH_2^*$, $CH_2O^*$, $CH_2S^*$, $CH_2NR^{a*}$, $CH_2CH_2$, $CR^a=R^b$ or $C\equiv C$, the positions identified by * marking the bond to the phenyl ring;

R' is $H_3CO-CO-\bullet.=CHOCH_3$, $H_3CNH-CO-\bullet=CHOCH_3$, $H_3CO-CO-\bullet.=NOCH_3$, $H_3CNH-CO-\bullet.=NOCH_3$, $H_2N-CO-\bullet.=NOCH_3$, $HO-CO-\bullet.=NOCH_3$, $H_3CO-CO-\bullet.=CHCH_3$, $H_3CO-CO-\bullet.=CHCH_2CH_3$, $H_3C-CO-\bullet.=CHOCH_3$, $H_3C-CO-\bullet.=NOCH_3$, $H_3CCH_2-CO-\bullet=NOCH_3$, $\bullet$ being a C atom bonded to the phenyl ring; $N(OCH_3)-CO_2CH_3$, $N(CH_3)-CO_2CH_3$, $N(CH_2CH_3)-CO_2CH_3$, or a group R'.1—$\bullet=NOCH_3$, R'.2-$\bullet=NOCH_3$, R'.3—$\bullet=NOCH_3$ or R'.4—$\bullet=NOCH_3$,

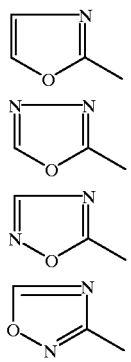

m is 0, 1, 2 or 3, it being possible for radicals R" to be different if m is greater than 1;

R" is cyano, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

$R^1$ and $R^3$ are hydrogen, cyano, nitro, hydroxyl, amino, halogen, alkyl, haloalkyl, alkoxy, haloalkoxy, alkylthio, haloalkylthio, aryl, arylalkyl, aryloxy, arylalkoxy, arylthio, heteroaryl, heteroarylalkyl, heteroaryloxy, heteroarylalkoxy, heteroarylthio, or $NR^cR^d$, $NR^cNR^dR^e$, $CO-R^c$, $CO_2-R^c$, $CO-NR^cR^d$, $O-CO-R^c$, $O-CO_2-R^c$, $O-CO-NR^cR^d$, $NR^c-CO-R^d$, $NR^c-CO_2-R^d$ or $NR^c-CO-NR^dR^e$;

$R^2$ is hydrogen, halogen, alkyl, haloalkyl, alkoxy, haloalkoxy, aryl, aryloxy, heteroaryl, heteroaryloxy, $CO-R^c$, $CO_2-R^c$ or $CR^f=NOR^g$;

$R^4$ is hydrogen, cyano, nitro, nitroso, halogen, alkyl, haloalkyl, alkoxy, haloalkoxy, alkylthio, haloalkylthio, aryl, arylalkyl, aryloxy, arylalkoxy, arylthio, heteroaryl, heteroarylalkyl, heteroaryloxy, heteroarylalkoxy, heteroarylthio, or $NR^cR^d$, $CO-R^c$, $CO_2-R^c$ or $CR^f=NOR^g$;

$R^a$ and $R^b$ are hydrogen, halogen, $C_1$-$C_4$-alkyl or $C_1$-$C_4$-haloalkyl;

$R^c$, $R^d$ and $R^e$ are hydrogen, alkyl, alkenyl, alkynyl, aryl, arylalkyl, heteroaryl or heteroarylalkyl;

$R^f$ is hydrogen, cyano, halogen, unsubst. or subst. alkyl, alkyloxy, alkylthio, alkenyl, alkenyloxy, alkenylthio, alkynyl, alkynyloxy, alkynylthio, cycloalkyl, cycloalkyloxy, cycloalkylthio, heterocyclyl, heterocyclyloxy, heterocyclylthio, aryl, aryloxy, arylthio, heteroaryl, heteroaryloxy or heteroarylthio;

$R^g$ is hydrogen, unsubst. or subst. alkyl, alkenyl, alkynyl, cycloalkyl, heterocyclyl, aryl or heteroaryl, processes for their preparation, compositions containing them and their use for controlling pests and harmful fungi.

In the literature, for example, fungicidally active compounds are disclosed which, instead of the pyrazolo[1,5a] pyrimidine ring, carry a quinolinyl, isoquinolinyl or benzopyrazinyl radical (EP-A 278 595). Corresponding active compounds having pyridyl, pyridazinyl, pyrimidyl, pyrazinyl, triazinyl or tetrazinyl radicals are additionally described (EP-A 398 692, EP-A 254 426).

It is an object of the present invention to provide novel active compounds having an improved spectrum of action.

We have found that this object is achieved by the pyrazolo [1,5a]pyrimidines defined at the beginning. Processes for their preparation, compositions containing them and their use for controlling pests and harmful fungi have additionally been found.

The compounds I are prepared in a similar manner to various methods known per se from the literature. In the preparation, it is in general insignificant whether the group R is synthesized first or whether the pyrazolopyrimidine radical is coupled to Y first. Depending on the stability of the intermediates, it is also possible to carry out the coupling to the pyrazolopyrimidine in the individual stages of the synthesis of R.

Accordingly, for greater clarity in the following reaction equations the pyrazolopyrimidine group or its precursors, if they are not involved in the reaction, are shown in abbreviated form as R*.

In the preparation of the compounds I where $Y_n$ is $OCH_2^*$, $SCH_2^*$ or $NR^aCH_2^*$ [collectively designated as $XCH_2$], a procedure is in general followed in which a benzyl derivative of the formula IIa is reacted in a manner known per se in an inert organic solvent in the presence of a base with a pyrazolopyrimidine of the formula IIIa.

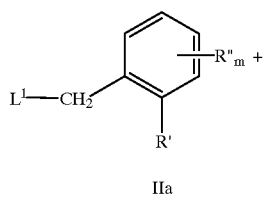

IIa

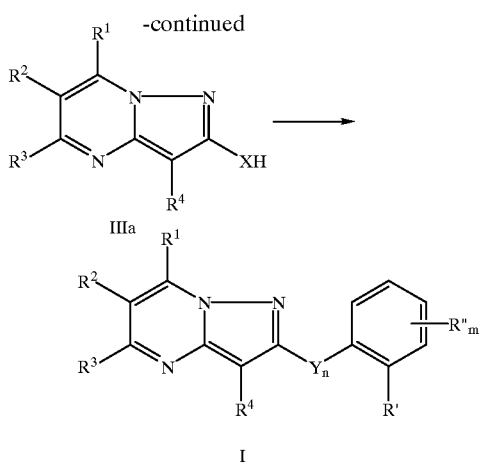

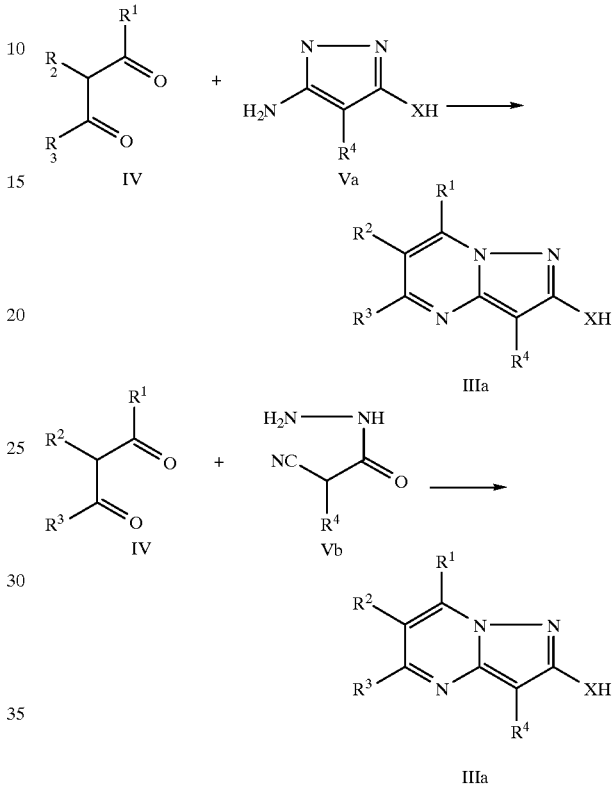

L¹ in the formula IIa is a nucleophilically replaceable leaving group such as halogen (eg. chlorine, bromine or iodine) or a sulfonate (eg. trifluoromethylsulfonate, phenylsulfonate or p-methylphenylsulfonate).

This reaction is customarily carried out at from 0° C. to 120° C., preferably 15° C. to 60° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ethyl, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butyl and also dimethyl sulfoxide and dimethylformamide, particularly preferably methylene chloride, toluene, acetone, acetonitrile and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines. Potassium carbonate, sodium hydroxide and sodium methoxide are particularly preferred.

The bases are in general used in an excess or, if desired, as a solvent.

The starting materials are in general reacted with one another in equimolar amounts. It may be advantageous for the yield to employ IIIa in an excess or deficit based on IIa.

The starting substances of the formula IIa required for the preparation of the compounds I are known in the literature. The corresponding reports are cited in connection with the description of the preparation of the individual groups R'.

The starting substances of the formula IIIa can [lacuna] in a manner known per se by reaction of a β-dicarbonyl compound IV with a 5-aminopyrazole Va or a cyanoacetic hydrazide Vb.

Z.46: [sic]

The reaction of the P-dicarbonyl compound IV with the 5-aminopyrazole Va is carried out in a manner known per se [Liebigs Ann. Chem. 647 (1961), 116] in an inert solvent in the presence of an acid or of a catalyst at from 0° C. to 200° C., preferably 20° C. to 150° C., in particular 20° C. to 120° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol and also dimethyl sulfoxide, dimethylformamide and water. Mixtures of the solvents mentioned can also be used.

Acids and acidic catalysts used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and also organic acids such as formic acid, acetic acid, trifluoroacetic acid, propionic acid, oxalic acid and citric acid.

The acids are in general employed in catalytic amounts, but they can also be used in equimolar amounts, in an excess or as a solvent.

The starting materials are in general reacted with one another in equimolar amounts. It may be advantageous for the yield to employ IV in an excess or deficit based on V.

The reaction of the β-dicarbonyl compound IV with the cyanoacetic hydrazide Vb is carried out in a manner known per se [Liebigs Ann. Chem. 647 (1961), 116] in an inert solvent either in the presence of a base or of an acid at from 0° C. to 150° C., preferably 0° C. to 100° C., in particular 20° C. to 80° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, particularly preferably alcohols and water.

Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines. Sodium hydroxide and potassium hydroxide are particularly preferred. The bases are in general employed in catalytic amounts, but they can also be used in equimolar amounts or, if desired, as a solvent.

Acids used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium (IV) chloride and zinc(II) chloride, and also organic acids such as formic acid, acetic acid, propionic acid, oxalic acid, citric acid and trifluoroacetic acid.

The acids are in general employed in catalytic amounts, but they can also be used in equimolar amounts, in an excess or, if desired, as a solvent. The starting materials are in general reacted with one another in equimolar amounts. It may be advantageous for the yield to employ IV in an excess or deficit based on Vb.

In the preparation of the compounds I where $Y_n$ is C≡C, a procedure is in general followed in which a phenylacetylene of the formula IIb is reacted in a manner known per se in an inert solvent in the presence of a noble metal catalyst with a pyrazolopyrimidinyl halide of the formula IIIb.

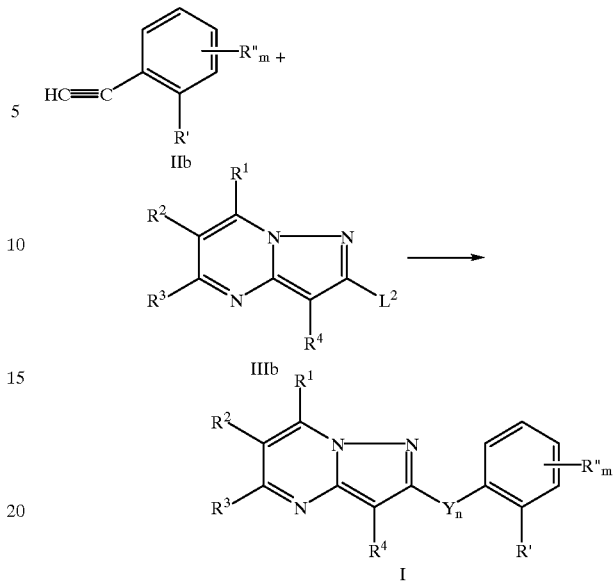

Z in the formula is [sic]

$L^2$ in the formula IIIb is a halogen atom (eg. fluorine, chlorine, bromine or iodine, preferably bromine or iodine).

This reaction is customarily carried out at from 0° C. to 200° C., preferably 150° C. to 160° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably tetrahydrofuran. Mixtures of the solvents mentioned can also be used.

Noble metal catalysts used are $Pd(OCOCH_3)_2$, $PdCl_2$, $Pd[P(C_6H_5)_3]_4$ and $NiCl_2$.

The noble metal catalysts are in general employed in amounts from 0.1 mol % to 100 mol %, preferably 5 mol % to 50 mol %, in particular 10 mol % to 50 mol %, based on the compound IIb.

The starting materials are in general reacted with one another in equimolar amounts. It may be advantageous for the yield to employ IIb in an excess or deficit based on IIIb.

The starting substances IIb required for this [sic] preparation of the compounds I are known in the literature (EP-A 582 925; DE-A 42 26 557) or can be prepared according to the references cited.

The pyrazolopyrimidinyl halides of the formula IIIb are likewise known or can be prepared from the corresponding alcohols of the formula IIIa (X═O) according to Liebigs Ann. Chem. 647 (1961), 116.

In the preparation of the compounds I where $Y_n$ is $CH_2O^*$, $CH_2S^*$ or $CH_2NR^{a*}$ [collectively designated as $CH_2X$], a procedure is in general followed in which an appropriate phenyl derivative IIc is reacted in a manner known per se in an inert solvent in the presence of a base with a pyrazolopyrimidinylmethylene halide of the formula IIIc.

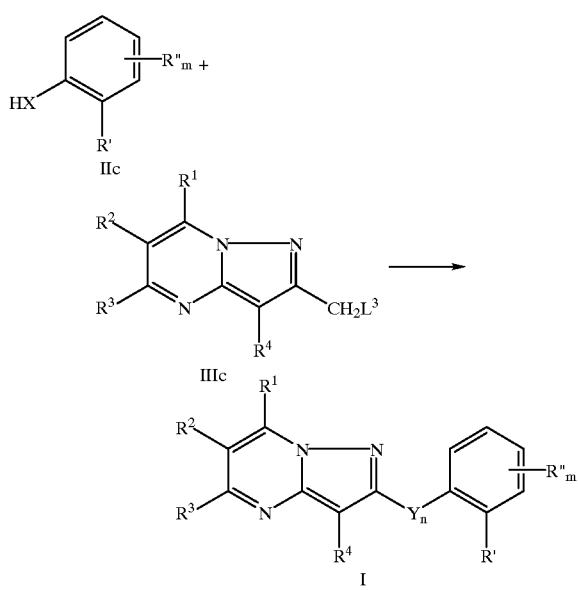

L³ in the formula IIIc is a nucleophilically replaceable leaving group such as halogen (eg. chlorine, bromine or iodine) or a sulfonate (eg. trifluoromethylsulfonate, phenylsulfonate or p-methylphenylsulfonate).

This reaction is customarily carried out at from 0° C. to 200° C., preferably 15° C. to 150° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably acetone, dimethylformamide and dimethyl sulfoxide. Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines. Potassium carbonate, sodium hydroxide and sodium methoxide are particularly preferred. The bases are in general employed in an excess or, if desired, as a solvent.

The starting materials are in general reacted with one another in equimolar amounts. It may be advantageous for the yield to employ IIc in an excess or deficit based on IIIc.

The starting substances IIc required for this [sic] preparation of the compounds I are known in the literature (EP-A 260 794; GB-A 2 249 092) or can be prepared according to the references cited.

The pyrazolopyrimidinylmethylene halides of the formula IIIc are likewise known or can be prepared from the corresponding methyl compounds by halogenation with elemental bromine or N-bromosuccinimide according to known methods [Farmaco. ed. Sci. 39 (1984), 888; J. Org. Chem. 53 (1988), 2055; Can. J. Chem. 60 (1982), 1233].

In the preparation of the compounds I where $Y_n$ is O, S or $NR^5$ [collectively designated as X], a procedure is in general followed in which an appropriate phenyl derivative of the formula IIc is coupled in a manner known per se a [sic] an inert solvent in the presence of a base with a pyrazolopyrimidinyl halide of the formula IIIb.

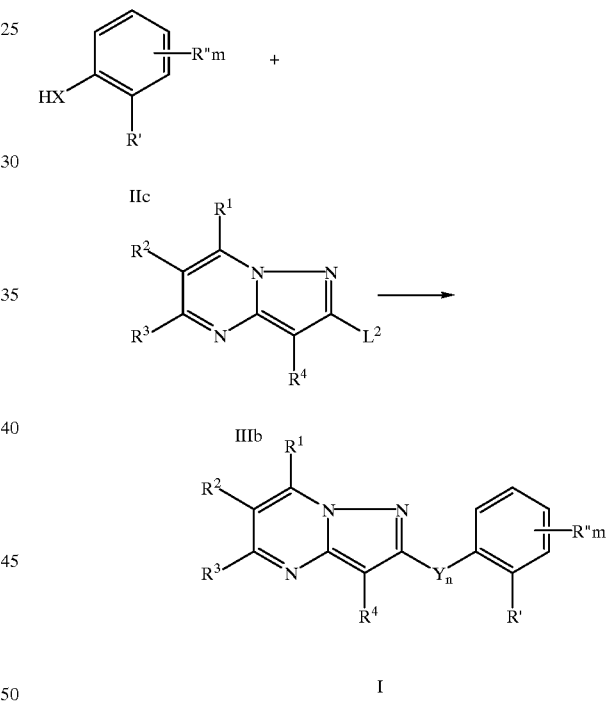

The coupling is carried out in an inert solvent in the presence of a base and, if appropriate, in the presence of a transition metal catalyst in the sense of an Ullmann coupling [Russ. Chem. Rev. 43 (1974), 679; J. Org. Chem. 29 (1964), 977] or in the sense of a nucleophilic substitution reaction [J. Chem. Soc. 1942, 381; J. Heterocycl. Chem. 15 (1978), 1513].

Compounds I where $Y_n$ is $CR^a$=$CR^b$ can additionally be obtained by reacting a benzylphosphorus compound of the formula IId in a manner known per se according to a Wittig reaction or a Wittig-Horner reaction in an inert organic solvent in the presence of a base with a methylpyrazolopyrimidine of the formula IIId.

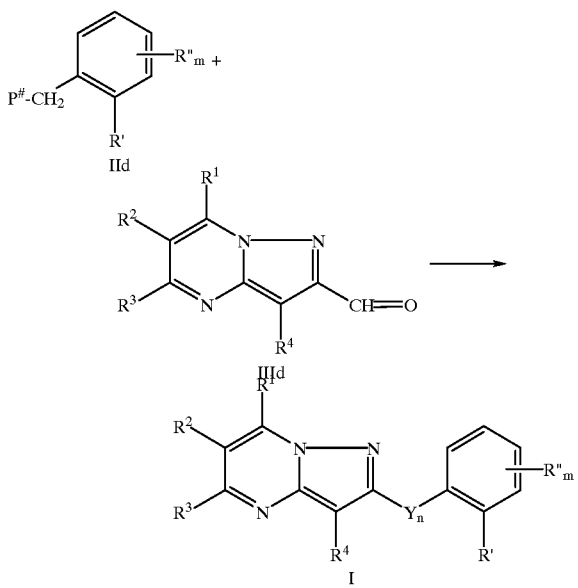

P# in the formula IId is a triarylphosphonium radical (eg. triphenylphosphonium chloride or triphenylphosphonium bromide) or a dialfylphosphino [sic] group (eg. dimethylphosphino, diethylphosphino or diisopropylphosphino).

This reaction is customarily carried out at from −30° C. to 60° C., preferably 0° C. to 40° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butylether methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably diethyl ether, tetrahydrofuran, dimethyl sulfoxide and dimethylformamide. Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines. Sodium methoxide, potassium tert-butoxide, sodium hydride, potassium carbonate and sodium hydride [sic] are particularly preferred. The bases are in general employed in an excess or, if desired, as a solvent.

The starting materials are in general reacted with one another in equimolar amounts. It may be advantageous for the yield to employ IId in an excess or deficit based on IIId.

The starting substances IId required for this [sic] preparation of the compounds I are known in the literature or can be prepared according to the references cited.

Compounds I in which $Y_n$ is $CR^a=CR^b$ can additionally be obtained in a similar manner to the above process by reacting a benzaldehyde of the formula IIe in a manner known per se according to a Wittig reaction or a Horner-Wittig reaction in an inert organic solvent in the presence of a base with a pyrazolopyrimidinephosphorus compound of the formula IIIe.

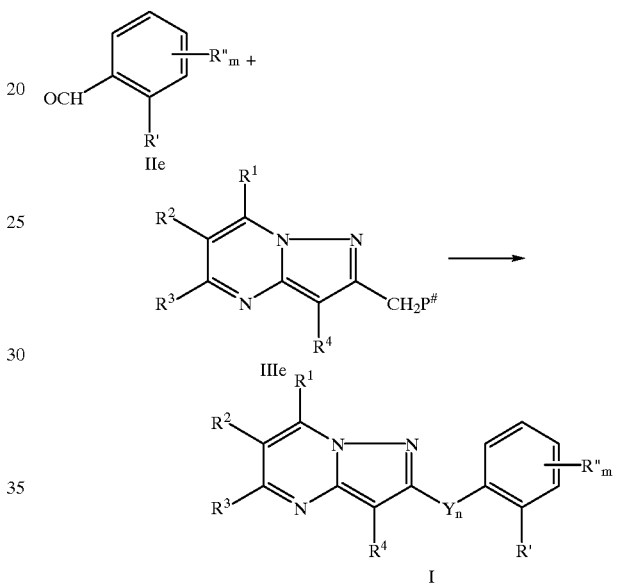

P# in the formula IIIe is a triarylphosphonium radical (eq. triphenylphosphonium chloride or triphenylphosphonium bromide) or a dialfylphosphino [sic] group (eg. dimethylphosphino, diethylphosphino or diisopropylphosphino).

This reaction is customarily carried out at from −30° C. to 60° C., preferably 0° C. to 40° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably diethyl ether, tetrahydrofuran, dimethyl sulfoxide and dimethylformamide. Mixtures of the solvents mentioned can also be used.

Suitable bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, eg. tertiary amines such as trimethylamine, triethylamine, triisopropylethylamine and N-methylpiperidine, pyridine, substituted pyridines such as collidine, lutidine and 4-dimethylaminopyridine and also bicyclic amines. Sodium methoxide, potassium tert-butoxide, sodium hydride and potassium carbonate are particularly preferred. The bases are in general employed in an excess or, if desired, as a solvent. The starting materials are in general reacted with one another in equimolar amounts.

It may be advantageous for the yield to employ IIe in an excess or deficit based on IIIe.

The starting substances IIe required for this [sic] preparation of the compounds I are known in the literature (EP-A 499 823; EP-A 544 587; EP-A 621 277) or can be prepared according to the references cited. Starting substances IIIe required for the preparation of the compounds I can be prepared from the corresponding pyrazolopyrimidinylmethyl halides of the formula IIIc by phosphorylation according to known methods [Synthesis 8 (1992), 743; Indian J. Chem. 22 (1983), 1050].

The reaction mixtures are worked up in a customary manner, eg. by mixing with water, separating the phases and if necessary chromatographically purifying the crude products. The intermediates and final products are obtained in some cases in the form of colorless or slightly brownish, viscous oils which are freed from volatile components or purified under reduced pressure and at moderately elevated temperature. If the intermediates and final products are obtained as solids, purification can also be carried out by recrystallization or digestion.

Compounds I where $Y_n$ is $OCH_2$ are particularly preferably obtained starting from the corresponding alcohols of the formula IIa.1 and phthalides of the formula VI according to the following reaction scheme.

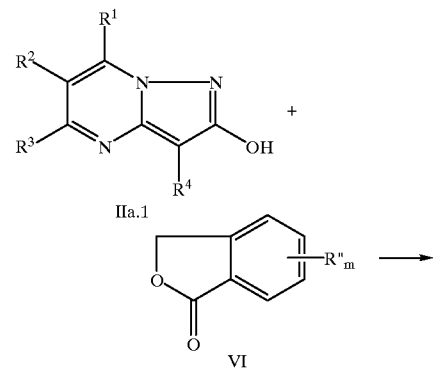

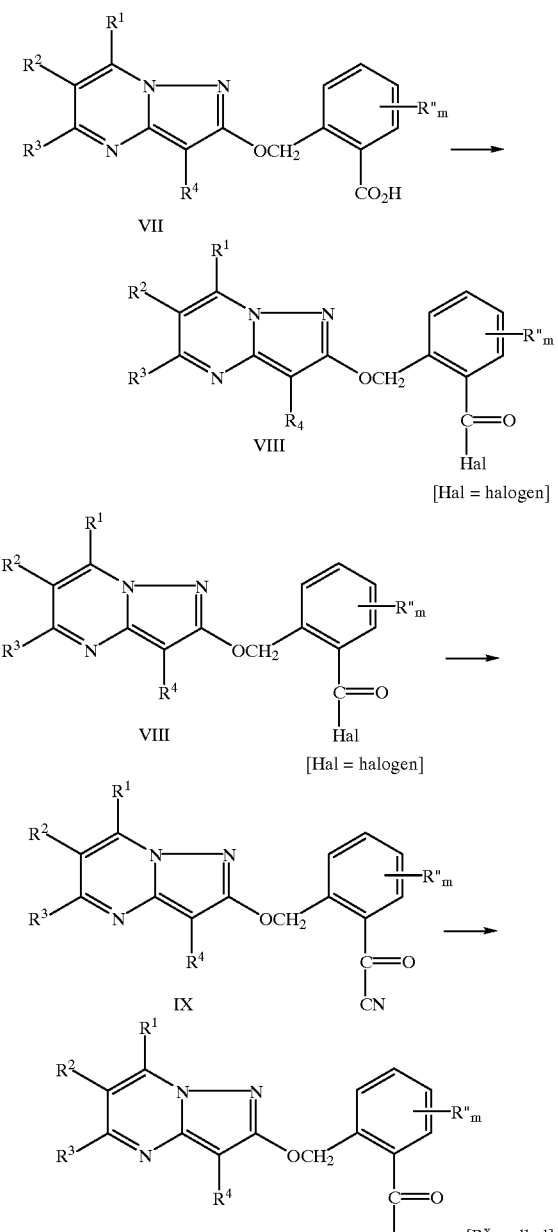

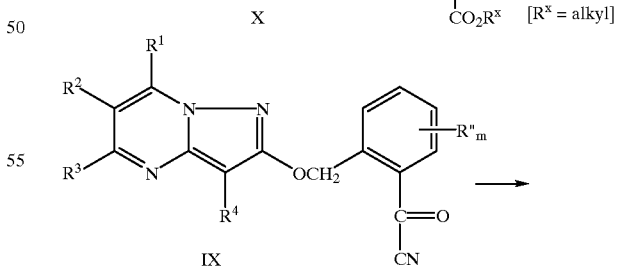

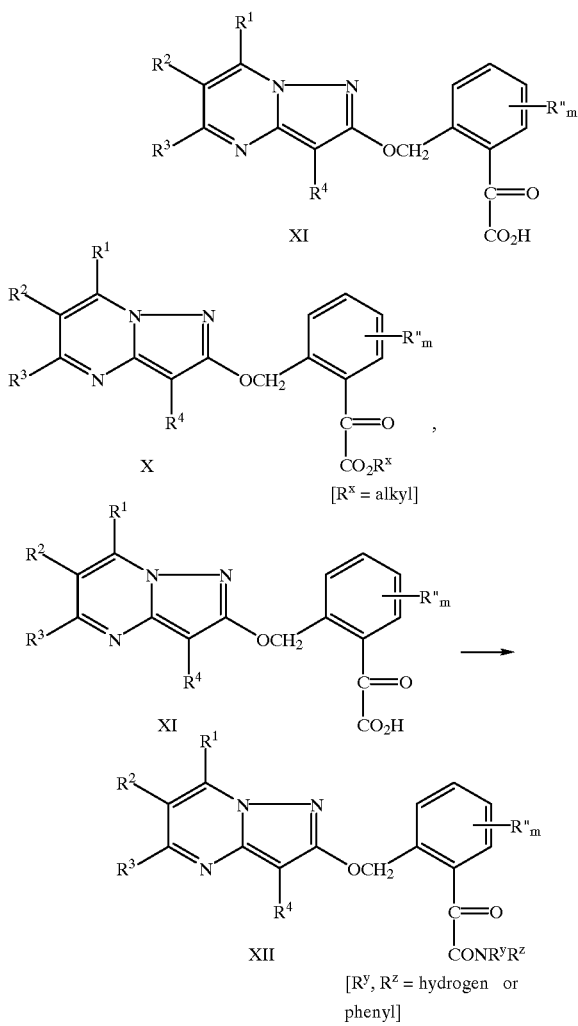

The reaction of the alcohols IIa.1 with the phthalides VI is carried out according to the conditions described in EP-A 493 711. The benzoic acids VII thus obtained can be converted into the corresponding cyanocarbonyls IX via the carbonyl halide intermediates VIII.

Starting from the cyanocarbonyls IX, the corresponding α-keto-esters X are obtained on the one hand in the course of the Pinner reaction [Angew. Chem. 94 (1982), 1] or the corresponding α-keto-carboxylic acids XI by hydrolysis [J. Med. Chem. 20 (1977), 791.

Both X and XI can be amidated to the compounds XII according to Synthesis 1978, 622.

The α-ketoesters X or the α-ketoamides XII can be converted into the corresponding compounds I according to known processes [EP-A 348 766, EP-A 178 826, DE-A 36 23 921, DE-A 37 05 389].

The synthesis of the group R' is fundamentally carried out according to known methods.

Compounds I where R' is $H_3CO$—CO—●=$CHOCH_3$ are obtained, for example, by the processes described in EP-A 178 826, EP-A 226 917, EP-A 242 081 and in EP-A 278 595.

Compounds I where R' is $H_3CO$—CO—●=$NOCH_3$ or HO—CO—●=$NOCH_3$ are obtained, for example, by the processes described in EP-A 253 213 and in EP-A 254 426.

Compounds I in which R' is $H_3CNH$—CO—●=$CHOCH_3$, $H_3CNH$—CO—●=$NOCH_3$ or $H_2N$—CO—●=$NOCH_3$ are obtained, for example, by the processes described in EP-A 398 692 and in EP-A 463 488.

Compounds I where R' is $H_3CO$—CO—●=$CHCH_3$ or $H_3CO$—CO—●=$CHCH_2CH_3$ are obtained, for example, by the processes described in EP-A 513 580.

Compounds I where R' is $H_3C$—CO—●=$NOCH_3$ or $H_3CCH_2$—CO—●=$NOCH_3$ are obtained, for example, by the processes described in EP-A 498 188.

Compounds I where R' is $N(OCH_3)$—$CO_2CH_3$, $N(CH_3)$—$CO_2CH_3$ or $N(CH_2CH_3)$—$CO_2CH_3$ are obtained, for example, by the processes described in EP-A 498 396 and WO-A 93/15,046.

Compounds I where R' is $CH(OCH_3)$—$CO_2CH_3$ or $CH(OCH_3)$—$CONHCH_3$ are obtained, for example, by the processes described in DE Appl. No. 44 32 336.0.

Compounds I where R' is a group R'.1, R'.2, R'.3 or R'.4 are obtained, for example, by the processes described in WO-A 94/22,844.

In the definitions of the symbols given under the above formulae, collective terms were used which are generally representative of the following substituents:

halogen: fluorine, chlorine, bromine and iodine;

alkyl: saturated, straight-chain or branched hydrocarbons having 1 to 4, 6 or 10 carbon atoms, eg. $C_1$—$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 4, 6 or 10 carbon atoms (as mentioned above), it being possible for the hydrogen atoms in these groups to be partially or completely replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4, 6 or 10 carbon atoms (as mentioned above), which are bonded to the structure via an oxygen atom (—O—);

haloalkoxy: straight-chain or branched haloalkyl groups having 1 to 4, 6 or 10 carbon atoms (as mentioned above), which are bonded to the structure via an oxygen atom (—O—);

alkylthio: straight-chain or branched alkyl groups having 1 to 4, 6 or 10 carbon atoms (as mentioned above), which are bonded to the structure via a sulfur atom (—S—);

haloalkylthio: straight-chain or branched haloalkyl groups having 1 to 4, 6 or 10 carbon atoms (as mentioned above), which are bonded to the structure via a sulfur atom (—S—);

alkylamino: a straight-chain or branched alkyl group having 1 to 4 carbon atoms (as mentioned above), which is bonded to the structure via an amino group (—NH—) or which is bonded to the structure via a group —NY$^1$— or —NZ$^a$—;

dialkylamino: two straight-chain or branched alkyl groups having 1 to 4 carbon atoms (as mentioned above), which are independent of one another and are bonded to the structure via a nitrogen atom (—N:);

alkylcarbonyl: a straight-chain or branched alkyl group having 1 to 4 carbon atoms (as mentioned above), which is bonded to the structure via a carbonyl group (—CO—);

alkylcarbonyloxy: a straight-chain or branched alkyl group having 1 to 4 carbon atoms (as mentioned above), which is bonded to the structure via a carbonyloxy group (—CO$_2$—);

alkylcarbonylamino: a straight-chain or branched alkyl group having 1 to 4 carbon atoms (as mentioned above), which is bonded to the structure via a carbonylamino group (—CONH—);

alkoxycarbonyl: a straight-chain or branched alkoxy group having 1 to 4 carbon atoms (as mentioned above), which is bonded to the structure via a carbonyl group (—CO—);

haloalkoxycarbonyl: a straight-chain or branched haloalkoxy group having 1 to 4 carbon atoms (as mentioned above), which is bonded to the structure via a carbonyl group (—CO—);

alkylthiocarbonyl: a straight-chain or branched alkylthio group having 1 to 4 carbon atoms (as mentioned above), which is bonded to the structure via a carbonyl group (—CO—);

haloalkylthiocarbonyl: a straight-chain or branched haloalkylthio [sic] group having 1 to 4 carbon atoms (as mentioned above), which is bonded to the structure via a carbonyl group (—CO—);

alkylaminocarbonyl: a straight-chain or branched alkylamino group having 1 to 4 carbon atoms (as mentioned above), which is bonded to the structure via a carbonyl group (—CO—);

dialkylaminocarbonyl: a dialkylamino group (as mentioned above), which is bonded to the structure via a carbonyl group (—CO—);

alkoxycarbonyloxy: a straight-chain or branched alkoxy group having 1 to 4 carbon atoms (as mentioned above), which is bonded to the structure via a carbonyloxy group (—CO$_2$—);

haloalkoxycarbonyloxy: a straight-chain or branched haloalkoxy group having 1 to 4 carbon atoms (as mentioned above), which is bonded to the structure via a carbonyloxy group (—CO$_2$—);

alkylthiocarbonyloxy: a straight-chain or branched alkylthio group having 1 to 4 carbon atoms (as mentioned above), which is bonded to the structure via a carbonyloxy group (—CO$_2$—);

haloalkylthiocarbonyloxy: a straight-chain or branched haloalkylthio group having 1 to 4 carbon atoms (as mentioned above), which is bonded to the structure via a carbonyloxy group (—CO$_2$—);

alkylaminocarbonyloxy: a straight-chain or branched alkylamino group having 1 to 4 carbon atoms (as mentioned above), which is bonded to the structure via a carbonyloxy group (—CO$_2$—);

dialkylaminocarbonyloxy: a dialkylamino group (as mentioned above), which is bonded to the structure via a carbonyloxy group (—CO$_2$—);

alkoxycarbonylamino: a straight-chain or branched alkoxy group having 1 to 4 carbon atoms (as mentioned above), which is bonded to the structure via a carbonylamino group (—CONH—);

haloalkoxycarbonylamino: a straight-chain or branched haloalkoxy group having 1 to 4 carbon atoms (as mentioned above), which is bonded to the structure via a carbonylamino group (—CONH—);

alkylthiocarbonylamino: a straight-chain or branched alkylthio group having 1 to 4 carbon atoms (as mentioned above), which is bonded to the structure via a carbonylamino group (—CONH—);

haloalkylthiocarbonylamino: a straight-chain or branched haloalkylthio group having 1 to 4 carbon atoms (as mentioned above), which is bonded to the structure via a carbonylamino group (—CONH—);

alkylaminocarbonylamino: a straight-chain or branched alkylamino group having 1 to 4 carbon atoms (as mentioned above), which is bonded to the structure via a carbonylamino group (—CONH—);

dialkylaminocarbonylamino: a dialkylamino group (as mentioned above), which is bonded to the structure via a carbonylamino group (—CONH—);

alkenyl: unsaturated, straight-chain or branched hydrocarbon radicals having 2 or 3 to 6 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3butenyl [sic], 1,1-dimethyl-2-propenyl, 1,2-dimethyl-1-propenyl, 1,2-dimethyl-2-propenyl, 1-ethyl-propenyl [sic], 1-ethyl-2-propenyl, 1-hexenyl, 2-hexenyl, 3-hexenyl, 4-hexenyl, 5-hexenyl, 1-methyl-1-pentenyl [sic], 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3pentenyl [sic], 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl- 2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl- 2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: an unsaturated, straight-chain or branched hydrocarbon group having 2 or 3 to 6 or 10 carbon atoms and a double bond in any desired position (as mentioned above), which is bonded to the structure via an oxygen atom (—O—);

alkenylthio: an unsaturated, straight-chain or branched hydrocarbon group having 2 or 3 to 6 or 10 carbon atoms and a double bond in any desired position (as mentioned above), which is bonded to the structure via a sulfur atom (—S—);

alkynyl: straight-chain or branched hydrocarbon groups having 2 or 3 to 6 or 10 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkynyloxy: a straight-chain or branched hydrocarbon group having 2 or 3 to 6 or 10 carbon atoms and a triple bond in any desired position (as mentioned above), which is bonded to the structure via an oxygen atom (—O—);

alkynylthio: a straight-chain or branched hydrocarbon group having 2 or 3 to 6 or 10 carbon atoms and a triple bond in any desired position (as mentioned above), which is bonded to the structure via a sulfur atom (—S—);

cycloalkyl: monocyclic alkyl groups having 3 to 6, 8 or 12 carbon ring members, eg. $C_3$–$C_8$-cycloalkyl such as cyclopropyl, cyclobutyl, cyclopentyl, cyclohexyl, cycloheptyl and cyclooctyl;

cycloalkoxy: a monocyclic alkyl group having 3 to 6, 8 or 12 carbon ring members (as mentioned above), which is bonded to the structure via an oxygen atom (—O—);

cycloalkylthio: a monocyclic alkyl group having 3 to 6, 8 or 12 carbon ring members (as mentioned above), which is bonded to the structure via a sulfur atom (—S—);

heterocyclyl: a saturated or partially unsaturated cyclic radical which, besides carbon atoms, contains heteroatoms from the group consisting of oxygen, sulfur and nitrogen as ring members: eg. 5- or 6-membered heterocycles (heterocyclyl) containing, besides carbon ring members, one to three nitrogen atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

heterocyclyloxy: a heterocyclyl radical (as mentioned above), which is bonded to the structure via an oxygen atom (—O—);

heterocyclylthio: a heterocyclyl radical (as mentioned above), which is bonded to the structure via a sulfur atom (—S—);

aryl: a mono- to trinuclear aromatic ring system containing 6 to 14 carbon ring members, eg. phenyl, naphthyl or anthracenyl;

arylalkyl: a mono- to trinuclear aromatic ring system containing 6 to 14 carbon ring members (as mentioned above), which is bonded to the structure via a straight-chain or branched alkyl group having 1 to 4, 6 or 10 carbon atoms;

aryloxy: a mono- to trinuclear aromatic ring system containing 6 to 14 carbon ring members (as mentioned above), which is bonded to the structure via an oxygen atom (—O—);

arylalkoxy: an arylalkyl group (as mentioned above), which is bonded to the structure via an oxygen atom (—O—);

arylthio: a mono- to trinuclear aromatic ring system containing 6 to 14 carbon ring members (as mentioned above), which is bonded to the structure via a sulfur atom (—S—);

heteroaryl: an aromatic ring system which, besides carbon ring members, can contain heteroatoms from the group consisting of oxygen, sulfur and nitrogen: aryl as mentioned above or mono- or binuclear heteroaryl, eg. 5-membered heteroaryl containing one to four nitrogen atoms or one to three nitrogen atoms and one sulfur or oxygen atom: 5-membered ring heteroaryl groups which, besides carbon atoms, can contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl containing one to three nitrogen atoms or one nitrogen atom and one oxygen or sulfur atom: 5-membered ring heteroaryl groups which, besides carbon atoms, can contain one to four nitrogen atoms or one to three nitrogen atoms and one sulfur or oxygen atom as ring members, and in which two adjacent carbon ring members or one nitrogen and one adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups which, besides carbon atoms, can contain one to four nitrogen atoms or one to three nitrogen atoms as ring members, and in which two adjacent carbon ring members or one nitrogen and one adjacent carbon ring member can be bridged by a buta-1,3-diene-1,4-diyl group, these rings being bonded to the structure via one of the nitrogen ring members;

6-membered heteroaryl containing one to three or one to four nitrogen atoms: 6-membered ring heteroaryl groups which, besides carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

heteroarylalkyl: a heteroaryl radical (as mentioned above), which is bonded to the structure via a straight-chain or branched alkyl group having 1 to 4, 6 or 10 carbon atoms;

heteroaryloxy: a heteroaryl radical (as mentioned above), which is bonded to the structure via an oxygen atom (—O—);

heteroarylalkoxy: a heteroarylalkyl group (as mentioned above), which is bonded to the structure via an oxygen atom (—O—);

heteroarylthio: a heteroaryl radical (as mentioned above), which is bonded to the structure via a sulfur atom (—S—).

The addition unsubst. or subst. in relation to alkyl, alkenyl and alkynyl groups is intended to express that these groups can be partially or completely halogenated (ie. the hydrogen atoms of these groups can be partially or completely replaced by identical or different halogen atoms as mentioned above (preferably fluorine, chlorine or bromine) and/or can carry one to three (preferably one) of the follwing radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, hetercyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkyl-amino, hetarylalkoxy, hetarylalkylthio, hetarylalkylamino and hetarylalkyl-N-alkylamino, each of which is unsubstituted or substituted by customary groups, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 to 4 carbon atoms.

The addition unsubst. or subst. in relation to the cyclic (saturated, unsaturated or aromatic) groups is intended to express that these groups can be partially or completely halogenated (ie. the hydrogen atoms of these groups can be partially or completely replaced by identical or different halogen atoms such as mentioned above (preferably fluorine, chlorine or bromine, in particular fluorine or chlorine) and/or can carry one to four (in particular one to three) of the following radicals: cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, and the alkenyl or alkynyl groups mentioned in these radicals containing 2 to 8, preferably 2 to 6, in particular 2 to 4, carbon atoms;

and/or one to three (in particular one) of the following radicals: cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, each of which is unsubstituted or substituted by customary groups, the aryl radicals preferably containing 6 to 10 ring members, in particular 6 ring members (phenyl), the hetaryl radicals in particular containing 5 or 6 ring members and the alkyl groups in these radicals preferably containing 1 to 6 carbon atoms, in particular 1 to 4 carbon atoms, and/or one or two (in particular one) of the following radicals: formyl or $CR^i=NOR^{ii}$, $R^i$ being hydrogen or alkyl and $R^{ii}$ being alkyl, alkenyl, alkynyl or arylalkyl and the hydrocarbon groups mentioned preferably containing 1 or 3 to 6 carbon atoms, in particular 1 to 4 carbon atoms, and aryl in particular being phenyl which is unsubstituted or can be substituted by customary groups, or in which two adjacent c atoms of the cyclic systems can carry a $C_3$–$C_5$-alkylene, $C_3$–$C_5$-alkenylene, oxy-$C_2$–$C_4$-alkylene, oxy-$C_1$–$C_3$-alkylenoxy, oxy-$C_2$–$C_4$-alkenylene, oxy-$C_2$–$C_4$-alkenylenoxy or butadienediyl group, it being possible for these bridges, in turn, to be partially or completely halogenated and/or to carry one to three, in particular one or two, of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are understood as meaning, in particular, the following substituents: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

With respect to the biological action, pyrazolo[1,5a]pyrimidines of the formula I are particularly preferred where the substituents have the following meanings:

$R^1$ and $R^3$ are hydrogen, cyano, nitro, hydroxyl, amino, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, aryl, aryl-$C_1$–$C_4$-alkyl, aryloxy, aryl-$C_1$–$C_4$-alkoxy, arylthio, heteroaryl, heteroaryl-$C_1$–$C_4$-alkyl, heteroaryloxy, heteroaryl-$C_1$–$C_4$-alkoxy, heteroarylthio, or $NR^cR^d$, $NR^cNR^dR^e$, $CO-R^c$, $CO_2-R^c$, $CO-NR^cR^d$, $O-CO-R^c$, $O-CO_2-R^c$, $O-CO-NR^cR^d$, $NR^c-CO-R^d$, $NR^c-CO_2-R^d$ or $NR^c-CO-NR^dR^e$;

$R^2$ is hydrogen, halogen, $C_1$–$C_6$-alkyl, $C_1$–$C_6$-haloalkyl, $C_1$–$C_6$-alkoxy, $C_1$–$C_6$-haloalkoxy, aryl, aryloxy, heteroaryl, heteroaryloxy, $CO-R^c$, $CO_2R^c$ or $CR^f=NOR^g$;

$R^4$ is hydrogen, cyano, nitro, nitroso, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, aryl, aryl-$C_1$–$C_4$-alkyl, aryloxy, aryl-$C_1$–$C_4$-alkoxy, arylthio, heteroaryl, heteroaryl-$C_1$–$C_4$-alkyl, heteroaryloxy, heteroaryl-$C_1$–$C_4$-alkoxy, heteroarylthio, or $NR^cR^d$, $CO-R^c$, $CO_2-R^c$ or $CR^f=NOR^g$;

$R^c$, $R^d$ and $R^e$ are hydrogen, $C_1$–$C_6$-alkyl, $C_3$–$C_6$-alkenyl, $C_3$–$C_6$-alkynyl, aryl, aryl-$C_1$–$C_4$-alkyl, heteroaryl or heteroaryl-$C_1$–$C_4$-alkyl;

$R^f$ is hydrogen, cyano, halogen, p2 $C_1$–$C_6$-alkyl, $C_1$–$C_6$-alkoxy, $C_1$–$C_6$-alkylthio, $C_3$–$C_6$-alkenyl, $C_3$–$C_6$-alkenyloxy, $C_3$–$C_6$-alkenylthio, $C_3$–$C_6$-alkynyl, $C_3$–$C_6$-alkynyloxy or $C_3$–$C_6$-alkynylthio, it being possible for these groups to be partially or completely halogenated and to carry one to three of the following radicals: cyano, nitro, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_3$–$C_6$-cycloalkoxy, aryl, aryloxy, heteroaryl or heteroaryloxy, it being possible for the cyclic radicals in turn to be partially or completely halogenated and/or to carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino and di-$C_1$–$C_4$-alkylamino;

$C_3$–$C_6$-cycloalkyl, $C_3$–$C_6$-cycloalkyloxy, $C_3$–$C_6$-cycloalkylthio, heterocyclyl, heterocyclyloxy, heterocyclylthio, aryl, aryloxy, arylthio, heteroaryl, heteroaryloxy or heteroarylthio, it being possible for these groups to be partially or completely halogenated and to carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-cycloalkyl, $C_3$–$C_6$-cycloalkoxy, aryl, aryloxy, heteroaryl or heteroaryloxy, it being possible for the cyclic radicals in turn to be partially or completely halogenated and/or to carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino and di-$C_1$–$C_4$-alkyl-amino;

$R^g$ is hydrogen, $C_1$–$C_{10}$-alkyl, $C_3$–$C_{10}$-alkenyl or $C_3$–$C_{10}$-alkynyl, it being possible for these groups to be partially or completely halogenated and to carry one to three of the following radicals: cyano, nitro, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_1$–$C_4$-alkylcarbonyl, $C_1$–$C_4$-alkylcarbonyloxy, $C_1$–$C_4$-alkylcarbonylamino, $C_1$–$C_4$-alkoxycarbonyl, $C_1$–$C_4$-haloalkoxycarbonyl, $C_1$–$C_4$-alkylthiocarbonyl, $C_1$–$C_4$-haloalkylthiocarbonyl, $C_1$–$C_4$-alkylaminocarbonyl, di-$C_1$–$C_4$-alkylaminocarbonyl, $C_1$–$C_4$-alkoxycarbonyloxy, $C_1$–$C_4$-haloalkoxycarbonyloxy, $C_1$–$C_4$-alkylthiocarbonyloxy, $C_1$–$C_4$-haloalkylthiocarbonyloxy, $C_1$–$C_4$-alkylaminocarbonyloxy, di-$C_1$–$C_4$-alkylaminocarbonyloxy, $C_1$–$C_4$-alkoxycarbonylamino, $C_1$–$C_4$-haloalkoxycarbonylamino, $C_1$–$C_4$-alkylthiocarbonylamino, $C_1$–$C_4$-haloalkylthiocarbonylamino, $C_1$–$C_4$-alkylaminocarbonylamino, di-$C_1$–$C_4$-alkylaminocarbonylamino, $C_3$–$C_6$-cycloalkyl, $C_3$–$C_6$-cycloalkoxy, aryl, aryloxy, heteroaryl or heteroaryloxy, it being possible for the cyclic radicals in turn to be partially or completely halogenated and/or to carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino and di-$C_1$–$C_4$-alkylamino;

$C_3$–$C_6$-cycloalkyl, heterocyclyl, aryl or heteroaryl, it being possible for these groups to be partially or completely halogenated and to carry one to three of the following radicals: cyano, nitro, $C_1$–$C_4$-alkyl, $C_1$–$C_4$-haloallkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino, di-$C_1$–$C_4$-alkylamino, $C_1$–$C_4$-alkylcarbonyl, $C_1$–$C_4$-alkylcarbonyloxy, $C_1$–$C_4$-alkylcarbonylamino, $C_1$–$C_4$-alkoxycarbonyl, $C_1$–$C_4$-haloalkoxycarbonyl, $C_1$–$C_4$-alkylthiocarbonyl, $C_1$–$C_4$-haloalkylthiocarbonyl, $C_1$–$C_4$-alkylaminocarbonyl, di-$C_1$–$C_4$-alkylaminocarbonyl, $C_1$–$C_4$-alkoxycarbonyloxy, $C_1$–$C_4$-haloalkoxycarbonyloxy, $C_1$–$C_4$-alkylthiocarbonyloxy, $C_1$–$C_4$-haloalkylthiocarbonyloxy, $C_1$–$C_4$-alkylaminocarbonyloxy, di-$C_1$–$C_4$-alkylaminocarbonyloxy, $C_1$–$C_4$-alkoxycarbonylamino, $C_1$–$C_4$-haloalkoxycarbonylamino, $C_1$–$C_4$- alkylthiocarbonylamino, $C_1$–$C_4$-haloalkylthiocarbonylamino, $C_1$–$C_4$-alkylaminocarbonylamino, di-$C_1$–$C_4$-alkylaminocarbonylamino, $C_3$–$C_6$-cycloalkyl, $C_3$–$C_6$-cycloalkoxy, aryl, aryloxy, heteroaryl or heteroaryloxy, it being possible for the cyclic radicals in turn to be partially or completely halogenated and/or to carry one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylamino and di-$C_1$–$C_4$-alkylamino.

With respect to their biological activity, in addition compounds of the formula I.A are particularly preferred, [sic]

With respect to their biological activity, in addition compounds of the formula I are particularly preferred where n is 1 and R' is $H_3CO$—CO—●=CHOCH$_3$ (I.A).

In particular, compounds I.A are preferred where R"$_m$ is hydrogen, halogen (particularly chlorine), $C_1$–$C_2$-alkyl (particularly methyl), $C_1$–$C_2$-haloalkyl (particularly trifluoromethyl) or $C_1$–$C_2$-alkoxy (particularly methoxy).

In particular, compounds I.A are also preferred where Y is $OCH_2$, $SCH_2$, O, CH=CH, C≡C or $CH_2$O (particularly O, $OCH_2$, $CH_2$O, CH=CH and C≡C).

In particular, compounds I.A are also preferred where the groups $R^1$, $R^2$, $R^3$ and $R^4$ are the following radicals: hydrogen, $C_1$–$C_4$-alkyl, $C_1$–$C_4$-haloalkyl, $C_1$–$C_4$-alkoxy, $C_1$–$C_4$-alkoxycarbonyl and phenyl.

With respect to their biological activity, in addition compounds of the formula I are particularly preferred where n is 1 and R' is $H_3CO$—CO—●=NOCH$_3$ (I.B).

In particular, compounds I.B are preferred where R"$_m$ is hydrogen, halogen (particularly chlorine), $C_1$–$C_2$-alkyl (particularly methyl), $C_1$–$C_2$-haloalkyl (particularly trifluoromethyl) or $C_1$–$C_2$-alkoxy (particularly methoxy).

In particular, compounds I.B are also preferred where Y is $OCH_2$, $SCH_2$, O, CH=CH, C≡C or $CH_2$O (particularly O, $OCH_2$, $CH_2$O, CH=CH and C≡C).

In particular, compounds I.B are also preferred where the groups $R^1$, $R^2$, $R^3$ and $R^4$ are the following radicals: hydrogen, $C_1$–$C_4$-alkyl, $C_1$–$C_4$-haloalkyl, $C_1$–$C_4$-alkoxy, $C_1$–$C_4$-alkoxycarbonyl and phenyl.

With respect to their biological activity, in addition compounds of the formula I are particularly preferred where n is 1 and R' is $H_3CNH$—CO—●=NOCH$_3$ (I.C).

In particular, compounds I.C are preferred where R"$_m$ is hydrogen, halogen (particularly chlorine), $C_1$–$C_2$-alkyl (particularly methyl), $C_1$–$C_2$-haloalkyl (particularly trifluoromethyl) or $C_1$–$C_2$-alkoxy (particularly methoxy).

In particular, compounds I.C. are also preferred where Y is $OCH_2$, $SCH_2$, O, CH=CH, C≡C or $CH_2$O (particularly O, $OCH_2$, $CH_2$O, CH=CH and C≡C).

In particular, compound I.D. are also preferred where the groups $R^1$, $R^2$, $R^3$ and $R^4$ are the following radicals: hydrogen, $C_1$–$C_4$-alkyl, $C_1$–$C_4$-haloalkyl, $C_1$–$C_4$-alkoxy, $C_1$–$C_4$-alkoxycarbonyl and phenyl.

With respect to their biological activity, in addition compounds of the formula I are particularly preferred where n is 1 and R' is $H_3CO$—CO—●=CHCH$_3$ (I.D).

In particular, compounds I.D are preferred where R"$_m$ is hydrogen, halogen (particularly chlorine), $C_1$–$C_2$-alkyl (particularly methyl), $C_1$–$C_2$-haloalkyl (particularly trifluoromethyl) or $C_1$–$C_2$-alkoxy (particularly methoxy).

In particular, compounds I.D are also preferred where Y is $OCH_2$, $SCH_2$, O, CH=CH, C≡C or $CH_2$O (particularly O, $OCH_2$, $CH_2$O, CH=CH and C≡C).

In particular, compounds I.D are also preferred where the groups $R^1$, $R^2$, $R^3$ and $R^4$ are the following radicals: hydrogen, $C_1$–$C_4$-alkyl, $C_1$–$C_4$-haloalkyl, $C_1$–$C_4$-alkoxy, $C_1$–$C_4$-alkoxycarbonyl and phenyl.

With respect to their biological activity, in addition compounds of the formula I are particularly preferred where n is 1 and R' is N($OCH_3$)—$CO_2CH_3$ (I.E).

In particular, compounds I.E are preferred where R"$_m$ is hydrogen, halogen (particularly chlorine), $C_1$–$C_2$-alkyl (particularly methyl), $C_1$–$C_2$-haloalkyl (particularly trifluoromethyl) or $C_1$–$C_2$-alkoxy (particularly methoxy).

In particular, compounds I.E are also preferred where Y is $OCH_2$, $SCH_2$, O, CH=CH, C≡C or $CH_2$O (particularly O, $OCH_2$, $CH_2$O, CH=CH and C≡C).

In particular, compounds I.E are also preferred where the groups $R^1$, $R^2$, $R^3$ and $R^4$ are the following radicals: hydrogen, $C_1$–$C_4$-alkyl, $C_1$–$C_4$-haloalkyl, $C_1$–$C_4$-alkoxy, $C_1$–$C_4$-alkoxycarbonyl and phenyl.

With respect to the double bond of the group Y and/or of the group R', the compounds I can be present in the Z or E configuration. Accordingly, in the preparation of the compounds I mixtures of the possible isomers can be formed. In general, with respect to their biological activity, those compounds I are preferred where the double bond of the group Y and/or of the group R' is present in the E configuration.

In particular, the compounds I compiled in the following tables are preferred with respect to their use. The groups mentioned for a substituent in the tables are additionally considered per se (independently of the combination in which they are mentioned) to be a particularly preferred embodiment of the substituent concerned.

Table 1

Compounds of the general formula I.A where Y is oxygen, R"$_m$ is hydrogen and the combination of the substituents $R^1$, $R^2$, $R^3$ and $R^4$ for a compound in each case corresponds to one line of Table A formula I.A [sic].

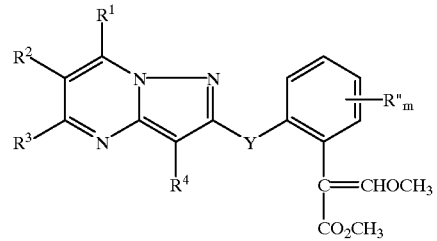

I.A

Table 2

Compounds of the general formula I.A where Y is sulfur, R"$_m$ is hydrogen and the combination of the substituents $R^1$, $R^2$, $R^3$ and $R^4$ for a compound in each case corresponds to one line of Table A.

Table 3

Compounds of the general formula I.A where Y is —NH—, R"$_m$ is hydrogen and the combination of the substituents $R^1$, $R^2$, $R^3$ and $R^4$ for a compound in each case corresponds to one line of Table A.

Table 4

Compounds of the general formula I.A where Y is $OCH_2$, R"$_m$ is hydrogen and the combination of the substituents $R^1$, $R^2$, $R^3$ and $R^4$ for a compound in each case corresponds to one line of Table A.

Table 5

Compounds of the general formula I.A where Y is $SCH_2$, R"$_m$ is hydrogen and the combination of the substituents $R^1$, $R^2$, $R^3$ and $R^4$ for a compound in each case corresponds to one line of Table A.

Table 6

Compounds of the general formula I.A where Y is $NHCH_2$, R"$_m$ is hydrogen and the combination of the substituents $R^1$, $R^2$, $R^3$ and $R^4$ for a compound in each case corresponds to one line of Table A.

Table 7

Compounds of the general formula I.A where Y is $CH_2O$, $R''_m$ is hydrogen and the combination of the substituents $R^1$, $R^2$, $R^3$ and $R^4$ for a compound in each case corresponds to one line of Table A.

Table 8

Compounds of the general formula I.A where Y is $CH_2S$, $R''_m$ is hydrogen and the combination of the substituents $R^1$, $R^2$, $R^3$ and $R^4$ for a compound in each case corresponds to one line of Table A.

Table 9

Compounds of the general formula I.A where Y is $CH_2NH$, $R''_m$ is hydrogen and the combination of the substituents $R^1$, $R^2$, $R^3$ and $R^4$ for a compound in each case corresponds to one line of Table A.

Table 10

Compounds of the general formula I.A where Y is $CH_2CH_2$, $R''_m$ is hydrogen and the combination of the substituents $R^1$, $R^2$, $R^3$ and $R^4$ for a compound in each case corresponds to one line of Table A.

Table 11

Compounds of the general formula I.A where Y is CH=CH, $R''_m$ is hydrogen and the combination of the substituents $R^1R^2$, $R^3$ and $R^4$ for a compound in each case corresponds to one line of Table A.

Table 12

Compounds of the general formula I.A where Y is C≡C, $R''_m$ is hydrogen and the combination of the substituents $R^1$, $R^2$, $R^3$ and $R^4$ for a compound in each case corresponds to one line of Table A.

Table 13

Compounds of the general formula I.B where Y is oxygen, $R''_m$ is hydrogen and the combination of the substituents $R^1$, $R^2$, $R^3$ and $R^4$ for a compound in each case corresponds to one line of Table A formula I.B [sic].

I.B

Table 14

Compounds of the general formula I.B where Y is sulfur, $R''_m$ is hydrogen and the combination of the substituents $R^1$, $R^2$, $R^3$ and $R^4$ for a compound in each case corresponds to one line of Table A.

Table 15

Compounds of the general formula I.B where Y is —NH—, $R''_m$ is hydrogen and the combination of the substituents $R^1$, $R^2$, $R^3$ and $R^4$ for a compound in each case corresponds to one line of Table A.

Table 16

Compounds of the general formula I.B where Y is $OCH_2$, $R''_m$ is hydrogen and the combination of the substituents $R^1$, $R^2$, $R^3$ and $R^4$ for a compound in each case corresponds to one line of Table A.

Table 17

Compounds of the general formula I.B where Y is $SCH_2$, $R''_m$ is hydrogen and the combination of the substituents $R^1$, $R^2$, $R^3$ and $R^4$ for a compound in each case corresponds to one line of Table A.

Table 18

Compounds of the general formula I.B where Y is $NHCH_2$, $R''_m$ is hydrogen and the combination of the substituents $R^1$, $R^2$, $R^3$ and $R^4$ for a compound in each case corresponds to one line of Table A.

Table 19

Compounds of the general formula I.B where Y is $CH_2O$, $R''_m$ is hydrogen and the combination of the substituents $R^1$, $R^2$, $R^3$ and $R^4$ for a compound in each case corresponds to one line of Table A.

Table 20

Compounds of the general formula I.B where Y is $CH_2S$, $R''_m$ is hydrogen and the combination of the substituents $R^1R^2$, $R^3$ and $R^4$ for a compound in each case corresponds to one line of Table A.

Table 21

Compounds of the general formula I.B where Y is $CH_2NH$, $R''_m$ is hydrogen and the combination of the substituents $R^1R^2$, $R^3$ and $R^4$ for a compound in each case corresponds to one line of Table A.

Table 22

Compounds of the general formula I.B where Y is $CH_2CH_2$, $R''_m$ is hydrogen and the combination of the substituents $R^1$, $R^2$, $R^3$ and $R^4$ for a compound in each case corresponds to one line of Table A.

Table 23

Compounds of the general formula I.B where Y is CH=CH, $R''_m$ is hydrogen and the combination of the substituents $R^1$, $R^2$, $R^3$ and $R^4$ for a compound in each case corresponds to one line of Table A.

Table 24

Compounds of the general formula I.B where Y is C≡C, $R''_m$ is hydrogen and the combination of the substituents $R^1R^2$, $R^3$ and $R^4$ for a compound in each case corresponds to one line of Table A.

Table 25

Compounds of the general formula I.C where Y is oxygen, $R''_m$ is hydrogen and the combination of the substituents $R^1R^2$, $R^3$ and $R^4$ for a compound in each case corresponds to one line of Table A.

I.C

Table 26

Compounds of the general formula I.C where Y is sulfur, $R''_m$ is hydrogen and the combination of the substituents $R^1$, $R^2$, $R^3$ and $R^4$ for a compound in each case corresponds to one line of Table A.

Table 27

Compounds of the general formula I.C where Y is —NH—, $R''_m$ is hydrogen and the combination of the substituents $R^1$, $R^2$, $R^3$ and $R^4$ for a compound in each case corresponds to one line of Table A.

Table 28

Compounds of the general formula I.C where Y is $OCH_2$, $R''_m$ is hydrogen and the combination of the substituents $R^1$, $R^2$, $R^3$ and $R^4$ for a compound in each case corresponds to one line of Table A.

Table 29
Compounds of the general formula I.C where Y is $SCH_2$, $R''_m$ is hydrogen and the combination of the substituents $R^1$, $R^2$, $R^3$ and $R^4$ for a compound in each case corresponds to one line of Table A.

Table 30
Compounds of the general formula I.C where Y is $NHCH_2$, $R''_m$ is hydrogen and the combination of the substituents $R^1$, $R^2$, $R^3$ and $R^4$ for a compound in each case corresponds to one line of Table A.

Table 31
Compounds of the general formula I.C where Y is $CH_2O$, $R''_m$ is hydrogen and the combination of the substituents $R^1$, $R^2$, $R^3$ and $R^4$ for a compound in each case corresponds to one line of Table A.

Table 32
Compounds of the general formula I.C where Y is $CH_2S$, $R''_m$ is hydrogen and the combination of the substituents $R^1$, $R^2$, $R^3$ and $R^4$ for a compound in each case corresponds to one line of Table A.

Table 33
Compounds of the general formula I.C where Y is $CH_2NH$, $R''_m$ is hydrogen and the combination of the substituents $R^1$, $R^2$, $R^3$ and $R^4$ for a compound in each case corresponds to one line of Table A.

Table 34
Compounds of the general formula I.C where Y is $CH_2CH_2$, $R''_m$ is hydrogen and the combination of the substituents $R^1$, $R^2$, $R^3$ and $R^4$ for a compound in each case corresponds to one line of Table A.

Table 35
Compounds of the general formula I.C where Y is CH=CH, $R''_m$ is hydrogen and the combination of the substituents $R^1$, $R^2$, $R^3$ and $R^4$ for a compound in each case corresponds to one line of Table A.

Table 36
Compounds of the general formula I.C where Y is C≡C, $R''_m$ is hydrogen and the combination of the substituents $R^1$, $R^2$, $R^3$ and $R^4$ for a compound in each case corresponds to one line of Table A.

Table 37
Compounds of the general formula I.D where Y is oxygen, $R''_m$ is hydrogen and the combination of the substituents $R^1$, $R^2$, $R^3$ and $R^4$ for a compound in each case corresponds to one line of Table A.

I.D

Table 38
Compounds of the general formula I.D where Y is sulfur, $R''_m$ is hydrogen and the combination of the substituents $R^1$, $R^2$, $R^3$ and $R^4$ for a compound in each case corresponds to one line of Table A.

Table 39
Compounds of the general formula I.D where Y is —NH—, $R''_m$ is hydrogen and the combination of the substituents $R^1$, $R^2$, $R^3$ and $R^4$ for a compound in each case corresponds to one line of Table A.

Table 40
Compounds of the general formula I.D where Y is $OCH_2$, $R''_m$ is hydrogen and the combination of the substituents $R^1R^2$, $R^3$ and $R^4$ for a compound in each case corresponds to one line of Table A.

Table 41
Compounds of the general formula I.D where Y is $SCH_2$, $R''_m$ is hydrogen and the combination of the substituents $R^1$, $R^2$, $R^3$ and $R^4$ for a compound in each case corresponds to one line of Table A.

Table 42
Compounds of the general formula I.D where Y is $NHCH_2$, $R''_m$ is hydrogen and the combination of the substituents $R^1$, $R^2$, $R^3$ and $R^4$ for a compound in each case corresponds to one line of Table A.

Table 43
Compounds of the general formula I.D where Y is $CH_2O$, $R''_m$ is hydrogen and the combination of the substituents $R^1$, $R^2$, $R^3$ and $R^4$ for a compound in each case corresponds to one line of Table A.

Table 44
Compounds of the general formula I.D where Y is $CH_2S$, $R''_m$ is hydrogen and the combination of the substituents $R^1$, $R^2$, $R^3$ and $R^4$ for a compound in each case corresponds to one line of Table A.

Table 45
Compounds of the general formula I.D where Y is $CH_2NH$, $R''_m$ is hydrogen and the combination of the substituents $R^1$, $R^2$, $R^3$ and $R^4$ for a compound in each case corresponds to one line of Table A.

Table 46
Compounds of the general formula I.D where Y is $CH_2CH_2$, $R''_m$ is hydrogen and the combination of the substituents $R^1$, $R^2$, $R^3$ and $R^4$ for a compound in each case corresponds to one line of Table A.

Table 47
Compounds of the general formula I.D where Y is CH=CH, $R''_m$ is hydrogen and the combination of the substituents $R^1$, $R^2$, $R^3$ and $R^4$ for a compound in each case corresponds to one line of Table A.

Table 48
Compounds of the general formula I.D where Y is C≡C, $R''_m$ is hydrogen and the combination of the substituents $R^1R^2$, $R^3$ and $R^4$ for a compound in each case corresponds to one line of Table A.

Table 49
Compounds of the general formula I.E where Y is oxygen, $R''_m$ is hydrogen and the combination of the substituents $R^1$, $R^2$, $R^3$ and $R^4$ for a compound in each case corresponds to one line of Table A.

I.E

Table 50
Compounds of the general formula I.E where Y is sulfur, $R''_m$ is hydrogen and the combination of the substituents $R^1$, $R^2$, $R^3$ and $R^4$ for a compound in each case corresponds to one line of Table A.

Table 51

Compounds of the general formula I.E where Y is —NH—, $R''_m$ is hydrogen and the combination of the substituents $R^1$, $R^2$, $R^3$ and $R^4$ for a compound in each case corresponds to one line of Table A.

Table 52

Compounds of the general formula I.E where Y is $OCH_2$, $R''_m$ is hydrogen and the combination of the substituents $R^1R^2$, $R^3$ and $R^4$ for a compound in each case corresponds to one line of Table A.

Table 53

Compounds of the general formula I.E where Y is $SCH_2$, $R''_m$ is hydrogen and the combination of the substituents $R^1R^2$, $R^3$ and $R^4$ for a compound in each case corresponds to one line of Table A.

Table 54

Compounds of the general formula I.E where Y is $NHCH_2$, $R''_m$ is hydrogen and the combination of the substituents $R^1R^2$, $R^3$ and $R^4$ for a compound in each case corresponds to one line of Table A.

Table 55

Compounds of the general formula I.E where Y is $CH_2O$, $R''_m$ is hydrogen and the combination of the substituents $R^1$, $R^2$, $R^3$ and $R^4$ for a compound in each case corresponds to one line of Table A.

Table 56

Compounds of the general formula I.E where Y is $CH_2S$, $R''_m$ is hydrogen and the combination of the substituents $R^1$, $R^2$, $R^3$ and $R^4$ for a compound in each case corresponds to one line of Table A.

Table 57

Compounds of the general formula I.E where Y is $CH_2NH$, $R''_m$ is hydrogen and the combination of the substituents $R^1$, $R^2$, $R^3$ and $R^4$ for a compound in each case corresponds to one line of Table A.

Table 58

Compounds of the general formula I.E where Y is $CH_2CH_2$, $R''_m$ is hydrogen and the combination of the substituents $R^1$, $R^2$, $R^3$ and $R^4$ for a compound in each case corresponds to one line of Table A.

Table 59

Compounds of the general formula I.E where Y is CH=CH, $R''_m$ is hydrogen and the combination of the substituents $R^1$, $R^2$, $R^3$ and $R^4$ for a compound in each case corresponds to one line of Table A.

Table 60

Compounds of the general formula I.E where Y is C≡C, $R''_m$ is hydrogen and the combination of the substituents $R^1R^2$, $R^3$ and $R^4$ for a compound in each case corresponds to one line of Table A.

Table 61

Compounds of the general formula I.F where Y is oxygen, $R''_m$ is hydrogen and the combination of the substituents $R^1R^2$, $R^3$ and $R^4$ for a compound in each case corresponds to one line of Table A.

I.F

Table 62

Compounds of the general formula I.F where Y is sulfur, $R''_m$ is hydrogen and the combination of the substituents $R^1$, $R^2$, $R^3$ and $R^4$ for a compound in each case corresponds to one line of Table A.

Table 63

Compounds of the general formula I.F where Y is —NH—, $R''_m$ is hydrogen and the combination of the substituents $R^1$, $R^2$, $R^3$ and $R^4$ for a compound in each case corresponds to one line of Table A.

Table 64

Compounds of the general formula I.F where Y is $OCH_2$, $R''_m$ is hydrogen and the combination of the substituents $R^1$, $R^2$, $R^3$ and $R^4$ for a compound in each case corresponds to one line of Table A.

Table 65

Compounds of the general formula I.F where Y is $SCH_2$, $R''_m$ is hydrogen and the combination of the substituents $R^1$, $R^2$, $R^3$ and $R^4$ for a compound in each case corresponds to one line of Table A.

Table 66

Compounds of the general formula I.F where Y is $NHCH_2$, $R''_m$ is hydrogen and the combination of the substituents $R^1$, $R^2$, $R^3$ and $R^4$ for a compound in each case corresponds to one line of Table A.

Table 67

Compounds of the general formula I.F where Y is $CH_2O$, $R''_m$ is hydrogen and the combination of the substituents $R^1$, $R^2$, $R^3$ and $R^4$ for a compound in each case corresponds to one line of Table A.

Table 68

Compounds of the general formula I.F where Y is $CH_2S$, $R''_m$ is hydrogen and the combination of the substituents $R^1$, $R^2$, $R^3$ and $R^4$ for a compound in each case corresponds to one line of Table A.

Table 69

Compounds of the general formula I.F where Y is $CH_2NH$, $R''_m$ is hydrogen and the combination of the substituents $R^1R^2$, $R^3$ and $R^4$ for a compound in each case corresponds to one line of Table A.

Table 70

Compounds of the general formula I.F where Y is $CH_2CH_2$, $R''_m$ is hydrogen and the combination of the substituents $R^1$, $R^2$, $R^3$ and $R^4$ for a compound in each case corresponds to one line of Table A.

Table 71

Compounds of the general formula I.F where Y is CH=CH, $R''_m$ is hydrogen and the combination of the substituents $R^1$, $R^2$, $R^3$ and $R^4$ for a compound in each case corresponds to one line of Table A.

Table 72

Compounds of the general formula I.F where Y is C≡C, $R''_m$ is hydrogen and the combination of the substituents $R^1$, $R^2$, $R^3$ and $R^4$ for a compound in each case corresponds to one line of Table A.

Table 73

Compounds of the general formula I.G where Y is oxygen, R"$_m$ is hydrogen and the combination of the substituents R$^1$R$^2$, R$^3$ and R$^4$ for a compound in each case corresponds to one line of Table A.

I.G

Table 74

Compounds of the general formula I.G where Y is sulfur, R"$_m$ is hydrogen and the combination of the substituents R$^1$R$^2$, R$^3$ and R$^4$ for a compound in each case corresponds to one line of Table A.

Table 75

Compounds of the general formula I.G where Y is —NH—, R"$_m$ is hydrogen and the combination of the substituents R$^1$, R$^2$, R$^3$ and R$^4$ for a compound in each case corresponds to one line of Table A.

Table 76

Compounds of the general formula I.G where Y is OCH$_2$, R"$_m$ is hydrogen and the combination of the substituents R$^1$, R$^2$, R$^3$ and R$^4$ for a compound in each case corresponds to one line of Table A.

Table 77

Compounds of the general formula I.G where Y is SCH$_2$, R"$_m$ is hydrogen and the combination of the substituents R$^1$, R$^2$, R$^3$ and R$^4$ for a compound in each case corresponds to one line of Table A.

Table 78

Compounds of the general formula I.G where Y is NHCH$_2$, R"$_m$ is hydrogen and the combination of the substituents R$^1$, R$^2$, R$^3$ and R$^4$ for a compound in each case corresponds to one line of Table A.

Table 79

Compounds of the general formula I.G where Y is CH$_2$O, R"$_m$ is hydrogen and the combination of the substituents R$^1$, R$^2$, R$^3$ and R$^4$ for a compound in each case corresponds to one line of Table A.

Table 80

Compounds of the general formula I.G where Y is CH$_2$S, R"$_m$ is hydrogen and the combination of the substituents R$^1$, R$^2$, R$^3$ and R$^4$ for a compound in each case corresponds to one line of Table A.

Table 81

Compounds of the general formula I.G where Y is CH$_2$NH, R"$_m$ is hydrogen and the combination of the substituents R$^1$, R$^2$, R$^3$ and R$^4$ for a compound in each case corresponds to one line of Table A.

Table 82

Compounds of the general formula I.G where Y is CH$_2$CH$_2$, R"$_m$ is hydrogen and the combination of the substituents R$^1$, R$^2$, R$^3$ and R$^4$ for a compound in each case corresponds to one line of Table A.

Table 83

Compounds of the general formula I.G where Y is CH=CH, R"$_m$ is hydrogen and the combination of the substituents R$^1$, R$^2$, R$^3$ and R$^4$ for a compound in each case corresponds to one line of Table A.

Table 84

Compounds of the general formula I.G where Y is C≡C, R"$_m$ is hydrogen and the combination of the substituents R$^1$, R$^2$, R$^3$ and R$^4$ for a compound in each case corresponds to one line of Table A.

Table 85

Compounds of the general formula I.H where Y is oxygen, R"$_m$ is hydrogen and the combination of the substituents R$^1$, R$^2$, R$^3$ and R$^4$ for a compound in each case corresponds to one line of Table A.

I.H

Table 86

Compounds of the general formula I.H where Y is sulfur, R"$_m$ is hydrogen and the combination of the substituents R$^1$, R$^2$, R$^3$ and R$^4$ for a compound in each case corresponds to one line of Table A.

Table 87

Compounds of the general formula I.H where Y is —NH—, R"$_m$ is hydrogen and the combination of the substituents R$^1$, R$^2$, R$^3$ and R$^4$ for a compound in each case corresponds to one line of Table A.

Table 88

Compounds of the general formula I.H where Y is OCH$_2$, R"$_m$ is hydrogen and the combination of the substituents R$^1$, R$^2$, R$^3$ and R$^4$ for a compound in each case corresponds to one line of Table A.

Table 89

Compounds of the general formula I.H where Y is SCH$_2$, R"$_m$ is hydrogen and the combination of the substituents R$^1$R$^2$, R$^3$ and R$^4$ for a compound in each case corresponds to one line of Table A.

Table 90

Compounds of the general formula I.H where Y is NHCH$_2$, R"$_m$ is hydrogen and the combination of the substituents R$^1$, R$^2$, R$^3$ and R$^4$ for a compound in each case corresponds to one line of Table A.

Table 91

Compounds of the general formula I.H where Y is CH$_2$O, R"$_m$ is hydrogen and the combination of the substituents R$^1$, R$^2$, R$^3$ and R$^4$ for a compound in each case corresponds to one line of Table A.

Table 92

Compounds of the general formula I.H where Y is CH$_2$S, R"$_m$ is hydrogen and the combination of the substituents R$^1$, R$^2$, R$^3$ and R$^4$ for a compound in each case corresponds to one line of Table A.

Table 93

Compounds of the general formula I.H where Y is CH$_2$NH, R"$_m$ is hydrogen and the combination of the substituents R$^1$, R$^2$, R$^3$ and R$^4$ for a compound in each case corresponds to one line of Table A.

Table 94

Compounds of the general formula I.H where Y is CH$_2$CH$_2$, R"$_m$ is hydrogen and the combination of the substituents R$^1$R$^2$, R$^3$ and R$^4$ for a compound in each case corresponds to one line of Table A.

Table 95

Compounds of the general formula I.H where Y is CH=CH, $R''_m$ is hydrogen and the combination of the substituents $R^1R^2$, $R^3$ and $R^4$ for a compound in each case corresponds to one line of Table A.

Table 96

Compounds of the general formula I.H where Y is C≡C, $R''_m$ is hydrogen and the combination of the substituents $R^1R^2$, $R^3$ and $R^4$ for a compound in each case corresponds to one line of Table A.

Table 97

Compounds of the general formula I.K where Y is oxygen, $R''_m$ is hydrogen and the combination of the substituents $R^1R^2$, $R^3$ and $R^4$ for a compound in each case corresponds to one line of Table A.

I.K

Table 98

Compounds of the general formula I.K where Y is sulfur, $R''_m$ is hydrogen and the combination of the substituents $R^1$, $R^2$, $R^3$ and $R^4$ for a compound in each case corresponds to one line of Table A.

Table 99

Compounds of the general formula I.K where Y is —NH—, $R''_m$ is hydrogen and the combination of the substituents $R^1$, $R^2$, $R^3$ and $R^4$ for a compound in each case corresponds to one line of Table A.

Table 100

Compounds of the general formula I.K where Y is $OCH_2$, $R''_m$ is hydrogen and the combination of the substituents $R^1R^2$, $R^3$ and $R^4$ for a compound in each case corresponds to one line of Table A.

Table 101

Compounds of the general formula I.K where Y is $SCH_2$, $R''_m$ is hydrogen and the combination of the substituents $R^1$, $R^2$, $R^3$ and $R^4$ for a compound in each case corresponds to one line of Table A.

Table 102

Compounds of the general formula I.K where Y is $NHCH_2$, $R''_m$ is hydrogen and the combination of the substituents $R^1$, $R^2$, $R^3$ and $R^4$ for a compound in each case corresponds to one line of Table A.

Table 103

Compounds of the general formula I.K where Y is $CH_2O$, $R''_m$ is hydrogen and the combination of the substituents $R^1$, $R^2$, $R^3$ and $R^4$ for a compound in each case corresponds to one line of Table A.

Table 104

Compounds of the general formula I.K where Y is $CH_2S$, $R''_m$ is hydrogen and the combination of the substituents $R^1R^2$, $R^3$ and $R^4$ for a compound in each case corresponds to one line of Table A.

Table 105

Compounds of the general formula I.K where Y is $CH_2NH$, $R''_m$ is hydrogen and the combination of the substituents $R^1$, $R^2$, $R^3$ and $R^4$ for a compound in each case corresponds to one line of Table A.

Table 106

Compounds of the general formula I.K where Y is $CH_2CH_2$, $R''_m$ is hydrogen and the combination of the substituents $R^1$, $R^2$, $R^3$ and $R^4$ for a compound in each case corresponds to one line of Table A.

Table 107

Compounds of the general formula I.K where Y is CH=CH, $R''_m$ is hydrogen and the combination of the substituents $R^1$, $R^2$, $R^3$ and $R^4$ for a compound in each case corresponds to one line of Table A.

Table 108

Compounds of the general formula I.K where Y is C≡C, $R''_m$ is hydrogen and the combination of the substituents $R^1R^2$, $R^3$ and $R^4$ for a compound in each case corresponds to one line of Table A.

Table 109

Compounds of the general formula I.L where Y is oxygen, $R''_m$ is hydrogen and the combination of the substituents $R^1$, $R^2$, $R^3$ and $R^4$ for a compound in each case corresponds to one line of Table A.

I.L

Table 110

Compounds of the general formula I.L where Y is sulfur, $R''_m$ is hydrogen and the combination of the substituents $R^1$, $R^2$, $R^3$ and $R^4$ for a compound in each case corresponds to one line of Table A.

Table 111

Compounds of the general formula I.L where Y is —NH—, $R''_m$ is hydrogen and the combination of the substituents $R^1R^2$, $R^3$ and $R^4$ for a compound in each case corresponds to one line of Table A.

Table 112

Compounds of the general formula I.L where Y is $OCH_2$, $R''_m$ is hydrogen and the combination of the substituents $R^1$, $R^2$, $R^3$ and $R^4$ for a compound in each case corresponds to one line of Table A.

Table 113

Compounds of the general formula I.L where Y is $SCH_2$, $R''_m$ is hydrogen and the combination of the substituents $R^1R^2$, $R^3$ and $R^4$ for a compound in each case corresponds to one line of Table A.

Table 114

Compounds of the general formula I.L where Y is $NHCH_2$, $R''_m$ is hydrogen and the combination of the substituents $R^1$, $R^2$, $R^3$ and $R^4$ for a compound in each case corresponds to one line of Table A.

Table 115

Compounds of the general formula I.L where Y is $CH_2O$, $R''_m$ is hydrogen and the combination of the substituents $R^1R^2$, $R^3$ and $R^4$ for a compound in each case corresponds to one line of Table A.

Table 116

Compounds of the general formula I.L where Y is $CH_2S$, $R''_m$ is hydrogen and the combination of the substituents $R^1$, R², R³ and R⁴ for a compound in each case corresponds to one line of Table A.

Table 117
Compounds of the general formula I.L where Y is CH₂NH, R"$_m$ is hydrogen and the combination of the substituents R¹, R², R³ and R⁴ for a compound in each case corresponds to one line of Table A.

Table 118
Compounds of the general formula I.L where Y is CH₂CH₂, R"$_m$ is hydrogen and the combination of the substituents R¹, R², R³ and R⁴ for a compound in each case corresponds to one line of Table A.

Table 119
Compounds of the general formula I.L where Y is CH=CH, R"$_m$ is hydrogen and the combination of the substituents R¹, R², R³ and R⁴ for a compound in each case corresponds to one line of Table A.

Table 120
Compounds of the general formula I.L where Y is C≡C, R"$_m$ is hydrogen and the combination of the substituents R¹, R², R³ and R⁴ for a compound in each case corresponds to one line of Table A.

Table 121
Compounds of the general formula I.M where Y is oxygen, R"$_m$ is hydrogen and the combination of the substituents R¹, R², R³ and R⁴ for a compound in each case corresponds to one line of Table A.

I.M

[Chemical structure of formula I.M]

Table 122
Compounds of the general formula I.M where Y is sulfur, R"$_m$ is hydrogen and the combination of the substituents R¹R², R³ and R⁴ for a compound in each case corresponds to one line of Table A.

Table 123
Compounds of the general formula I.M where Y is —NH—, R"$_m$ is hydrogen and the combination of the substituents R¹R², R³ and R⁴ for a compound in each case corresponds to one line of Table A.

Table 124
Compounds of the general formula I.M where Y is OCH₂, R"$_m$ is hydrogen and the combination of the substituents R¹R², R³ and R⁴ for a compound in each case corresponds to one line of Table A.

Table 125
Compounds of the general formula I.M where Y is SCH₂, R"$_m$ is hydrogen and the combination of the substituents R¹, R², R³ and R⁴ for a compound in each case corresponds to one line of Table A.

Table 126
Compounds of the general formula I.M where Y is NHCH₂, R"$_m$ is hydrogen and the combination of the substituents R¹, R², R³ and R⁴ for a compound in each case corresponds to one line of Table A.

Table 127
Compounds of the general formula I.M where Y is CH₂O, R"$_m$ is hydrogen and the combination of the substituents R¹, R², R³ and R⁴ for a compound in each case corresponds to one line of Table A.

Table 128
Compounds of the general formula I.M where Y is CH₂S, R"$_m$ is hydrogen and the combination of the substituents R¹, R², R³ and R⁴ for a compound in each case corresponds to one line of Table A.

Table 129
Compounds of the general formula I.M where Y is CH₂NH, R"$_m$ is hydrogen and the combination of the substituents R¹, R², R³ and R⁴ for a compound in each case corresponds to one line of Table A.

Table 130
Compounds of the general formula I.M where Y is CH₂CH₂, R"$_m$ is hydrogen and the combination of the substituents R¹, R², R³ and R⁴ for a compound in each case corresponds to one line of Table A.

Table 131
Compounds of the general formula I.M where Y is CH=CH, R"$_m$ is hydrogen and the combination of the substituents R¹, R², R³ and R⁴ for a compound in each case corresponds to one line of Table A.

Table 132
Compounds of the general formula I.M where Y is C≡C, R"$_m$ is hydrogen and the combination of the substituents R¹, R², R³ and R⁴ for a compound in each case corresponds to one line of Table A.

Table 133
Compounds of the general formula I.N where Y is oxygen, R"$_m$ is hydrogen and the combination of the substituents R¹, R², R³ and R⁴ for a compound in each case corresponds to one line of Table A.

I.N

[Chemical structure of formula I.N]

Table 134
Compounds of the general formula I.N where Y is sulfur, R"$_m$ is hydrogen and the combination of the substituents R¹, R², R³ and R⁴ for a compound in each case corresponds to one line of Table A.

Table 135
Compounds of the general formula I.N where Y is —NH—, R"$_m$ is hydrogen and the combination of the substituents R¹R², R³ and R⁴ for a compound in each case corresponds to one line of Table A.

Table 136
Compounds of the general formula I.N where Y is OCH₂, R"$_m$ is hydrogen and the combination of the substituents R¹R², R³ and R⁴ for a compound in each case corresponds to one line of Table A.

Table 137
Compounds of the general formula I.N where Y is SCH₂, R"$_m$ is hydrogen and the combination of the substituents $R^1R^2$, $R^3$ and $R^4$ for a compound in each case corresponds to one line of Table A.

Table 138

Compounds of the general formula I.N where Y is $NHCH_2$, $R''_m$ is hydrogen and the combination of the substituents $R^1R^2$, $R^3$ and $R^4$ for a compound in each case corresponds to one line of Table A.

Table 139

Compounds of the general formula I.N where Y is $CH_2O$, $R''_m$ is hydrogen and the combination of the substituents $R^1$, $R^2$, $R^3$ and $R^4$ for a compound in each case corresponds to one line of Table A.

Table 140

Compounds of the general formula I.N where Y is $CH_2S$, $R''_m$ is hydrogen and the combination of the substituents $R^1R^2$, $R^3$ and $R^4$ for a compound in each case corresponds to one line of Table A.

Table 141

Compounds of the general formula I.N where Y is $CH_2NH$, $R''_m$ is hydrogen and the combination of the substituents $R^1$, $R^2$, $R^3$ and $R^4$ for a compound in each case corresponds to one line of Table A.

Table 142

Compounds of the general formula I.N where Y is $CH_2CH_2$, $R''_m$ is hydrogen and the combination of the substituents $R^1R^2$, $R^3$ and $R^4$ for a compound in each case corresponds to one line of Table A.

Table 143

Compounds of the general formula I.N where Y is $CH=CH$, $R''_m$ is hydrogen and the combination of the substituents $R^1R^2$, $R^3$ and $R^4$ for a compound in each case corresponds to one line of Table A.

Table 144

Compounds of the general formula I.N where Y is $C\equiv C$, $R''_m$ is hydrogen and the combination of the substituents $R^1R^2$, $R^3$ and $R^4$ for a compound in each case corresponds to one line of Table A.

Table 145

Compounds of the general formula I.O where Y is oxygen, $R''_m$ is hydrogen and the combination of the substituents $R^1R^2$, $R^3$ and $R^4$ for a compound in each case corresponds to one line of Table A.

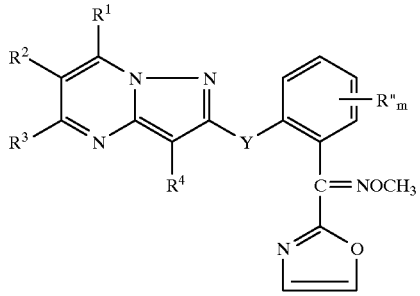

I.O

Table 146

Compounds of the general formula I.O where Y is sulfur, $R''_m$ is hydrogen and the combination of the substituents $R^1$, $R^2$, $R^3$ and $R^4$ for a compound in each case corresponds to one line of Table A.

Table 147

Compounds of the general formula I.O where Y is —NH—, $R''_m$ is hydrogen and the combination of the substituents $R^1$, $R^2$, $R^3$ and $R^4$ for a compound in each case corresponds to one line of Table A.

Table 148

Compounds of the general formula I.O where Y is $OCH_2$, $R''_m$ is hydrogen and the combination of the substituents $R^1$, $R^2$, $R^3$ and $R^4$ for a compound in each case corresponds to one line of Table A.

Table 149

Compounds of the general formula I.O where Y is $SCH_2$, $R''_m$ is hydrogen and the combination of the substituents $R^1R^2$, $R^3$ and $R^4$ for a compound in each case corresponds to one line of Table A.

Table 150

Compounds of the general formula I.O where Y is $NHCH_2$, $R''_m$ is hydrogen and the combination of the substituents $R^1$, $R^2$, $R^3$ and $R^4$ for a compound in each case corresponds to one line of Table A.

Table 151

Compounds of the general formula I.O where Y is $CH_2O$, $R''_m$ is hydrogen and the combination of the substituents $R^1$, $R^2$, $R^3$ and $R^4$ for a compound in each case corresponds to one line of Table A.

Table 152

Compounds of the general formula I.O where Y is $CH_2S$, $R''_m$ is hydrogen and the combination of the substituents $R^1$, $R^2$, $R^3$ and $R^4$ for a compound in each case corresponds to one line of Table A.

Table 153

Compounds of the general formula I.O where Y is $CH_2NH$, $R''_m$ is hydrogen and the combination of the substituents $R^1R^2$, $R^3$ and $R^4$ for a compound in each case corresponds to one line of Table A.

Table 154

Compounds of the general formula I.O where Y is $CH_2CH_2$, $R''_m$ is hydrogen and the combination of the substituents $R^1R^2$, $R^3$ and $R^4$ for a compound in each case corresponds to one line of Table A.

Table 155

Compounds of the general formula I.O where Y is $CH=CH$, $R''_m$ is hydrogen and the combination of the substituents $R^1R^2$, $R^3$ and $R^4$ for a compound in each case corresponds to one line of Table A.

Table 156

Compounds of the general formula I.O where Y is $C\equiv C$, $R''_m$ is hydrogen and the combination of the substituents $R^1$, $R^2$, $R^3$ and $R^4$ for a compound in each case corresponds to one line of Table A.

Table 6

Compounds of the general formula I.F where $R''_m$ is . . . and the combination of the substituents $R^1$, $R^2$, $R^3$ and $R^4$ for a compound in each case corresponds to one line of Table A [sic].

TABLE A

| No. | R¹ | R² | R³ | R⁴ |
|-----|-----|-----|-----|-----|
| 1 | H | H | H | H |
| 2 | CH₃ | H | H | H |
| 3 | H | CH₃ | H | H |
| 4 | H | H | CH₃ | H |
| 5 | H | H | H | CH₃ |
| 6 | CH₃ | CH₃ | H | H |
| 7 | CH₃ | H | CH₃ | H |
| 8 | CH₃ | H | H | CH₃ |
| 9 | H | CH₃ | H | CH₃ |
| 10 | H | CH₃ | CH₃ | H |
| 11 | H | H | CH₃ | CH₃ |
| 12 | CH₃ | CH₃ | CH₃ | H |
| 13 | CH₃ | CH₃ | H | CH₃ |
| 14 | CH₃ | H | CH₃ | CH₃ |
| 15 | H | CH₃ | CH₃ | CH₃ |
| 16 | CH₃ | CH₃ | CH₃ | CH₃ |
| 17 | C₂H₅ | H | H | H |
| 18 | H | C₂H₅ | H | H |
| 19 | H | H | C₂H₅ | H |
| 20 | H | H | H | C₂H₅ |
| 21 | C₂H₅ | CH₃ | H | H |
| 22 | C₂H₅ | H | CH₃ | H |
| 23 | C₂H₅ | H | H | CH₃ |
| 24 | CH₃ | C₂H₅ | H | H |
| 25 | CH₃ | H | C₂H₅ | H |
| 26 | CH₃ | H | H | C₂H₅ |
| 27 | H | C₂H₅ | H | CH₃ |
| 28 | H | C₂H₅ | CH₃ | H |
| 29 | H | H | C₂H₅ | CH₃ |
| 30 | H | H | CH₃ | C₂H₅ |
| 31 | C₂H₅ | CH₃ | CH₃ | H |
| 32 | C₂H₅ | CH₃ | H | CH₃ |
| 33 | C₂H₅ | H | CH₃ | CH₃ |
| 34 | CH₃ | C₂H₅ | CH₃ | H |
| 35 | CH₃ | C₂H₅ | H | CH₃ |
| 36 | H | C₂H₅ | CH₃ | CH₃ |
| 37 | CH₃ | H | C₂H₅ | CH₃ |
| 38 | CH₃ | CH₃ | C₂H₅ | H |
| 39 | H | CH₃ | C₂H₅ | CH₃ |
| 40 | H | CH₃ | CH₃ | C₂H₅ |
| 41 | CH₃ | H | CH₃ | C₂H₅ |
| 42 | CH₃ | CH₃ | H | C₂H₅ |
| 43 | i-C₃H₇ | CH₃ | CH₃ | H |
| 44 | i-C₃H₇ | CH₃ | H | CH₃ |
| 45 | i-C₃H₇ | H | CH₃ | CH₃ |
| 46 | CH₃ | i-C₃H₇ | CH₃ | H |
| 47 | CH₃ | i-C₃H₇ | H | CH₃ |
| 48 | H | i-C₃H₇ | CH₃ | CH₃ |
| 49 | CH₃ | H | i-C₃H₇ | CH₃ |
| 50 | CH₃ | CH₃ | i-C₃H₇ | H |
| 51 | H | CH₃ | i-C₃H₇ | CH₃ |
| 52 | H | CH₃ | CH₃ | i-C₃H₇ |
| 53 | CH₃ | H | CH₃ | i-C₃H₇ |
| 54 | CH₃ | CH₃ | H | i-C₃H₇ |
| 55 | t.-C₄H₉ | CH₃ | CH₃ | H |
| 56 | t.-C₄H₉ | CH₃ | H | CH₃ |
| 57 | t.-C₄H₉ | H | CH₃ | CH₃ |
| 58 | CH₃ | t.-C₄H₉ | CH₃ | H |
| 59 | CH₃ | t.-C₄H₉ | H | CH₃ |
| 60 | H | t.-C₄H₉ | CH₃ | CH₃ |
| 61 | CH₃ | H | t.-C₄H₉ | CH₃ |
| 62 | CH₃ | CH₃ | t.-C₄H₉ | H |
| 63 | H | CH₃ | t.-C₄H₉ | CH₃ |
| 64 | H | CH₃ | CH₃ | t.-C₄H₉ |
| 65 | CH₃ | H | CH₃ | t.-C₄H₉ |
| 66 | CH₃ | CH₃ | H | t.-C₄H₉ |
| 67 | C₂H₅ | H | H | C₂H₅ |
| 68 | C₂H₅ | H | C₂H₅ | H |
| 69 | C₂H₅ | C₂H₅ | H | H |
| 70 | H | C₂H₅ | H | C₂H₅ |
| 71 | H | C₂H₅ | C₂H₅ | H |
| 72 | H | H | C₂H₅ | C₂H₅ |
| 73 | C₂H₅ | C₂H₅ | CH₃ | H |
| 74 | C₂H₅ | C₂H₅ | H | CH₃ |
| 75 | C₂H₅ | CH₃ | C₂H₅ | H |
| 76 | C₂H₅ | CH₃ | H | C₂H₅ |
| 77 | C₂H₅ | H | C₂H₅ | CH₃ |

TABLE A-continued

| No. | R¹ | R² | R³ | R⁴ |
|---|---|---|---|---|
| 78 | C₂H₅ | H | CH₃ | C₂H₅ |
| 79 | CH₃ | C₂H₅ | C₂H₅ | H |
| 80 | CH₃ | C₂H₅ | H | C₂H₅ |
| 81 | CH₃ | H | C₂H₅ | C₂H₅ |
| 82 | CH₃ | CH₃ | C₂H₅ | C₂H₅ |
| 83 | CH₃ | C₂H₅ | CH₃ | C₂H₅ |
| 84 | CH₃ | C₂H₅ | C₂H₅ | CH₃ |
| 85 | C₂H₅ | C₂H₅ | CH₃ | CH₃ |
| 86 | C₂H₅ | CH₃ | CH₃ | C₂H₅ |
| 87 | C₂H₅ | CH₃ | C₂H₅ | CH₃ |
| 88 | Cl | H | H | H |
| 89 | H | Cl | H | H |
| 90 | H | H | Cl | H |
| 91 | H | H | H | Cl |
| 92 | Cl | Cl | H | H |
| 93 | Cl | H | Cl | H |
| 94 | Cl | H | H | Cl |
| 95 | H | Cl | Cl | H |
| 96 | H | Cl | H | Cl |
| 97 | H | H | Cl | Cl |
| 98 | CH₃ | Cl | H | H |
| 99 | CH₃ | H | Cl | H |
| 100 | CH₃ | H | H | Cl |
| 101 | H | CH₃ | Cl | H |
| 102 | H | CH₃ | H | Cl |
| 103 | H | Cl | CH₃ | H |
| 104 | H | Cl | H | CH₃ |
| 105 | H | H | Cl | CH₃ |
| 106 | H | H | CH₃ | Cl |
| 107 | Cl | CH₃ | H | H |
| 108 | Cl | H | CH₃ | H |
| 109 | Cl | H | H | CH₃ |
| 110 | Cl | CH₃ | H | CH₃ |
| 111 | Cl | H | CH₃ | CH₃ |
| 112 | Cl | CH₃ | CH₃ | H |
| 113 | CH₃ | Cl | CH₃ | H |
| 114 | CH₃ | Cl | H | CH₃ |
| 115 | CH₃ | CH₃ | H | Cl |
| 116 | CH₃ | CH₃ | Cl | H |
| 117 | CH₃ | H | CH₃ | Cl |
| 118 | CH₃ | H | Cl | CH₃ |
| 119 | H | CH₃ | CH₃ | Cl |
| 120 | H | CH₃ | Cl | CH₃ |
| 121 | H | Cl | CH₃ | CH₃ |
| 122 | Cl | H | Cl | H |
| 123 | Cl | Cl | H | H |
| 124 | Cl | H | H | Cl |
| 125 | H | Cl | Cl | H |
| 126 | H | Cl | H | Cl |
| 127 | H | H | Cl | Cl |
| 128 | CH₃ | H | Cl | Cl |
| 129 | CH₃ | Cl | H | Cl |
| 130 | CH₃ | Cl | Cl | H |
| 131 | Cl | CH₃ | Cl | H |
| 132 | Cl | CH₃ | H | Cl |
| 133 | Cl | Cl | CH₃ | H |
| 134 | Cl | Cl | H | CH₃ |
| 135 | H | Cl | Cl | CH₃ |
| 136 | H | Cl | CH₃ | Cl |
| 137 | H | CH₃ | Cl | Cl |
| 138 | CH₃ | CH₃ | Cl | Cl |
| 139 | CH₃ | Cl | CH₃ | Cl |
| 140 | CH₃ | Cl | Cl | CH₃ |
| 141 | Cl | Cl | CH₃ | CH₃ |
| 142 | Cl | CH₃ | Cl | CH₃ |
| 143 | Cl | CH₃ | CH₃ | Cl |
| 144 | Cl | Cl | Cl | CH₃ |
| 145 | Cl | Cl | CH₃ | Cl |
| 146 | Cl | CH₃ | Cl | Cl |
| 147 | CH₃ | Cl | Cl | Cl |
| 148 | C₂H₅ | H | Cl | Cl |
| 149 | C₂H₅ | Cl | H | Cl |
| 150 | C₂H₅ | Cl | Cl | H |
| 151 | Cl | C₂H₅ | Cl | H |
| 152 | Cl | C₂H₅ | H | Cl |
| 153 | Cl | Cl | C₂H₅ | H |
| 154 | Cl | Cl | H | C₂H₅ |

TABLE A-continued

| No. | R¹ | R² | R³ | R⁴ |
|---|---|---|---|---|
| 155 | H | Cl | Cl | C₂H₅ |
| 156 | H | Cl | C₂H₅ | Cl |
| 157 | H | C₂H₅ | Cl | Cl |
| 158 | OCH₃ | H | H | H |
| 159 | H | OCH₃ | H | H |
| 160 | H | H | OCH₃ | H |
| 161 | H | H | H | OCH₃ |
| 162 | OC₂H₅ | H | H | H |
| 163 | H | OC₂H₅ | H | H |
| 164 | H | H | OC₂H₅ | H |
| 165 | H | H | H | OC₂H₅ |
| 166 | OCH₃ | CH₃ | H | H |
| 167 | OCH₃ | H | CH₃ | H |
| 168 | OCH₃ | H | H | CH₃ |
| 169 | CH₃ | OCH₃ | H | H |
| 170 | CH₃ | H | OCH₃ | H |
| 171 | CH₃ | H | H | OCH₃ |
| 172 | H | H | OCH₃ | CH₃ |
| 173 | H | H | CH₃ | OCH₃ |
| 174 | H | OCH₃ | H | CH₃ |
| 175 | H | OCH₃ | CH₃ | H |
| 176 | H | CH₃ | OCH₃ | H |
| 177 | H | CH₃ | H | OCH₃ |
| 178 | OCH₃ | OCH₃ | H | H |
| 179 | OCH₃ | H | OCH₃ | H |
| 180 | OCH₃ | H | H | OCH₃ |
| 181 | H | OCH₃ | OCH₃ | H |
| 182 | H | OCH₃ | H | OCH₃ |
| 183 | H | H | OCH₃ | OCH₃ |
| 184 | CH₃ | H | OCH₃ | OCH₃ |
| 185 | CH₃ | OCH₃ | H | OCH₃ |
| 186 | CH₃ | OCH₃ | OCH₃ | H |
| 187 | OCH₃ | CH₃ | OCH₃ | H |
| 188 | OCH₃ | CH₃ | H | OCH₃ |
| 189 | OCH₃ | OCH₃ | H | CH₃ |
| 190 | OCH₃ | OCH₃ | CH₃ | H |
| 191 | OCH₃ | H | OCH₃ | CH₃ |
| 192 | OCH₃ | H | CH₃ | OCH₃ |
| 193 | H | OCH₃ | OCH₃ | CH₃ |
| 194 | H | OCH₃ | CH₃ | OCH₃ |
| 195 | H | CH₃ | OCH₃ | OCH₃ |
| 196 | CH₃ | OCH₃ | OCH₃ | CH₃ |
| 197 | CH₃ | OCH₃ | CH₃ | OCH₃ |
| 198 | CH₃ | CH₃ | OCH₃ | OCH₃ |
| 199 | OCH₃ | OCH₃ | CH₃ | CH₃ |
| 200 | OCH₃ | CH₃ | OCH₃ | CH₃ |
| 201 | OCH₃ | CH₃ | CH₃ | OCH₃ |
| 202 | OCH₃ | Cl | CH₃ | CH₃ |
| 203 | OCH₃ | CH₃ | Cl | CH₃ |
| 204 | OCH₃ | CH₃ | CH₃ | Cl |
| 205 | Cl | CH₃ | CH₃ | OCH₃ |
| 206 | Cl | CH₃ | OCH₃ | CH₃ |
| 207 | Cl | OCH₃ | CH₃ | CH₃ |
| 208 | CH₃ | Cl | CH₃ | OCH₃ |
| 209 | CH₃ | Cl | OCH₃ | CH₃ |
| 210 | CH₃ | CH₃ | Cl | OCH₃ |
| 211 | CH₃ | CH₃ | OCH₃ | Cl |
| 212 | CH₃ | OCH₃ | CH₃ | Cl |
| 213 | CH₃ | OCH₃ | Cl | CH₃ |
| 214 | OC₂H₅ | Cl | CH₃ | CH₃ |
| 215 | OC₂H₅ | CH₃ | Cl | CH₃ |
| 216 | OC₂H₅ | CH₃ | CH₃ | Cl |
| 217 | Cl | CH₃ | CH₃ | OC₂H₅ |
| 218 | Cl | CH₃ | OC₂H₅ | CH₃ |
| 219 | Cl | OC₂H₅ | CH₃ | CH₃ |
| 220 | CH₃ | Cl | CH₃ | OC₂H₅ |
| 221 | CH₃ | Cl | OC₂H₅ | CH₃ |
| 222 | CH₃ | CH₃ | Cl | OC₂H₅ |
| 223 | CH₃ | CH₃ | OC₂H₅ | Cl |
| 224 | CH₃ | OEt | CH₃ | Cl |
| 225 | CH₃ | OEt | Cl | CH₃ |
| 226 | OC₆H₅ | H | H | H |
| 227 | H | OC₆H₅ | H | H |
| 228 | H | H | OC₆H₅ | H |
| 229 | H | H | H | OC₆H₅ |
| 230 | CH₃ | CH₃ | CH₃ | OC₆H₅ |
| 231 | CH₃ | CH₃ | OC₆H₅ | CH₃ |

TABLE A-continued

| No. | R¹ | R² | R³ | R⁴ |
|---|---|---|---|---|
| 232 | CH₃ | OC₆H₅ | CH₃ | CH₃ |
| 233 | OC₆H₅ | CH₃ | CH₃ | CH₃ |
| 234 | OC₆H₅ | CH₃ | CH₃ | OC₆H₅ |
| 235 | OC₆H₅ | CH₃ | OC₆H₅ | CH₃ |
| 236 | OC₆H₅ | OC₆H₅ | CH₃ | CH₃ |
| 237 | CH₃ | OC₆H₅ | OC₆H₅ | CH₃ |
| 238 | CH₃ | OC₆H₅ | CH₃ | OC₆H₅ |
| 239 | CH₃ | CH₃ | OC₆H₅ | OC₆H₅ |
| 240 | OCH₂CH₂CH₃ | CH₃ | CH₃ | CH₃ |
| 241 | Br | CH₃ | H | H |
| 242 | Br | H | CH₃ | H |
| 243 | Br | H | H | CH₃ |
| 244 | H | H | Br | CH₃ |
| 245 | H | H | CH₃ | Br |
| 246 | H | Br | CH₃ | H |
| 247 | H | Br | H | CH₃ |
| 248 | CH₃ | H | H | Br |
| 249 | CH₃ | H | Br | H |
| 250 | CH₃ | Br | H | H |
| 251 | Br | CH₃ | CH₃ | Br |
| 252 | Br | CH₃ | Br | CH₃ |
| 253 | Br | Br | CH₃ | CH₃ |
| 254 | CH₃ | Br | CH₃ | Br |
| 255 | CH₃ | Br | Br | CH₃ |
| 256 | CH₃ | CH₃ | Br | Br |
| 257 | F | CH₃ | CH₃ | F |
| 258 | F | CH₃ | F | CH₃ |
| 259 | F | F | CH₃ | CH₃ |
| 260 | CH₃ | CH₃ | F | F |
| 261 | CH₃ | F | CH₃ | F |
| 262 | CH₃ | F | F | CH₃ |
| 263 | CH₃ | CH₃ | OH | OH |
| 264 | CH₃ | OH | CH₃ | OH |
| 265 | CH₃ | OH | OH | CH₃ |
| 266 | OH | OH | CH₃ | CH₃ |
| 267 | OH | CH₃ | OH | CH₃ |
| 268 | OH | CH₃ | CH₃ | OH |
| 269 | CH₃ | CH₃ | OCH(CH₃)₂ | OCH(CH₃)₂ |
| 270 | CH₃ | OCH(CH₃)₂ | OCH(CH₃)₂ | CH₃ |
| 271 | CH₃ | OCH(CH₃)₂ | CH₃ | OCH(CH₃)₂ |
| 272 | OCH(CH₃)₂ | OCH(CH₃)₂ | CH₃ | CH₃ |
| 273 | OCH(CH₃)₂ | CH₃ | OCH(CH₃)₂ | CH₃ |
| 274 | OCH(CH₃)₂ | CH₃ | CH₃ | OCH(CH₃)₂ |
| 275 | CH₃ | CH₃ | OCH(CH₃)₂ | OCH₂C₆H₅ |
| 276 | CH₃ | OCH₂C₆H₅ | CH₃ | OCH₂C₆H₅ |
| 277 | CH₃ | OCH₂C₆H₅ | OCH₂C₆H₅ | CH₃ |
| 278 | OCH₂C₆H₅ | OCH₂C₆H₅ | CH₃ | CH₃ |
| 279 | OCH₂C₆H₅ | CH₃ | OCH₂C₆H₅ | CH₃ |
| 280 | OCH₂C₆H₅ | CH₃ | CH₃ | OCH₂C₆H₅ |
| 281 | CH₃ | CH₃ | OCOCH₃ | OCOCH₃ |
| 282 | CH₃ | OCOCH₃ | OCOCH₃ | CH₃ |
| 283 | CH₃ | OCOCH₃ | CH₃ | OCOCH₃ |
| 284 | OCOCH₃ | CH₃ | CH₃ | OCOCH₃ |
| 285 | OCOCH₃ | OAc | CH₃ | CH₃ |
| 286 | OCOCH₃ | CH₃ | OAC | CH₃ |
| 287 | CF₃ | CH₃ | H | H |
| 288 | CF₃ | H | H | CH₃ |
| 289 | CF₃ | H | CH₃ | H |
| 290 | H | CF₃ | H | CH₃ |
| 291 | H | CF₃ | CH₃ | H |
| 292 | H | H | CH₃ | CF₃ |
| 293 | H | H | CF₃ | CH₃ |
| 294 | CH₃ | CF₃ | H | H |
| 295 | CH₃ | H | CF₃ | H |
| 296 | CH₃ | H | H | CF₃ |
| 297 | CF₃ | H | H | H |
| 298 | H | CF₃ | H | H |
| 299 | H | H | CF₃ | H |
| 300 | H | H | H | CF₃ |
| 301 | CF₃ | CH₃ | CH₃ | H |
| 302 | CF₃ | CH₃ | H | CH₃ |
| 303 | CF₃ | H | CH₃ | CH₃ |
| 304 | H | CF₃ | CH₃ | CH₃ |
| 305 | H | CH₃ | CF₃ | CH₃ |
| 306 | H | CH₃ | CH₃ | CF₃ |
| 307 | CH₃ | CH₃ | CF₃ | H |
| 308 | CH₃ | CH₃ | H | CF₃ |

TABLE A-continued

| No. | R¹ | R² | R³ | R⁴ |
|---|---|---|---|---|
| 309 | CH₃ | CF₃ | CH₃ | H |
| 310 | CH₃ | CF₃ | H | CH₃ |
| 311 | CH₃ | H | CF₃ | CH₃ |
| 312 | CH₃ | H | CH₃ | CF₃ |
| 313 | CF₃ | CH₃ | CH₃ | CH₃ |
| 314 | CH₃ | CF₃ | CH₃ | CH₃ |
| 315 | CH₃ | CH₃ | CF₃ | CH₃ |
| 316 | CH₃ | CH₃ | CH₃ | CF₃ |
| 317 | CF₃ | CF₃ | H | H |
| 318 | CF₃ | H | CF₃ | H |
| 319 | CF₃ | H | H | CF₃ |
| 320 | H | CF₃ | H | CF₃ |
| 321 | H | H | CF₃ | CF₃ |
| 322 | H | CF₃ | CF₃ | H |
| 323 | CF₃ | CF₃ | CH₃ | H |
| 324 | CF₃ | CF₃ | H | CH₃ |
| 325 | CF₃ | H | CH₃ | CF₃ |
| 326 | CF₃ | H | CF₃ | CF₃ |
| 327 | CF₃ | CH₃ | H | CF₃ |
| 328 | CF₃ | CH₃ | CF₃ | H |
| 329 | CH₃ | CF₃ | CF₃ | H |
| 330 | CH₃ | CF₃ | H | CF₃ |
| 331 | CH₃ | H | CF₃ | CF₃ |
| 332 | H | CH₃ | CF₃ | CF₃ |
| 333 | H | CF₃ | CH₃ | CF₃ |
| 334 | H | CF₃ | CF₃ | CH₃ |
| 335 | CF₃ | CF₃ | CH₃ | CH₃ |
| 336 | CF₃ | CH₃ | CF₃ | CH₃ |
| 337 | CF₃ | CH₃ | CH₃ | CF₃ |
| 338 | CH₃ | CH₃ | CF₃ | CF₃ |
| 339 | CH₃ | CF₃ | CH₃ | CF₃ |
| 340 | CH₃ | CF₃ | CF₃ | CH₃ |
| 341 | CF₃ | CF₃ | CF₃ | H |
| 342 | CF₃ | CF₃ | H | CF₃ |
| 343 | CF₃ | H | CF₃ | CF₃ |
| 344 | H | CF₃ | CF₃ | CF₃ |
| 345 | CF₃ | CF₃ | CF₃ | CH₃ |
| 346 | CF₃ | CF₃ | CH₃ | CF₃ |
| 347 | CF₃ | CH₃ | CF₃ | CF₃ |
| 348 | CH₃ | CF₃ | CF₃ | CF₃ |
| 349 | CCl₃ | H | H | H |
| 350 | H | CCl₃ | H | H |
| 351 | H | H | CCl₃ | H |
| 352 | H | H | H | CCl₃ |
| 353 | CCl₃ | CH₃ | H | H |
| 354 | CCl₃ | H | CH₃ | H |
| 355 | CCl₃ | H | H | CH₃ |
| 356 | CH₃ | CCl₃ | H | H |
| 357 | CH₃ | H | CCl₃ | H |
| 358 | CH₃ | H | H | CCl₃ |
| 359 | H | H | CH₃ | CCO₃ |
| 360 | H | H | CCl₃ | CH₃ |
| 361 | H | CH₃ | CCl₃ | H |
| 362 | H | CH₃ | H | CCl₃ |
| 363 | H | CCl₃ | H | CH₃ |
| 364 | H | CCl₃ | CH₃ | H |
| 365 | C₆H₅ | H | H | H |
| 366 | H | C₆H₅ | H | H |
| 367 | H | H | C₆H₅ | H |
| 368 | H | H | H | C₆H₅ |
| 369 | C₆H₅ | CH₃ | H | H |
| 370 | C₆H₅ | H | CH₃ | H |
| 371 | C₆H₅ | H | H | CH₃ |
| 372 | CH₃ | C₆H₅ | H | H |
| 373 | CH₃ | H | C₆H₅ | H |
| 374 | CH₃ | H | H | C₆H₅ |
| 375 | H | CH₃ | H | C₆H₅ |
| 376 | H | CH₃ | C₆H₅ | H |
| 377 | H | H | CH₃ | C₆H₅ |
| 378 | H | H | C₆H₅ | CH₃ |
| 379 | H | C₆H₅ | CH₃ | H |
| 380 | H | C₆H₅ | H | CH₃ |
| 381 | C₆H₅ | H | CH₃ | CH₃ |
| 382 | C₆H₅ | CH₃ | H | CH₃ |
| 383 | C₆H₅ | CH₃ | CH₃ | H |
| 384 | H | C₆H₅ | CH₃ | CH₃ |
| 385 | H | CH₃ | C₆H₅ | CH₃ |

TABLE A-continued

| No. | R¹ | R² | R³ | R⁴ |
|---|---|---|---|---|
| 386 | H | CH₃ | CH₃ | C₆H₅ |
| 387 | CH₃ | H | C₆H₅ | CH₃ |
| 388 | CH₃ | H | CH₃ | C₆H₅ |
| 389 | CH₃ | C₆H₅ | CH₃ | H |
| 390 | CH₃ | C₆H₅ | H | CH₃ |
| 391 | CH₃ | CH₃ | H | C₆H₅ |
| 392 | CH₃ | CH₃ | C₆H₅ | H |
| 393 | CH₃ | CH₃ | CH₃ | C₆H₅ |
| 394 | CH₃ | CH₃ | Ph | CH₃ |
| 395 | CH₃ | Ph | CH₃ | CH₃ |
| 396 | Ph | CH₃ | CH₃ | CH₃ |
| 397 | 2-Pyridyl | CH₃ | CH₃ | H |
| 398 | 2-Pyridyl | CH₃ | H | CH₃ |
| 399 | 2-Pyridyl | H | CH₃ | CH₃ |
| 400 | H | 2-Pyridyl | CH₃ | CH₃ |
| 401 | H | CH₃ | 2-Pyridyl | CH₃ |
| 402 | H | CH₃ | CH₃ | 2-Pyridyl |
| 403 | CH₃ | 2-Pyridyl | H | CH₃ |
| 404 | CH₃ | 2-Pyridyl | CH₃ | H |
| 405 | CH₃ | CH₃ | 2-Pyridyl | H |
| 406 | CH₃ | H | 2-Pyridyl | CH₃ |
| 407 | CH₃ | CH₃ | H | 2-Pyridyl |
| 408 | CH₃ | H | CH₃ | 2-Pyridyl |
| 409 | 3-Pyridyl | CH₃ | CH₃ | H |
| 410 | 3-Pyridyl | CH₃ | H | CH₃ |
| 411 | 3-Pyridyl | H | CH₃ | CH₃ |
| 412 | H | 3-Pyridyl | CH₃ | CH₃ |
| 413 | H | CH₃ | 3-Pyridyl | CH₃ |
| 414 | H | CH₃ | CH₃ | 3-Pyridyl |
| 415 | CH₃ | 3-Pyridyl | H | CH₃ |
| 416 | CH₃ | 3-Pyridyl | CH₃ | H |
| 417 | CH₃ | CH₃ | 3-Pyridyl | H |
| 418 | CH₃ | H | 3-Pyridyl | CH₃ |
| 419 | CH₃ | CH₃ | H | 3-Pyridyl |
| 420 | CH₃ | H | CH₃ | 3-Pyridyl |
| 421 | 4-Pyridyl | CH₃ | CH₃ | H |
| 422 | 4-Pyridyl | CH₃ | H | CH₃ |
| 423 | 4-Pyridyl | H | CH₃ | CH₃ |
| 424 | H | 4-Pyridyl | CH₃ | CH₃ |
| 425 | H | CH₃ | 4-Pyridyl | CH₃ |
| 426 | H | CH₃ | CH₃ | 4-Pyridyl |
| 427 | CH₃ | 4-Pyridyl | H | CH₃ |
| 428 | CH₃ | 4-Pyridyl | CH₃ | H |
| 429 | CH₃ | CH₃ | 4-Pyridyl | H |
| 430 | CH₃ | H | 4-Pyridyl | CH₃ |
| 431 | CH₃ | CH₃ | H | 4-Pyridyl |
| 432 | CH₃ | H | CH₃ | 4-Pyridyl |
| 433 | CH₂C₆H₅ | H | H | H |
| 434 | H | CH₂C₆H₅ | H | H |
| 435 | H | H | CH₂C₆H₅ | H |
| 436 | H | H | H | CH₂C₆H₅ |
| 437 | CH₂CH=CH₂ | H | H | H |
| 438 | H | CH₂CH=CH₂ | H | H |
| 439 | H | H | CH₂CH=CH₂ | H |
| 440 | H | H | H | CH₂CH=CH₂ |
| 441 | N(CH₃)₂ | H | H | H |
| 442 | H | N(CH₃)₂ | H | H |
| 443 | H | H | N(CH₃)₂ | H |
| 444 | H | H | H | N(CH₃)₂ |
| 445 | N(CH₃)₂ | CH₃ | CH₃ | CH₃ |
| 446 | CH₃ | N(CH₃)₂ | CH₃ | CH₃ |
| 447 | CH₃ | CH₃ | N(CH₃)₂ | CH₃ |
| 448 | CH₃ | CH₃ | CH₃ | N(CH₃)₂ |
| 449 | NO₂ | CH₃ | CH₃ | CH₃ |
| 450 | CH₃ | NO₂ | CH₃ | CH₃ |
| 451 | CH₃ | CH₃ | NO₂ | CH₃ |
| 452 | CH₃ | CH₃ | CH₃ | NO₂ |
| 453 | CH₃ | CH₃ | SCH₃ | SCH₃ |
| 454 | CH₃ | SCH₃ | CH₃ | SCH₃ |
| 455 | CH₃ | SCH₃ | SCH₃ | CH₃ |
| 456 | SCH₃ | SCH₃ | CH₃ | CH₃ |
| 457 | SCH₃ | CH₃ | SCH₃ | CH₃ |
| 458 | SCH₃ | CH₃ | CH₃ | SCH₃ |
| 459 | COOMe | CH₃ | CH₃ | CH₃ |
| 460 | CH₃ | COOCH₃ | CH₃ | CH₃ |
| 461 | CH₃ | CH₃ | COOCH₃ | CH₃ |
| 462 | CH₃ | CH₃ | CH₃ | COOCH₃ |

TABLE A-continued

| No. | R¹ | R² | R³ | R⁴ |
|---|---|---|---|---|
| 463 | COOCH₃ | H | CH₃ | CH₃ |
| 464 | COOCH₃ | CH₃ | H | CH₃ |
| 465 | COOCH₃ | CH₃ | CH₃ | H |
| 466 | H | COOCH₃ | CH₃ | CH₃ |
| 467 | H | CH₃ | COOCH₃ | CH₃ |
| 468 | H | CH₃ | CH₃ | COOMe |
| 469 | CH₃ | CH₃ | COOCH₃ | H |
| 470 | CH₃ | CH₃ | H | COOCH₃ |
| 471 | CH₃ | H | CH₃ | COOCH₃ |
| 472 | CH₃ | COOCH₃ | CH₃ | H |
| 473 | CH₃ | COOCH₃ | H | CH₃ |
| 474 | CH₃ | H | COOCH₃ | CH₃ |
| 475 | COCH₃ | H | H | H |
| 476 | H | COCH₃ | H | H |
| 477 | H | H | COCH₃ | H |
| 478 | H | H | H | COCH₃ |
| 479 | COCH₃ | CH₃ | CH₃ | CH₃ |
| 480 | CH₃ | COCH₃ | CH₃ | CH₃ |
| 481 | CH₃ | CH₃ | COCH₃ | CH₃ |
| 482 | CH₃ | CH₃ | CH₃ | COCH₃ |
| 483 | CHO | CH₃ | CH₃ | CH₃ |
| 484 | CH₃ | CHO | CH₃ | CH₃ |
| 485 | CH₃ | CH₃ | CHO | CH₃ |
| 486 | CH₃ | CH₃ | CH₃ | CHO |
| 487 | C(CH₃)N=OCH₃ | CH₃ | CH₃ | CH₃ |
| 488 | CH₃ | C(CH₃)N=OCH₃ | CH₃ | CH₃ |
| 489 | CH₃ | CH₃ | C(CH₃)N=OCH₃ | CH₃ |
| 490 | CH₃ | CH₃ | CH₃ | C(CH₃)N=OCH₃ |
| 491 | CN | CH₃ | CH₃ | CH₃ |
| 492 | CH₃ | CN | CH₃ | CH₃ |
| 493 | CH₃ | CH₃ | CN | CH₃ |
| 494 | CH₃ | CH₃ | CH₃ | CN |
| 495 | CN | H | H | H |
| 496 | H | CN | H | H |
| 497 | H | H | CN | H |
| 498 | H | H | H | CN |
| 499 | CH₃ | H | Ph | C₂H₅ |
| 500 | CH₃ | H | CF₃ | C₂H₅ |
| 501 | CF₃ | H | CH₃ | C₂H₅ |
| 502 | CH₃ | CH₃ | CH₃ | C₂H₅ |
| 503 | CH₃ | CO₂CH₃ | CH₃ | C₂H₅ |
| 504 | C₂H₅ | H | C₂H₅ | C₂H₅ |
| 505 | C₂H₅ | H | C₂H₅ | CF₃ |
| 506 | C₂H₅ | H | C₂H₅ | Cl |
| 507 | C₂H₅ | H | CH(CH₃)₂ | H |
| 508 | C₂H₅ | H | CH(CH₃)₂ | CH₃ |
| 509 | C₂H₅ | H | CH(CH₃)₂ | CF₃ |
| 510 | C₂H₅ | H | CH(CH₃)₂ | Cl |
| 511 | C₂H₅ | H | C(CH₃)₃ | H |
| 512 | C₂H₅ | H | C(CH₃)₃ | CH₃ |
| 513 | C₂H₅ | H | C(CH₃)₃ | CF₃ |
| 514 | C₂H₅ | H | C(CH₃)₃ | Cl |
| 515 | C₂H₅ | H | cyclopropyl | H |
| 516 | C₂H₅ | H | cyclopropyl | CH₃ |
| 517 | C₂H₅ | H | cyclopropyl | CF₃ |
| 518 | C₂H₅ | H | cyclopropyl | Cl |
| 519 | C₂H₅ | H | CF₃ | H |
| 520 | C₂H₅ | H | CF₃ | CH₃ |
| 521 | C₂H₅ | H | CF₃ | CF₃ |
| 522 | C₂H₅ | H | CF₃ | Cl |
| 523 | CH(CH₃)₂ | H | C₂H₅ | H |
| 524 | CH(CH₃)₂ | H | C₂H₅ | CH₃ |
| 525 | CH(CH₃)₂ | H | C₂H₅ | CF₃ |
| 526 | CH(CH₃)₂ | H | C₂H₅ | Cl |
| 527 | CH(CH₃)₂ | H | CH(CH₃)₂ | H |
| 528 | CH(CH₃)₂ | H | CH(CH₃)₂ | CH₃ |
| 529 | CH(CH₃)₂ | H | CH(CH₃)₂ | CF₃ |
| 530 | CH(CH₃)₂ | H | CH(CH₃)₂ | Cl |
| 531 | CH(CH₃)₂ | H | C(CH₃)₃ | H |
| 532 | CH(CH₃)₂ | H | C(CH₃)₃ | CH₃ |
| 533 | CH(CH₃)₂ | H | C(CH₃)₃ | CF₃ |
| 534 | CH(CH₃)₂ | H | C(CH₃)₃ | Cl |
| 535 | CH(CH₃)₂ | H | cyclopropyl | H |
| 536 | CH(CH₃)₂ | H | cyclopropyl | CH₃ |
| 537 | CH(CH₃)₂ | H | cyclopropyl | CF₃ |
| 538 | CH(CH₃)₂ | H | cyclopropyl | Cl |
| 539 | CH(CH₃)₂ | H | CF₃ | H |

TABLE A-continued

| No. | $R^1$ | $R^2$ | $R^3$ | $R^4$ |
|---|---|---|---|---|
| 540 | $CH(CH_3)_2$ | H | $CF_3$ | $CH_3$ |
| 541 | $CH(CH_3)_2$ | H | $CF_3$ | $CF_3$ |
| 542 | $CH(CH_3)_2$ | H | $CF_3$ | Cl |
| 543 | cyclopropyl | H | $C_2H_5$ | H |
| 544 | cyclopropyl | H | $C_2H_5$ | $CH_3$ |
| 545 | cyclopropyl | H | $C_2H_5$ | $CF_3$ |
| 546 | cyclopropyl | H | $C_2H_5$ | Cl |
| 547 | cyclopropyl | H | $CH(CH_3)_2$ | H |
| 548 | cyclopropyl | H | $CH(CH_3)_2$ | $CH_3$ |
| 549 | cyclopropyl | H | $CH(CH_3)_2$ | $CF_3$ |
| 550 | cyclopropyl | H | $CH(CH_3)_2$ | Cl |
| 551 | cyclopropyl | H | $C(CH_3)_3$ | H |
| 552 | cyclopropyl | H | $C(CH_3)_3$ | $CH_3$ |
| 553 | cyclopropyl | H | $C(CH_3)_3$ | $CF_3$ |
| 554 | cyclopropyl | H | $C(CH_3)_3$ | Cl |
| 555 | cyclopropyl | H | cyclopropyl | H |
| 556 | cyclopropyl | H | cyclopropyl | $CH_3$ |
| 557 | cyclopropyl | H | cyclopropyl | $CF_3$ |
| 558 | cyclopropyl | H | cyclopropyl | Cl |
| 559 | cyclopropyl | H | $CF_3$ | H |
| 560 | cyclopropyl | H | $CF_3$ | $CH_3$ |
| 561 | cyclopropyl | H | $CF_3$ | $CF_3$ |
| 562 | cyclopropyl | H | $CF_3$ | Cl |
| 563 | $C(CH_3)_3$ | H | $C_2H_5$ | H |
| 564 | $C(CH_3)_3$ | H | $C_2H_5$ | $CH_3$ |
| 565 | $C(CH_3)_3$ | H | $C_2H_5$ | $CF_3$ |
| 566 | $C(CH_3)_3$ | H | $C_2H_5$ | Cl |
| 567 | $C(CH_3)_3$ | H | $CH(CH_3)_2$ | H |
| 568 | $C(CH_3)_3$ | H | $CH(CH_3)_2$ | $CH_3$ |
| 569 | $C(CH_3)_3$ | H | $CH(CH_3)_2$ | $CF_3$ |
| 570 | $C(CH_3)_3$ | H | $CH(CH_3)_2$ | Cl |
| 571 | $C(CH_3)_3$ | H | $C(CH_3)_3$ | H |
| 572 | $C(CH_3)_3$ | H | $C(CH_3)_3$ | $CH_3$ |
| 573 | $C(CH_3)_3$ | H | $C(CH_3)_3$ | $CF_3$ |
| 574 | $C(CH_3)_3$ | H | $C(CH_3)_3$ | Cl |
| 575 | $C(CH_3)_3$ | H | cyclopropyl | H |
| 576 | $C(CH_3)_3$ | H | cyclopropyl | $CH_3$ |
| 577 | $C(CH_3)_3$ | H | cyclopropyl | $CF_3$ |
| 578 | $C(CH_3)_3$ | H | cyclopropyl | Cl |
| 579 | $C(CH_3)_3$ | H | $CF_3$ | H |
| 580 | $C(CH_3)_3$ | H | $CF_3$ | $CH_3$ |
| 581 | $C(CH_3)_3$ | H | $CF_3$ | $CF_3$ |
| 582 | $C(CH_3)_3$ | H | $CF_3$ | Cl |
| 583 | $CF_3$ | H | $C_2H_5$ | H |
| 584 | $CF_3$ | H | $C_2H_5$ | $CH_3$ |
| 585 | $CF_3$ | H | $C_2H_5$ | $CF_3$ |
| 586 | $CF_3$ | H | $C_2H_5$ | Cl |
| 587 | $CF_3$ | H | $CH(CH_3)_2$ | H |
| 588 | $CF_3$ | H | $CH(CH_3)_2$ | $CH_3$ |
| 589 | $CF_3$ | H | $CH(CH_3)_2$ | $CF_3$ |
| 590 | $CF_3$ | H | $CH(CH_3)_2$ | Cl |
| 591 | $CF_3$ | H | $C(CH_3)_3$ | H |
| 592 | $CF_3$ | H | $C(CH_3)_3$ | $CH_3$ |
| 593 | $CF_3$ | H | $C(CH_3)_3$ | $CF_3$ |
| 594 | $CF_3$ | H | $C(CH_3)_3$ | Cl |
| 595 | $CF_3$ | H | cyclopropyl | H |
| 596 | $CF_3$ | H | cyclopropyl | $CH_3$ |
| 597 | $CF_3$ | H | cyclopropyl | $CF_3$ |
| 598 | $CF_3$ | H | cyclopropyl | Cl |
| 599 | $CF_3$ | H | $CF_3$ | H |
| 600 | $CF_3$ | H | $CF_3$ | $CH_3$ |
| 601 | $CF_3$ | H | $CF_3$ | $CF_3$ |
| 602 | $CF_3$ | H | $CF_3$ | Cl |

The compounds of the formula I according to the invention are suitable for controlling harmful fungi and animal pests of the insects, arachnids and nematodes class. They can be employed as funcicides and pesticides in the crop protection and in the hygiene, stored material protection and veterinary sector.

The harmful insects include:
  from the order of the butterflies (Lepidoptera), for example, Adoxophyes orana, Agrotis ypsilon, Agrotis segetum, Alabama arguillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphnia nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantreia monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia, Tryporyza incertulas, Zeiraphera canadensis, also Galleria mellonella and Sitotroga cerealella, Ephestia cautella, Tineola bisselliella;

from the order of the beetles (Coleoptera), for example, Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, diabrotica longicornis, diabrotica 12-punctata, diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus [sic] sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus, also Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;

from the order of the dipterous insects (Diptera), for example, Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa, also Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina [sic], Lucilia cuprina, Lucilia sericata, Musca domestica, Muscina stabulans, Oestrus ovis, Tabanus bovinus, Simulium damnosum;

from the order of the thrips (Thysanoptera), for example, Frankliniella fusca, Frankliniella occidentalis, Frankliniella tritici, Haplothrips tritici, Scirtothrips citri, Thrips oryzae, Thrips palmi, Thrips tabaci;

from the order of the hymenopterous insects (Hymenoptera), for example, Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the bed bugs (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the plant-sucking insects (Homoptera), for example, Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example, Calotermes flavicollis, Leucotermes flavipes, Macrotermes subhyalinus, Odontotermes formosanus, Reticulitermes lucifugus, Termes natalensis;

from the order of the orthopterous insects (Orthoptera), for example, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, also Acheta domestica, Blatta orientalis, Blattella germanica, Periplaneta americana;

from the order of the Arachnoidea, for example, phytophagous mites such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi and animalparasitic mites such as *Dermanyssus gallinae, Psoroptes ovis* and *Sarcoptes scabiei;* from the class of the nematodes, for example, root gall nematodes, eg. *Meloidogyne hapla, Meloidogyne incognita, Meloidogyne javanica*, cyst-forming nematodes, eg. *Globodera pallida, Globodera rostochiensis, Heterodera avenae, Heterodera glycines, Heterodera schachtii*, migratory endoparasites and semi-ndoparasitic nematodes, eg. *Heliocotylenchus multicinctus, Hirschmanniella oryzae,* Hoplolaimus spp, *Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans*, stem and leaf nematodes, eg. *Anguina tritici, Aphelenchoides besseyi, ditylenchus angustus, ditylenchus dipsaci*, virus vectors, eg. Longidorus spp, *Trichodorus christei, Trichodorus viruliferus, Xiphinema index, Xiphinema mediterraneum.*

The active compounds can be used as such, in the form of their formulations or the use forms prepared therefrom by spraying, atomizing, dusting, broadcasting or watering, eg. in the form of directly sprayable solutions, powders, suspensions or dispersions, emulsions, oil dispersions, pastes, dusting compositions, broadcasting compositions or granules. The use forms depend entirely on the intended uses; in each case they should if possible guarantee the finest dispersion of the active compounds according to the invention.

The compounds of the formula I are in some cases systemically active as fungicides. They can be employed as folia and soil fungicides against a broad spectrum of phytopathogenic fungi, in particular from the Ascomycetes, Deuteromycetes, Phycomycetes and Basidiomycetes classes.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for the control of the following plant diseases:
*Erysiphe graminis* (powdery mildew) in cereals,
*Erysiphe cichoracearum* and *Sphaerotheca fuliginea* on cucurbits,
*Podosphaera leucotricha* on apples,
*Uncinula necator* on vines,
Puccinia species on cereals,
Rhizoctonia species on cotton and grass,
Ustilago species on cereals and sugar cane,
*Venturia inaequalis* (scab) on apples,
Helminthosporium species on cereals,
*Septoria nodorum* on wheat,
*Botrytis cinerea* (gray mold) on strawberries, vines,
*Cercospora arachidicola* on groundnuts,
*Pseudocercosporella herpotrichoides* on wheat, barley,
*Pyricularia oryzae* on rice,
Phytophthora infestans on potatoes and tomatoes,
Fusarium and Verticillium species on various plants,
Plasmopara viticola on vines,
Alternaria species on vegetables and fruit.

The novel compounds can also be employed in the protection of materials (preservation of wood), eg. against *Paecilomyces variotii.*

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:
solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;
carriers such as ground natural minerals (eg. kaolins, aluminas, talc, chalk) and ground synthetic minerals (eg. highly disperse silica, silicates);
emulsifiers such as nonionic and anionic emulsifiers (eg. polyoxyethylene fatty alcohol ethers, alkylsulfonates and arylsulfonates) and
dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol [sic] ether, ethoxylated isooctyl-, octyl- or nonylphenol, alkylphenol [sic] or tributylphenylpolyglycol ethers, alkylaryl polyether alcohols, isotridecyl alcohol, fatty alcohol ethylene oxide condensates, ethoxylated castor oil, polyoxyethylene alkyl ethers or polyoxypropylene [sic], lauryl alcohol polyglycol ether acetate, sorbitol esters, lignin-sulfite waste liquors or methylcellulose.

Aqueous use forms can be prepared from emulsion concentrates, dispersions, pastes, wettable powders or water-dispersible granules by addition of water. To prepare emulsions, pastes or oil dispersions, the substrates [sic] can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silica gels [sic], silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, of active compound are suitable.

The active compounds are normally employed in a purity of from 90% to 100%, preferably from 95% to 100% (according to NMR spectrum).

Examples of such preparations are

I. a solution of 90 parts by weight of a compound I according to the invention and 10 parts by weight of N-methyl-α-pyrrolidone, which is suitable for application in the form of very small drops;

II. a solution of 20 parts by weight of a compound I according to the invention in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the formulation in water.

III. a solution of 20 parts by weight of a compound I according to the invention in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of a compound I according to the invention in a mixture of 25 parts by weight of cyclohexanone, 65 parts by weight of a petroleum fraction of boiling point from 210 to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of a compound I according to the invention, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel; a spray liquor is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of a compound I according to the invention, 10 parts by weight of the sodium salt of a phenolsulfonic acid/urea/ formal-dehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 2 parts by weight of the sodium salt of a phenolsulfonic acid/urea/ formaldehyde condensate and 68 parts by weight of a paraffinic mineral oil;

X. a mixture, ground in a hammer mill, of 10 parts by weight of a compound I according to the invention, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds I are applied by treating the fungi or the seeds, plants, materials or the soil to be protected from fungal attack with a fungicidally effective amount of the active compounds.

They are applied before or after the infection of the materials, plants or seeds by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha, of active compound.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even immediately before use (tank mix). On mixing with fungicides or insecticides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfides [sic], ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis (thiocarbamoyl) disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)- s-triazine, O,O-diethyl phthalimidophosphonothioate, 5-amino-1-β-[bis-(dimethylamino)-phosphinyl]-3-phenyl-1,2,4-triazole, 2,3-dicyano-1,4-dithioanthraquinone, 2-thio-1,3-dithiolo-β-[4,5-b] quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide; N-ichlorofluoromethylthio-N',N'-dimethyl-N-phenylsulfamide, 5-ethoxy-3-trichloromethyl-1,2,3-thiadiazole, 2-thiocyanato1,4-dichlthiazole, 1,4-dichloro-2,5-dimethoxybenzene, 4-(2-chlorophenylhydrazono)-3-methyl-5-isoxazolone, pyridine-2-thio-1-oxide [sic], 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine- 1,4-diylbis(1-(2,2,2-trichloroethyl)formamide [sic], 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-lH-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole.

SYNTHESIS EXAMPLES

The procedures presented in the Synthesis Examples below were used with appropriate modification of the starting compounds to obtain further compounds I. The compounds thus obtained are listed with physical data in the following Table.

Example 1

5,7-Dimethyl-2-hydroxypyrazolo[1,5a]pyrimidine 10 g (0.1 mol) of pentane-2,4-dione, 9.9 g (0.1 mol) of 2-cyanoacethydrazide and 0.5 ml of glacial acetic acid are dissolved in 20 ml of ethanol and the mixture is refluxed for 30 minutes. After cooling to room temperature, the suspension is added to 120 ml of 2N sodium hydroxide solution and refluxed for 15 minutes. The cooled reaction mixture is adjusted to pH 7 using 5N hydrochloric acid (ice cooling) and the resulting solid is filtered off with suction, washed with water and pentane/methyl tert-butyl ether (1:5) and dried.

11.1 g (68% of theory) of the desired product are obtained.

M.p.=233° C. (Lit. 229–230° C.) Liebigs Ann 1961, 647, 116.

$^1$H-NMR (ppm): 2.40 (s, 3H); 2.55 (s, 3H); 5.70 (s, 1H) 6.65 (s, 1H); 10.90 (m,1H)

Example 2

Methyl 2-[2-(5,7-dimethylpyrazolo[1,5a]pyrimidin-2-yloxymethyl)phenyl]-3-methoxyacrylate 1.25 g (7.7 mmol) of 5,7-dimethyl-2-hydroxypyrazolo[1, 5a]pyrimidine are dissolved in 30 ml of methanol and treated with 1.4 g of 30% sodium methoxide solution in methanol (1.1 eq). After stirring at room temperature for 10 minutes, the solution is evaporated in vacuo and the residue is taken up in 30 ml of dimethylformamide.

0.12 g (0.1 eq) of potassium iodide and 2.0 g (7.0 mmol) of methyl 2-(2-bromomethylphenyl)methoxyiminoacetate dissolved in 20 ml of DMF are added dropwise to this solution. After stirring at room temperature for 4 hours, the reaction mixture is added to ice and the resulting precipitate is filtered off with suction and washed with pentane. 1.7 g of the title compound having a melting point of 136–139° C. are obtained. Yield: 66% of theory $^1$H-NMR: 2.50 (s,3H); 2.63 (s,3H); 3.69 (s,3H); 3.83 (s,3H); 5.22 (s,2H); 5.88 (s,1H); 6.41 (s,1H); 7.25 (m,1H); 7.33 (m,2H); 7.60 (s,1H) 7.62 (m,1H).

Example 3

Methyl 2-[2-(5,7-dimethylpyrazolo[1,5a]pyrimidin-2-yloxymethyl)phenyl]methoxyiminoacetate 3.13 g (19.2 mmol) of 5,7-dimethyl-2-hydroxypyrazolo [1,5a]pyrimidine are dissolved in 50 ml of methanol and treated with 3.5 g of 30% sodium methoxide solution in methanol (1.1 eq). After stirring at room temperature for 10 minutes, the solution is evaporated in vacuo and the residue is taken up in 50 ml of dimethylformamide.

0.3 g (1.1 eq) of potassium iodide and 5.0 g (17.5 mmol) of methyl 2-(2-bromomethylphenyl)methoxyiminoacetate dissolved in 30 ml of DMF are added dropwise to this solution. After stirring at room temperature for 4 hours, the reaction mixture is added to ice and the resulting precipitate is filtered off with suction and washed with pentane. 4.8 g of the title compound having a melting point of 123–126° C. are obtained. Yield: 75% of theory $^1$H-NMR: 2.30 (s,3H); 2.43 (s,3H); 3.86 (s,3H); 4.06 (s,3H); 5.24 (s,2H); 5.88 (s,1H); 6.42 (s,1H); 7.20 (m,1H); 7.42 (m,2H); 7.64 (s,1H).

Example 4

Methyl 2-[2-(5,7-dimethylpyrazolo[1,5a]pyrimidin-2-yloxymethyl)phenyl]methoxyiminoacetate 2.5 g (6.8 mmol) of methyl 2[2-(5,7-dimethylpyrazolo[1,5a]pyrimidin-2-yxloxymethyl)phenyl]methoxyiminoacetate [sic] (product from Example 3) are dissolved in 20 ml of tetrahydrofuran, 11.6 g of 40% strength methylamine solution (25 eq) are added and the reaction mixture is stirred at room temperature for 12 hours.

After evaporating the reaction solution under reduced pressure, the residue is taken up in ethyl acetate and washed twice with water. The organic phase is dried over sodium sulfate and concentrated in vacuo. 2.3 g of brownish crystals are obtained having a melting point of 135–138° C. Yield: 95% of theory $^1$H-NMR: 2.48 (s,3H); 2.61 (s,3H); 2.93 (d,3H); 3.96 (s,3H); 5.22 (s,2H); 5.88 (s,1H); 6.40 (s,1H); 6.82 (m,1H); 7.25 (m,1H); 7.40 (m,2H); 7.60 (m,1H).

Example 5

Methyl 2-[2-(5,7-dimethylpyrazolo[1,5a]-pyrimidin-2-yloxymethyl)phenyl]crotonate 2.3 g (14 mmol) of 5,7-dimethyl-2-hydroxypyrazolo[1,5a]pyrimidine are dissolved in 30 ml of methanol and treated with 2.5 g of 30% strength sodium methoxide solution in methanol (1.1 eq). After stirring at room temperature for 15 minutes, the solution is evaporated in vacuo and the residue is taken up in 50 ml of dimethylformamide.

0.2 g (1.1 eq) of potassium iodide and 3.2 g (12 mmol) of methyl 2-(2-bromomethylphenyl)crotonate dissolved in 30 ml of DMF are added dropwise to this solution. After stirring at room temperature for one day, the reaction mixture is added to ice and the precipitate formed is filtered off with suction and washed with pentone [sic]. 3.47 g of the title compound having a melting point of 109–110° C. are obtained. Yield: 83% of theory $^1$H-NMR: 1.70 (d,3H); 2.52 (s,3H); 2.68 (s,3H); 3.72 (s,3H); 5.20 (s,2H); 5.90 (s,1H); 6.43 (s,1H); 7.21 (m,1H); 7.30 (q,1H); 7.40 (m,2H); 7.65 (m,1H).

| No. | R' | R"$_m$ | Y$_n$ | R$^1$ | R$^2$ | R$^3$ | R$^4$ | Physical data* |
|---|---|---|---|---|---|---|---|---|
| 1 | CH$_3$O—CO—•=NOCH$_3$ | H | OCH$_2$ | CH$_3$ | H | CH$_3$ | H | m.p. = 123°–126° C. |
| 2 | CH$_3$O—CO—•=CHOCH$_3$ | H | OCH$_2$ | CH$_3$ | H | CH$_3$ | H | m.p. = 134°–137° C. |
| 3 | CH$_3$NH—CO—•=NOCH$_3$ | H | OCH$_2$ | CH$_3$ | H | CH$_3$ | H | m.p. = 135°–138° C. |
| 4 | CH$_3$O—CO—•=NOCH$_3$ | h | OCH$_2$ | CH$_3$ | H | Ph | H | m.p. = 161° C. |
| 5 | CH$_3$O—CO—•=CHOCH$_3$ | H | OCH$_2$ | CH$_3$ | H | Ph | H | m.p. = 182°–184° C. |
| 6 | CH$_3$O—CO—•=NOCH$_3$ | H | OCH$_2$ | CH$_3$ | H | CH$_3$ | CH$_3$ | m.p. = 111° C. |
| 7 | CH$_3$O—CO—•=CHOCH$_3$ | H | OCH$_2$ | CH$_3$ | H | CH$_3$ | CH$_3$ | m.p. = 107°–109° C. |
| 8 | CH$_3$O—CO—•=NOCH$_3$ | H | OCH$_2$ | C$_6$H$_5$ | H | CH$_3$ | H | m.p. = 128°–131° C. |
| 9 | CH$_3$O—CO—•=CHOCH$_3$ | H | OCH$_2$ | C$_6$H$_5$ | H | CH$_3$ | H | m.p. = 128°–132° C. |
| 10 | CH$_3$O—CO—•=NOCH$_3$ | H | OCH$_2$ | CH$_3$ | H | CH$_3$ | C$_2$H$_5$ | m.p. = 110° C. |
| 11 | CH$_3$O—CO—•=CHOCH$_3$ | H | OCH$_2$ | CH$_3$ | H | CH$_3$ | C$_2$H$_5$ | m.p. = IR [cm$^{-1}$]: 1709, 1632, 1508, 1451, 1129. |
| 12 | CH$_3$O—CO—•=NOCH$_3$ | H | OCH$_2$ | CH$_3$ | H | C$_6$H$_5$ | C$_2$H$_5$ | m.p. = 105°–108° C. |
| 13 | CH$_3$O—CO—•=CHOCH$_3$ | H | OCH$_2$ | CH$_3$ | H | C$_6$H$_5$ | C$_2$H$_5$ | m.p. = 129°–131° C. |
| 14 | CH$_3$NHCO—•=NOCH$_3$ | H | OCH$_2$ | CH$_3$ | H | CH$_3$ | C$_2$H$_5$ | m.p. = 142° C. |
| 15 | CH$_3$NHCO—•=NOCH$_3$ | H | OCH$_2$ | CH$_3$ | H | C$_6$H$_5$ | C$_2$H$_5$ | m.p. = 134°–137° C. |
| 16 | CH$_3$O—CO—•=NOCH$_3$ | H | OCH$_2$ | C$_2$H$_5$ | H | C$_2$H$_5$ | CH$_3$ | m.p. = 114° C. |
| 17 | CH$_3$O—CO—•=CHOCH$_3$ | H | OCH$_2$ | C$_2$H$_5$ | H | C$_2$H$_5$ | CH$_3$ | m.p. = IR [cm$^{-1}$]: 1710, 1633, 1512, 1256, 1129. |
| 18 | CH$_3$O—CO—•=NOCH$_3$ | H | OCH$_2$ | CH$_3$ | H | C$_6$H$_5$ | CH$_3$ | m.p. = 122°–126° C. |
| 19 | CH$_3$O—CO—•=CHOCH$_3$ | H | OCH$_2$ | CH$_3$ | H | C$_6$H$_5$ | CH$_3$ | m.p. = 117°–119° C. |
| 20 | CH$_3$O—CO—•=NOCH$_3$ | H | OCH$_2$ | Ph | H | CH$_3$ | CH$_3$ | m.p. = 135°–138° C. |
| 21 | CH$_3$NH—CO—•=NOCH$_3$ | H | OCH$_2$ | CH$_3$ | H | CH$_3$ | CH$_3$ | m.p. = 148° C. |
| 22 | CH$_3$NH—CO—•=NOCH$_3$ | H | OCH$_2$ | C$_2$H$_5$ | H | C$_2$H$_5$ | CH$_3$ | m.p. = 126° C. |
| 23 | CH$_3$NH—CO—•=NOCH$_3$ | H | OCH$_2$ | CH$_3$ | H | C$_6$H$_5$ | CH$_3$ | m.p. = 122°–126° C. |
| 24 | CH$_3$NH—CO—•=NOCH$_3$ | H | OCH$_2$ | Ph | H | CH$_3$ | CH$_3$ | m.p. = 187° C. |
| 25 | CH$_3$O—CO—•=NOCH$_3$ | H | OCH$_2$ | C$_2$H$_5$ | H | C$_2$H$_5$ | H | m.p. = 59°–61° C. |
| 26 | CH$_3$NH—CO—•=NOCH$_3$ | H | OCH$_2$ | C$_2$H$_5$ | H | C$_2$H$_5$ | H | m.p. = 100°–101° C. |
| 27 | CH$_3$NH—CO—•=NOCH$_3$ | H | OCH$_2$ | CH$_3$ | H | C$_6$H$_5$ | H | m.p. = 162°–164° C. |
| 28 | CH$_3$NH—CO—•=NOCH$_3$ | H | OCH$_2$ | C$_6$H$_5$ | H | CH$_3$ | H | m.p. = 105°–109° C. |
| 29 | CH$_3$O—CO—•=CHOCH$_3$ | H | OCH$_2$ | C$_6$H$_5$ | H | CH$_3$ | CH$_3$ | m.p. = 167° C. |
| 30 | CH$_3$O—CO—•=CHOCH$_3$ | H | OCH$_2$ | C$_2$H$_5$ | H | C$_2$H$_5$ | H | m.p. = 62° C. |
| 31 | CH$_3$O—CO—•=NOCH$_3$ | H | OCH$_2$ | CH$_3$ | CH$_3$ | CH$_3$ | H | m.p. = 145°–147° C. |
| 32 | CH$_3$NH—CO—•=NOCH$_3$ | H | OCH$_2$ | CH$_3$ | CH$_3$ | CH$_3$ | H | m.p. = 128°–129° C. |
| 33 | CH$_3$O—CO—•=CHCH$_3$ | H | OCH$_2$ | CH$_3$ | CH$_3$ | CH$_3$ | H | m.p. = 126°–128° C. |
| 34 | CH$_3$O—CO—•=CHCH$_3$ | H | OCH$_2$ | CH$_3$ | H | CH$_3$ | H | m.p. = 109°–110° C. |
| 35 | CH$_3$O—CO—•=CHCH$_3$ | H | OCH$_2$ | CF$_3$ | H | CH$_3$ | H | IR [cm$^{-1}$] = 1715, 1566, 1508, 1257, 1037. |
| 36 | CH$_3$O—CO—•=CHCH$_3$ | H | OCH$_2$ | CH$_3$ | C$_2$H$_5$ | CH$_3$ | H | m.p. = 105°–107° C. |
| 37 | CH$_3$O—CO—•=NOCH$_3$ | H | OCH$_2$ | CH$_3$ | C$_2$H$_5$ | CH$_3$ | H | m.p. = 128°–129° C. |
| 38 | CH$_3$O—CO—•=CHCH$_3$ | H | OCH$_2$ | CH$_3$ | C$_2$H$_5$ | CH$_3$ | H | m.p. = 113°–115° C. |
| 39 | CH$_3$NH—CO—•=NOCH$_3$ | H | OCH$_2$ | CH$_3$ | C$_2$H$_5$ | CH$_3$ | H | m.p. = 136°–138° C. |
| 40 | CH$_3$O—CO—•=CHCH$_3$ | H | OCH$_2$ | CH$_3$ | C$_3$H$_7$ | CH$_3$ | H | m.p. = 103°–105° C. |
| 41 | CH$_3$O—CO—•=NOCH$_3$ | H | OCH$_2$ | CH$_3$ | C$_3$H$_7$ | CH$_3$ | H | m.p. = 108°–110° C. |
| 42 | CH$_3$O—CO—•=CHCH$_3$ | H | OCH$_2$ | CH$_3$ | C$_3$H$_7$ | CH$_3$ | H | m.p. = 75°–78° C. |
| 43 | CH$_3$NH—CO—•=NOCH$_3$ | H | OCH$_2$ | CH$_3$ | C$_3$H$_7$ | CH$_3$ | H | m.p. = 119°–120° C. |
| 44 | CH$_3$O—CO—•=CHOCH$_3$ | H | OCH$_2$ | CH$_3$ | CH$_3$ | CH$_3$ | H | m.p. = 150°–153° C. |

-continued

| No. | R' | R"$_m$ | Y$_n$ | R$^1$ | R$^2$ | R$^3$ | R$^4$ | Physical data* |
|---|---|---|---|---|---|---|---|---|
| 45 | CH$_3$O—CO—•=CHOCH$_3$ | H | OCH$_2$ | CH$_3$ | H | CF$_3$ | C$_2$H$_5$ | m.p. = 92° C. |
| 46 | CH$_3$O—CO—•=NOCH$_3$ | H | OCH$_2$ | CH$_3$ | H | CF$_3$ | C$_2$H$_5$ | m.p. = 55° C. |
| 47 | CH$_3$O—CO—•=CHCH$_3$ | H | OCH$_2$ | CH$_3$ | H | CF$_3$ | C$_2$H$_5$ | oil |
| 48 | CH$_3$O—CO—•=NOCH$_3$ | H | OCH$_2$ | CF$_3$ | H | CH$_3$ | C$_2$H$_5$ | m.p. = 78° C. |
| 49 | CH$_3$O—CO—•=CHCH$_3$ | H | OCH$_2$ | CF$_3$ | H | CH$_3$ | C$_2$H$_5$ | m.p. = 60° C. |
| 50 | CH$_3$NH—CO—•=NOCH$_3$ | H | OCH$_2$ | CF$_3$ | H | CH$_3$ | C$_2$H$_5$ | m.p. = 167°–170° C. |
| 51 | CH$_3$O—CO—•=NOCH$_3$ | h | OCH$_2$ | CF$_3$ | H | CF$_3$ | C$_2$H$_5$ | m.p. = 61° C. |
| 52 | CH$_3$O—CO—•=CHOCH$_3$ | H | OCH$_2$ | CF$_3$ | H | CF$_3$ | H | IR [cm$^{-1}$]: 1709, 1631, 1515, 1268, 1208. |
| 53 | CH$_3$O—CO—•=CHOCH$_3$ | H | OCH$_2$ | CF$_3$ | H | CF$_3$ | C$_2$H$_5$ | IR [cm$^{-1}$]: 1711, 1632, 1516, 1456, 1272, 1203. |
| 54 | CH$_3$NH—CO—•=NOCH$_3$ | H | OCH$_2$ | CF$_3$ | H | CF$_3$ | C$_2$H$_5$ | m.p. = 135° C. |
| 55 | CH$_3$O—CO—•=CHOCH$_3$ | H | OCH$_2$ | CF$_3$ | H | CF$_3$ | CH$_3$ | m.p. = 71–73° C. |
| 56 | CH$_3$O—CO—•=NHOCH$_3$ | H | OCH$_2$ | CF$_3$ | H | CF$_3$ | CH$_3$ | m.p. = 92° C. |
| 57 | CH$_3$O—CO—•=CHCH$_3$ | H | OCH$_2$ | CF$_3$ | H | CF$_3$ | CH$_3$ | IR [cm$^{-1}$]: 1718, 1519, 1569, 1207, 1173. |
| 58 | CH$_3$NH—CO—•=NOCH$_3$ | H | OCH$_2$ | CF$_3$ | H | CF$_3$ | CH$_3$ | m.p. = 111° C. |
| 59 | CH$_3$O—CO—•=NOCH$_3$ | H | OCH$_2$ | CF$_3$ | H | CH$_3$ | H | m.p. = 107° C. |
| 60 | CH$_3$O—CO—•=NOCH$_3$ | H | OCH$_2$ | CF$_3$ | H | CF$_3$ | H | m.p. = 109–110° C. |
| 61 | CH$_3$O—CO—•=CHCH$_3$ | H | OCH$_2$ | CF$_3$ | H | CF$_3$ | H | IR [cm$^{-1}$]: 1717, 1577, 1515, 1268, 1208. |
| 62 | CH$_3$O—CO—•=CHCH$_3$ | H | OCH$_2$ | CH$_3$ | CO$_2$CH$_3$ | CH$_3$ | CH$_3$ | m.p. = 145° C. |
| 63 | CH$_3$NH—CO—•=NOCH$_3$ | H | OCH$_2$ | CH$_3$ | H | CF$_3$ | C$_2$H$_5$ | m.p. = 138° C. |
| 64 | CH$_3$O—CO—•=CHCH$_3$ | H | OCH$_2$ | CF$_3$ | H | CH$_3$ | H | IR [cm$^{-1}$]: 1715, 1566, 1508, 1257, 1037. |
| 65 | CH$_3$NH—CO—•=NOCH$_3$ | H | OCH$_2$ | CF$_3$ | H | CF$_3$ | H | m.p. = 108° C. |
| 66 | CH$_3$O—CO—•=CHCH$_3$ | H | OCH$_2$ | CH$_3$ | CO$_2$CH$_3$ | CH$_3$ | CH$_3$ | m.p. = 118° C. |
| 67 | CH$_3$O—CO—•=CHOCH$_3$ | H | OCH$_2$ | CH$_3$ | CH$_3$ | CH$_3$ | C$_2$H$_5$ | m.p. = 140° C. |
| 68 | CH$_3$O—CO—•=CHCH$_3$ | H | OCH$_2$ | CH$_3$ | CH$_3$ | CH$_3$ | C$_2$H$_5$ | m.p. = 142° C. |
| 69 | CH$_3$NH—CO—•=NOCH$_3$ | H | OCH$_2$ | CH$_3$ | CH$_3$ | CH$_3$ | H | IR [cm$^{-1}$]: 1672, 1566, 1508, 1219, 1037. |
| 70 | CH$_3$O—CO—•=NOCH$_3$ | H | OCH$_2$ | CH$_3$ | CH$_3$ | CH$_3$ | C$_2$H$_5$ | m.p. = 157°–158° C. |
| 71 | CH$_3$O—CO—•=NOCH$_3$ | H | OCH$_2$ | CO$_2$CH$_3$ | CH$_3$ | CH$_3$ | CH$_3$ | m.p. = 130°–131° C. |
| 72 | CH$_3$NH—CO—•=NOCH$_3$ | H | OCH$_2$ | CH$_3$ | CO$_2$CH$_3$ | CH$_3$ | CH$_3$ | m.p. = 138°–140° C. |
| 73 | CH$_3$O—CO—•=NOCH$_3$ | H | OCH$_2$ | CH$_3$ | CH$_3$ | CH$_3$ | CH$_3$ | m.p. = 148°–149° C. |
| 74 | CH$_3$O—CO—•=CHOCH$_3$ | H | OCH$_2$ | CH$_3$ | CH$_3$ | CH$_3$ | CH$_3$ | m.p. = 122°–123° C. |
| 75 | CH$_3$O—CO—•=CHCH$_3$ | H | OCH$_2$ | CH$_3$ | CH$_3$ | CH$_3$ | CH$_3$ | m.p. = 172°–173° C. |
| 76 | CH$_3$NH—CO—•=NOCH$_3$ | H | OCH$_2$ | CH$_3$ | CH$_3$ | CH$_3$ | CH$_3$ | m.p. = 185°–187° C. |
| 77 | CH$_3$O—CO—•=NOCH$_3$ | H | OCH$_2$ | CH$_3$ | CO$_2$H$_3$ | CH$_3$ | H | m.p. 112°–115° C. |
| 78 | CH$_3$O—CO—•=CHCH$_3$ | H | OCH$_2$ | CH$_3$ | CO$_2$H$_3$ | CH$_3$ | H | m.p. 115°–116° C. |
| 79 | CH$_3$O—CO—•=CHOCH$_3$ | H | OCH$_2$ | CH$_3$ | CO$_2$H$_3$ | CH$_3$ | C$_2$H$_5$ | m.p. 90°–94° C. |
| 80 | CH$_3$O—CO—•=NOCH$_3$ | H | OCH$_2$ | CH$_3$ | CO$_2$H$_3$ | CH$_3$ | C$_2$H$_5$ | m.p. 93°–95° C. |
| 81 | CH$_3$NH—CO—•=NOCH$_3$ | H | OCH$_2$ | CH$_3$ | CO$_2$H$_3$ | CH$_3$ | C$_2$H$_5$ | m.p. 120°–124° C. |
| 82 | CH$_3$O—CO—•=CHCH$_3$ | H | OCH$_2$ | CH$_3$ | CO$_2$H$_3$ | CH$_3$ | C$_2$H$_5$ | m.p. 92°–93° C. |
| 83 | CH$_3$O—CO—•=CHCH$_3$ | H | OCH$_2$ | C$_2$H$_5$ | H | C$_2$H$_5$ | C$_2$H$_5$ | m.p. 80°–83° C. |
| 84 | CH$_3$O—CO—•=NOCH$_3$ | H | OCH$_2$ | C$_2$H$_5$ | H | C$_2$H$_5$ | C$_2$H$_5$ | m.p. 73°–75° C. |
| 85 | CH$_3$NH—CO—•=NOCH$_3$ | H | OCH$_2$ | C$_2$H$_5$ | H | C$_2$H$_5$ | C$_2$H$_5$ | m.p. 83°–84° C. |
| 86 | CH$_3$O—CO—•=CHCH$_3$ | H | OCH$_2$ | C$_2$H$_5$ | H | C$_2$H$_5$ | C$_2$H$_5$ | IR [cm$^{-1}$]: 1718, 1628, 1531, 1507, 1252. |
| 87 | CH$_3$NH—CO—•=NOCH$_3$ | H | OCH$_2$ | CH$_3$ | CH$_3$ | CH$_3$ | C$_2$H$_5$ | m.p. 165°–166° C. |
| 88 | CH$_3$O—CO—•=CHOCH$_3$ | H | OCH$_2$ | CH$_3$ | CO$_2$CH$_3$ | CH$_3$ | H | m.p. 110°–112° C. |
| 89 | CH$_3$NH—CO—•=NOCH$_3$ | H | OCH$_2$ | CH$_3$ | CO$_2$CH$_3$ | CH$_3$ | H | IR [cm$^{-1}$]: 1723, 1671, 1617, 1502, 10372. [sic] |
| 90 | CH$_3$O—CO—•=CHOCH$_3$ | H | OCH$_2$ | CH$_3$ | H | CF$_3$ | H | m.p. 88° C. |
| 91 | CH$_3$O—CO—•=NOCH$_3$ | H | OCH$_2$ | CH$_3$ | H | CF$_3$ | H | m.p. 107° C. |
| 92 | CH$_3$O—CO—•=CHOCH$_3$ | H | OCH$_2$ | H | H | CH$_3$ | CH$_3$ | m.p. 138° C. |
| 93 | CH$_3$O—CO—•=NOCH$_3$ | H | OCH$_2$ | H | H | CH$_3$ | CH$_3$ | m.p. 134° C. |
| 94 | CH$_3$NH—CO—•=NOCH$_3$ | H | OCH$_2$ | H | H | CH$_3$ | CH$_3$ | m.p. 182° C. |
| 95 | CH$_3$O—CO—•=CHCH$_3$ | H | OCH$_2$ | H | H | CH$_3$ | CH$_3$ | m.p. 128°–130° C. |
| 96 | CH$_3$NH—CO—•=NOCH$_3$ | H | OCH$_2$ | CH$_3$ | H | CF$_3$ | H | m.p. 98°–100° C. |
| 97 | CH$_3$O—CO—•=CHCH$_3$ | H | OCH$_2$ | CH$_3$ | H | CF$_3$ | H | m.p. 92° C. |
| 98 | CH$_3$O—CO—•=CHOCH$_3$ | H | OCH$_2$ | CH$_3$ | Cl | CH$_3$ | H | m.p. 142°–145° C. |
| 99 | CH$_3$O—CO—•=NOCH$_3$ | H | OCH$_2$ | CH$_3$ | Cl | CH$_3$ | H | m.p. 148°–151° C. |
| 100 | CH$_3$O—CO—•=CHCH$_3$ | H | OCH$_2$ | CH$_3$ | Cl | CH$_3$ | H | m.p. 89°–93° C. |
| 101 | CH$_3$O—CO—•=CHOCH$_3$ | H | OCH$_2$ | CH$_3$ | H | CF$_3$ | CH$_3$ | m.p. 107°–109° C. |
| 102 | CH$_3$O—CO—•=NOCH$_3$ | H | OCH$_2$ | CH$_3$ | H | CF$_3$ | CH$_3$ | m.p. 105°–108° C. |
| 103 | CH$_3$O—CO—•=CHCH$_3$ | H | OCH$_2$ | CH$_3$ | H | CF$_3$ | CH$_3$ | m.p. 102°–104° C. |
| 104 | CH$_3$NH—CO—•=NOCH$_3$ | H | OCH$_2$ | CH$_3$ | Cl | CH$_3$ | H | m.p. 139°–140° C. |
| 105 | CH$_3$O—CO—•=CHCH$_3$ | H | OCH$_2$ | CF$_3$ | H | CH$_3$ | CH$_3$ | m.p. 120°–121° C. |
| 106 | CH$_3$O—CO—•=NOCH$_3$ | H | OCH$_2$ | CF$_3$ | H | CH$_3$ | CH$_3$ | m.p. 131°–132° C. |
| 107 | CH$_3$O—CO—•=CHCH$_3$ | H | OCH$_2$ | CF$_3$ | H | CF$_3$ | CH$_3$ | m.p. 104°–107° C. |
| 108 | CH$_3$O—CO—•=NOCH$_3$ | H | OCH$_2$ | CH$_3$ | H | CF$_3$ | CH$_3$ | m.p. 162°–164° C. |
| 109 | CH$_3$NH—CO—•=NOCH$_3$ | H | OCH$_2$ | CF$_3$ | H | CH$_3$ | CH$_3$ | m.p. 160°–162° C. |
| 110 | CH$_3$O—CO—•=CHCH$_3$ | H | OCH$_2$ | CH$_3$ | H | CH$_3$ | CH$_3$ | m.p. = 100–102 |
| 111 | CH$_3$O—CO—•=CHCH$_3$ | H | OCH$_2$ | CH$_2$CH$_3$ | H | CH$_2$CH$_3$ | H | m.p. = 70–72 |
| 112 | CH$_3$O—CO—•=CHCH$_3$ | H | OCH$_2$ | CH$_2$CH$_3$ | H | CH$_2$CH$_3$ | CH$_3$ | m.p. = 127–129 |
| 113 | CH$_3$O—CO—•=CHOCH$_3$ | H | OCH$_2$ | CH$_3$ | CH$_2$CH$_3$ | CH$_3$ | CH$_3$ | m.p. = 127–129 |
| 114 | CH$_3$O—CO—•=NOCH$_3$ | H | OCH$_2$ | CH$_3$ | CH$_2$CH$_3$ | CH$_3$ | CH$_3$ | m.p. = 133–135 |

-continued

| No. | R' | R"$_m$ | Y$_n$ | R$^1$ | R$^2$ | R$^3$ | R$^4$ | Physical data* |
|---|---|---|---|---|---|---|---|---|
| 115 | CH$_3$O—CO—•=CHCH$_3$ | H | OCH$_2$ | CH$_3$ | CH$_2$CH$_3$ | CH$_3$ | CH$_3$ | m.p. = 106–108 |
| 116 | CH$_3$O—CO—•=CHOCH$_3$ | H | OCH$_2$ | CH$_3$ | (CH$_2$)$_2$CH$_3$ | CH$_3$ | CH$_3$ | m.p. = 112–113 |
| 117 | CH$_3$O—CO—•=NOCH$_3$ | H | OCH$_2$ | CH$_3$ | (CH$_2$)$_2$CH$_3$ | CH$_3$ | CH$_3$ | m.p. = 126–128 |
| 118 | CH$_3$O—CO—•=CHCH$_3$ | H | OCH$_2$ | CH$_3$ | (CH$_2$)$_2$CH$_3$ | CH$_3$ | CH$_3$ | m.p. = 95–97 |
| 119 | CH$_3$NH—CO—•=NOCH$_3$ | H | OCH$_2$ | CH$_3$ | CH$_2$CH$_3$ | CH$_3$ | CH$_3$ | m.p. = 124–126 |
| 120 | CH$_3$NH—CO—•=NOCH$_3$ | H | OCH$_2$ | CH$_3$ | (CH$_2$)$_2$CH$_3$ | CH$_3$ | CH$_3$ | m.p. = 80–83 |
| 121 | CH$_3$O—CO—•=CHOCH$_3$ | H | OCH$_2$ | CH$_3$ | Cl | CH$_3$ | CH$_3$ | m.p. = 154–156 |
| 122 | CH$_3$O—CO—•=NOCH$_3$ | H | OCH$_2$ | CH$_3$ | Cl | CH$_3$ | CH$_3$ | m.p. = 170–173 |
| 123 | CH$_3$O—CO—•=CHCH$_3$ | H | OCH$_2$ | CH$_3$ | Cl | CH$_3$ | CH$_3$ | m.p. = 148–149 |
| 124 | CH$_3$NH—CO—•=NOCH$_3$ | H | OCH$_2$ | CH$_3$ | Cl | CH$_3$ | CH$_3$ | m.p. = 198–200 |
| 125 | CH$_3$O—CO—•=CHOCH$_3$ | H | OCH$_2$ | CH$_3$ | Cl | CH$_3$ | CH$_2$CH$_3$ | m.p. = 122–125 |
| 126 | CH$_3$O—CO—•=NOCH$_3$ | H | OCH$_2$ | CH$_3$ | Cl | CH$_3$ | CH$_2$CH$_3$ | m.p. = 140–143 |
| 127 | CH$_3$O—CO—•=CHCH$_3$ | H | OCH$_2$ | CH$_3$ | Cl | CH$_3$ | CH$_2$CH$_3$ | m.p. = 113–115 |
| 128 | CH$_3$O—CO—•=CHOCH$_3$ | H | OCH$_2$ | CH$_3$ | H | 2-pyridyl | H | m.p. = 162–164 |
| 129 | CH$_3$O—CO—•=NOCH$_3$ | H | OCH$_2$ | CH$_3$ | H | 2-pyridyl | H | m.p. = 158–159 |
| 130 | CH$_3$NH—CO—•=NOCH$_3$ | H | OCH$_2$ | CH$_3$ | H | 2-pyridyl | H | m.p. = 140–141 |
| 131 | CH$_3$O—CO—•=CHOCH$_3$ | H | OCH$_2$ | CF$_3$ | H | H | CH$_2$CH$_3$ | m.p. = 90–92 |
| 132 | CH$_3$O—CO—•=NOCH$_3$ | H | OCH$_2$ | CF$_3$ | H | H | CH$_2$CH$_3$ | m.p. = 119–121 |
| 133 | CH$_3$O—CO—•=CHCH$_3$ | H | OCH$_2$ | CF$_3$ | H | H | CH$_2$CH$_3$ | m.p. = 87–88 |
| 134 | CH$_3$O—CO—•=CHOCH$_3$ | H | OCH$_2$ | CF$_3$ | H | H | CH$_3$ | m.p. = 132–133 |
| 135 | CH$_3$O—CO—•=NOCH$_3$ | H | OCH$_2$ | CF$_3$ | H | H | CH$_3$ | m.p. = 158–159 |
| 136 | CH$_3$O—CO—•=CHCH$_3$ | H | OCH$_2$ | CF$_3$ | H | H | CH$_3$ | m.p. = 118–120 |
| 137 | CH$_3$NH—CO—•=NOCH$_3$ | H | OCH$_2$ | CH$_3$ | Cl | CH$_3$ | CH$_2$CH$_3$ | m.p. = 180–181 |
| 138 | CH$_3$O—CO—•=CHCH$_3$ | H | OCH$_2$ | CH$_3$ | H | 2-pyridyl | H | m.p. = 140–141 |
| 139 | CH$_3$NH—CO—•=NOCH$_3$ | H | OCH$_2$ | CF$_3$ | H | H | CH$_3$ | m.p. = 151–153 |
| 140 | CH$_3$NH—CO—•=NOCH$_3$ | H | OCH$_2$ | CF$_3$ | H | H | CH$_2$CH$_3$ | m.p. = 155–156 |
| 141 | CH$_3$O—CO—•=CHOCH$_3$ | H | OCH$_2$ | H | H | CF$_3$ | CH$_2$CH$_3$ | m.p. = 87–90 |
| 142 | CH$_3$O—CO—•=NOCH$_3$ | H | OCH$_2$ | H | H | CF$_3$ | CH$_2$CH$_3$ | m.p. = 112–113 |
| 143 | CH$_3$O—CO—•=CHCH$_3$ | H | OCH$_2$ | H | H | CF$_3$ | CH$_2$CH$_3$ | m.p. = 106–108 |
| 144 | CH$_3$O—CO—•=NOCH$_3$ | H | OCH$_2$ | H | H | CH$_3$ | H | m.p. = 109–110 |
| 145 | CH$_3$O—CO—•=CHCH$_3$ | H | OCH$_2$ | H | H | CH$_3$ | H | m.p. = 88–90 |
| 146 | CH$_3$O—CO—•=CHOCH$_3$ | H | OCH$_2$ | H | CH$_3$ | H | CH$_3$ | m.p. = 136–138 |
| 147 | CH$_3$O—CO—•=NOCH$_3$ | H | OCH$_2$ | H | CH$_3$ | H | CH$_3$ | m.p. = 148–150 |
| 148 | CH$_3$O—CO—•=CHCH$_3$ | H | OCH$_2$ | H | CH$_3$ | H | CH$_3$ | m.p. = 78–80 |
| 149 | CH$_3$NH—CO—•=NOCH$_3$ | H | OCH$_2$ | H | H | CF$_3$ | CH$_2$CH$_3$ | m.p. = 154–156 |
| 150 | CH$_3$O—CO—N—OCH$_3$ | H | OCH$_2$ | H | CH$_3$ | H | CH$_3$ | m.p. = 90–93 |
| 151 | CH$_3$O—CO—•=CHOCH$_3$ | H | OCH$_2$ | H | H | H | CH$_3$ | m.p. = 80–83 |
| 152 | CH$_3$O—CO—•=NOCH$_3$ | H | OCH$_2$ | H | H | H | CH$_3$ | m.p. = 140–142 |
| 153 | CH$_3$NH—CO—•=NOCH$_3$ | H | OCH$_2$ | H | H | CH$_3$ | H | m.p. = 94–100 |
| 154 | CH$_3$NH—CO—•=NOCH$_3$ | H | OCH$_2$ | H | CH$_3$ | H | CH$_3$ | m.p. = 180–181 |
| 155 | CH$_3$O—CO—•=CHCH$_3$ | H | OCH$_2$ | H | H | H | CH$_3$ | m.p. = 149–150 |
| 156 | CH$_3$O—CO—N—OCH$_3$ | H | OCH$_2$ | H | H | H | CH$_3$ | m.p. = 86–88 |
| 157 | CH$_3$NH—CO—•=NOCH$_3$ | H | OCH$_2$ | H | H | H | CH$_3$ | m.p. = 158–160 |
| 158 | CH$_3$O—CO—N—OCH$_3$ | H | OCH$_2$ | H | H | CH$_3$ | H | IR = 1737, 1618, 1556, 1443, 1355 |
| 159 | CH$_3$O—CO—•=CHOCH$_3$ | H | OCH$_2$ | H | H | H | CH$_2$CH$_3$ | m.p. = 85–87 |
| 160 | CH$_3$O—CO—•=NOCH$_3$ | H | OCH$_2$ | H | H | H | CH$_2$CH$_3$ | m.p. = 108–110 |
| 161 | CH$_3$O—CO—•=CHCH$_3$ | H | OCH$_2$ | H | H | H | CH$_2$CH$_3$ | m.p. = 78–79 |
| 162 | CH$_3$O—CO—N—OCH$_3$ | H | OCH$_2$ | H | H | H | CH$_2$CH$_3$ | m.p. = 69–71 |
| 163 | CH$_3$O—CO—•=NOCH$_3$ | H | OCH$_2$ | 2-pyridyl | H | CH$_3$ | CH$_3$ | m.p. = 136–138 |
| 164 | CH$_3$NH—CO—•=NOCH$_3$ | H | OCH$_2$ | H | H | H | CH$_2$CH$_3$ | m.p. = 115–116 |
| 165 | CH$_3$O—CO—•=CHCH$_3$ | H | OCH$_2$ | 2-pyridyl | H | CH$_3$ | CH$_3$ | m.p. = 133–135 |
| 166 | CH$_3$O—CO—N—OCH$_3$ | H | OCH$_2$ | 2-pyridyl | H | CH$_3$ | CH$_3$ | m.p. = 150–152 |
| 167 | CH$_3$O—CO—•=CHOCH$_3$ | H | OCH$_2$ | H | CH$_3$ | H | CH$_2$CH$_3$ | IR = 1708, 1635, 1510, 1256, 1130 |
| 168 | CH$_3$O—CO—•=NOCH$_3$ | H | OCH$_2$ | H | CH$_3$ | H | CH$_2$CH$_3$ | m.p. = 98–100 |
| 169 | CH$_3$O—CO—•=CHCH$_3$ | H | OCH$_2$ | H | CH$_3$ | H | CH$_2$CH$_3$ | IR = 1716, 1635, 1365, 1253, 1036 |
| 170 | CH$_3$NH—CO—•=NOCH$_3$ | H | OCH$_2$ | 2-pyridyl | H | CH$_3$ | CH$_3$ | m.p. = 200–201 |
| 171 | CH$_3$NH—CO—•=NOCH$_3$ | H | OCH$_2$ | H | CH$_3$ | H | CH$_2$CH$_3$ | m.p. = 133–134 |
| 172 | CH$_3$O—CO—N—OCH$_3$ | H | OCH$_2$ | H | CH$_3$ | H | CH$_2$CH$_3$ | IR = 1738, 1635, 1510, 1362, 1104 |
| 173 | CH$_3$O—CO—N—OCH$_3$ | H | OCH$_2$ | CF$_3$ | H | CF$_3$ | CH$_2$CH$_3$ | m.p. = 62–68 |
| 174 | CH$_3$O—CO—N—OCH$_3$ | H | OCH$_2$ | CH$_3$ | H | CF$_3$ | CH$_3$ | m.p. = 100–101 |
| 175 | CH$_3$O—CO—N—OCH$_3$ | H | OCH$_2$ | CF$_3$ | H | CH$_3$ | CH$_3$ | m.p. = 112–114 |
| 176 | CH$_3$O—CO—N—OCH$_3$ | H | OCH$_2$ | CH$_3$ | CO$_2$CH$_3$ | CH$_3$ | CH$_3$ | m.p. = 108–109 |
| 177 | CH$_3$O—CO—N—OCH$_3$ | H | OCH$_2$ | CH$_3$ | CO$_2$CH$_3$ | CH$_3$ | CH$_2$CH$_3$ | m.p. = 105–108 |
| 178 | CH$_3$O—CO—N—OCH$_3$ | H | OCH$_2$ | CH$_3$ | CH$_2$CH$_3$ | CH$_3$ | CH$_3$ | m.p. = 108–109 |
| 179 | CH$_3$O—CO—N—OCH$_3$ | H | OCH$_2$ | CH$_3$ | Cl | CH$_3$ | CH$_3$ | m.p. = 270–271 |
| 180 | CH$_3$O—CO—N—OCH$_3$ | H | OCH$_2$ | CH$_3$ | (CH$_2$)$_2$CH$_3$ | CH$_3$ | CH$_3$ | m.p. = 110–112 |
| 181 | CH$_3$O—CO—N—OCH$_3$ | H | OCH$_2$ | CF$_3$ | H | H | CH$_3$ | m.p. = 133–135 |
| 182 | CH$_3$O—CO—N—OCH$_3$ | H | OCH$_2$ | CF$_3$ | H | H | CH$_2$CH$_3$ | m.p. = 111–115 |
| 183 | CH$_3$O—CO—N—OCH$_3$ | H | OCH$_2$ | CF$_3$ | H | CF$_3$ | H | IR = 1742, 1515, 1269, |

-continued

| No. | R' | R"$_m$ | Y$_n$ | R$^1$ | R$^2$ | R$^3$ | R$^4$ | Physical data* |
|---|---|---|---|---|---|---|---|---|
| 184 | CH$_3$O—CO—N—OCH$_3$ | H | OCH$_2$ | H | H | CF$_3$ | CH$_2$CH$_3$ | 1210, 1170<br>m.p. = 91–93 |
| 189 | CH$_3$O—CO—N—OCH$_3$ | H | OCH$_2$ | CH$_3$ | H | CF$_3$ | H | m.p. = 117–120 |
| 190 | CH$_3$O—CO—N—OCH$_3$ | H | OCH$_2$ | CH$_2$CH$_3$ | H | CH$_2$CH$_3$ | CH$_2$CH$_3$ | IR = 1741, 1628, 1507,<br>1440, 1362 |
| 191 | CH$_3$O—CO—N—OCH$_3$ | H | OCH$_2$ | CH$_3$ | Cl | CH$_3$ | H | m.p. = 110–112 |
| 192 | CH$_3$O—CO—N—OCH$_3$ | H | OCH$_2$ | CH$_3$ | H | 3-pyridyl | H | m.p. = 99–104 |
| 193 | CH$_3$O—CO—N—OCH$_3$ | H | OCH$_2$ | CH$_3$ | CO$_2$CH$_3$ | CH$_3$ | H | m.p. = 119–120 |
| 194 | CH$_3$O—CO—N—OCH$_3$ | H | OCH$_2$ | CH$_3$ | CH$_3$ | CH$_3$ | CH$_3$ | m.p. = 103–104 |
| 195 | CH$_3$O—CO—N—OCH$_3$ | H | OCH$_2$ | CH$_3$ | H | 2-pyridyl | H | m.p. = 107–109 |
| 196 | CH$_3$O—CO—•=CHOCH$_3$ | H | OCH$_2$ | CH(CH$_3$)$_2$ | H | CH(CH$_3$)$_2$ | CH$_3$ | m.p. = 102–105 |
| 197 | CH$_3$O—CO—•=NOCH$_3$ | H | OCH$_2$ | CH(CH$_3$)$_2$ | H | CH(CH$_3$)$_2$ | CH$_3$ | m.p. = 92–94 |
| 198 | CH$_3$O—CO—•=CHOCH$_3$ | H | OCH$_2$ | H | C$_6$H$_5$ | CH$_3$ | CH$_3$ | m.p. = 135–140 |
| 199 | CH$_3$O—CO—•=NOCH$_3$ | H | OCH$_2$ | H | C$_6$H$_5$ | CH$_3$ | CH$_3$ | m.p. = 75–78 |
| 200 | CH$_3$O—CO—•=CHOCH$_3$ | H | OCH$_2$ | H | CH$_3$ | CH$_2$CH$_3$ | CH$_3$ | m.p. = 140–141 |
| 201 | CH$_3$NH—CO—•=NOCH$_3$ | H | OCH$_2$ | CH(CH$_3$)$_2$ | H | CH(CH$_3$)$_2$ | CH$_3$ | m.p. = 100–102 |
| 202 | CH$_3$NH—CO—•=NOCH$_3$ | H | OCH$_2$ | H | C$_6$H$_5$ | CH$_3$ | CH$_3$ | m.p. = 148–150 |
| 203 | R'.2-•=NOCH$_3$ | H | OCH$_2$ | CH$_3$ | H | CF$_3$ | H | m.p. = 135–139 |
| 204 | R'.4-•=NOCH$_3$ | H | OCH$_2$ | CH$_3$ | H | CF$_3$ | H | NMR = 2.71; 4.11; 5.33;<br>6.04; 6.84; 7.25–7.70; 8.75 |

*m.p. [° C.]; $^1$H-NMR [ppm]; IR [cm$^{-1}$]

Examples of the action against harmful fungi

It was possible to show the fungicidal action of the compounds of the general formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight Emulphor® EL (Emulan® EL, emulsifier based on ethoxylated fatty alcohols) and diluted with water according to the concentration desired.

Activity against *Puccinia recondita* (brown rust of wheat)

Leaves of wheat seedlings (Kanzler variety) were dusted with spores of brown rust (*Puccinia recondita*). The plants treated in this way were incubated for 24 h at 20–22° C. and a relative atmospheric humidity of 90–95% and then treated with the aqueous active compound preparation (application rate: 250 ppm). After a further 8 days at 20–22° C. and 65–70% relative atmospheric humidity, the extent of fungal development was determined. Assessment was carried out visually.

In this test, the plants treated with the compounds 2, 3, 7, 11, 12, 14, 17, 19, 21–23, 26, 30, 34–36, 39, 40, 43, 47, 49, 52, 53, 55, 57, 58 and 62 according to the invention showed an attack of 15% or less, while the untreated (control) plants were attacked to 70%.

In a corresponding test, the plants treated with 250 ppm of the compounds 64, 66, 68, 69, 72, 74, 78, 79, 81, 82, 83, 85, 86, 88, 89, 90, 92, 94, 96, 97, 98, 100, 101, 102, 103, 104, 105, 107, 108, 109, 110, 111, 113, 116, 118, 119, 120, 121, 125, 127, 131, 166, 167, 175, 176, 177, 178, 180, 190, 193, 194, 196, 198, 201, 202 and 204 showed an attack of 15% or less, while the untreated (control) plants were attacked to 70%.

Activity against *Pyricularia oryzae* (Rice blast)

Rice seedlings (variety: Tai Nong 67) were sprayed until dripping wet with the active compound preparation (application rate 63 ppm). After 24 hours, the plants were sprayed with an aqueous spore suspension of the fungus *Pyricularia oryzae* and kept 6 days at 22–24° C. at a relative atmospheric humidity of 95–99%. Assessment was carried out visually.

In this test, the plants treated with the compounds 2, 3, 6, 7, 11, 17, 21–23, 30, 35, 36, 40, 43, 47–49, 52, 53, 55–58 and 62 according to the invention showed an attack of 15% or less, while the untreated (control) plants were attacked to 65%.

In a corresponding test, the plants treated with 63 ppm of the compounds 66, 67, 71, 72, 73, 76, 77, 78, 79, 80, 81, 82, 86, 88, 89, 90, 91, 92, 94, 95, 96, 97, 98, 100, 101, 102, 103, 104, 105, 107, 109, 110, 111, 116, 118, 119, 125, 127, 129, 130, 131, 134, 135, 137, 139, 174, 175, 176 and 178 showed an attack of 15% or less, while the untreated (control) plants were attacked to 85%.

Examples of the action against animal pests

It was possible to show the action of the compounds of the general formula I against animal pests by the following tests:

The active compounds were prepared a. as a 0.1% strength solution in acetone or b. as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols)

and diluted with acetone in the case of a. or with water in the case of b. according to the desired concentration.

After conclusion of the tests, the lowest concentration at which the compounds still caused an 80–100% inhibition or mortality in comparison with untreated control tests was determined in each case (activity threshold or minimum concentration).

*Aphis fabae* (black bean aphid), contact action

Heavily infested dwarf beans (*Vicia faba*) were treated with the aqueous active compound preparation. After 24 h, the mortality rate was determined.

In this test, the compounds 25, 35, 141, 193, 196 and 197 showed activity thresholds of 400 ppm or less.

*Nephotettix cincticeps* (green rice leafhopper), contact action

Round filters were treated with the aqueous active compound preparation and then populated with 5 adult leafhoppers. After 24 h, the mortality was assessed.

In this test, the compounds 53, 83, 125, 141, 193, 196, 197 and 201 showed activity thresholds of 0.4 mg or less.

*Prodenia litura* (Egyptian cotton leaf worm), contact action

Filters treated with the aqueous active compound preparation were populated with 5 caterpillars. The first assessment was carried out after 4 h. If at least one caterpillar is still alive, a feed mixture is added. After 24 h, the mortality was assessed.

In this test, the compounds 45, 46, 55, 141, 196 and 197 showed activity thresholds of 0.4 mg or less.

*Heliothis virescens* (cotton budworm), contact/damage action

Tobacco plants of size about 10 cm were treated with the aqueous active compound preparation. After drying off, the plants were in each case populated with 10 larvae of the 3rd stage of development. After 48 h, mortality and damage prevention were assessed.

In this test, the compounds 55, 196 and 197 showed activity thresholds of 400 ppm or less.

*Tetranychus telarius* (common red spider mite), contact action

Heavily infested potted dwarf beans which had the second pair of adult leaves were treated with aqueous active compound preparation. After 5 days in a greenhouse, the result was determined by means of a binocular microscope.

In this test, the compounds 17, 25, 35, 46, 47, 49, 51, 51 [sic], 52, 54, 57, 63, 66, 79, 80, 82, 83, 84, 85, 86, 125, 127, 131, 141, 150, 151, 169, 173, 196, 197, 198, 199 and 201 showed activity thresholds of 400 ppm or less.

We claim:

1. A pyrazolo pyrimidine of the formula I

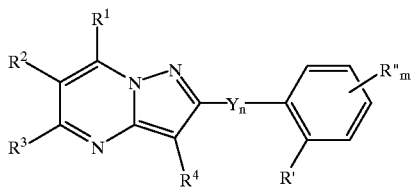

I n is 0 or 1;

Y is O, S, $NR^a$, $OCH_2*$, $SCH_2*$, $NR^aCH_2*$, $CH_2O*$, $CH_2S*$, $CH_2NR^{a*}$, $CH_2CH_2$, $CR^a{=}CR^b$ or $C{\equiv}C$, the positions identified by * marking the bond to the phenyl ring;

R' is $H_3CO$—CO—.=CHOCH$_3$, $H_3CNH$—CO—.=CHOCH$_3$, $H_3CO$—CO—.=NOCH$_3$, $H_3CNH$—CO—.=NOCH$_3$, $H_2N$—CO—.=NOCH$_3$, HO—CO—.=NOCH$_3$, $H_3CO$—CO—.=CHCH$_3$, $H_3CO$—CO—.=CHCH$_2$CH$_3$, $H_3C$—CO—.=CHOCH$_3$, $H_3C$—CO—.=NOCH$_3$, $H_3CCH_2$—CO—.=NOCH$_3$, the symbol ● and represent the carbon atom that is bonded to the phenyl ring;

N(OCH$_3$)—CO$_2$CH$_3$, N(CH$_3$)—CO$_2$CH$_3$, N(CH$_2$CH$_3$)—CO$_2$CH$_3$, or a group R'.1—.=NOCH$_3$, R'.2—.=NOCH$_3$, R'.3—.=NOCH$_3$ or R'.4—.=NOCH$_3$,

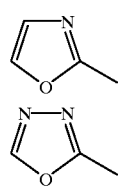

R'.1

R'.2

R'.3

R'.4

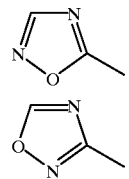

m is 0, 1, 2 or 3, where the radicals R" may be different if m is greater than 1;

R" is cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^1$ and $R^3$ are hydrogen, cyano, nitro, hydroxyl, amino, halogen, alkyl, haloalkyl, alkoxy, haloalkoxy, alkylthio, haloalkylthio, aryl, arylalkyl, aryloxy, arylalkoxy, arylthio, heteroaryl, heteroarylalkyl, heteroaryloxy, heteroarylalkoxy, heteroarylthio, or $NR^cR^d$, $NR^cNR^dR^e$, CO—$R^c$, CO—$NR^cR^d$, O—CO—$R^c$, O—CO$_2$—$R^c$, O—CO—$NR^cR^d$, $NR^c$—CO—$R^d$, $NR^c$—CO$_2$—$R^d$ or $NR^c$—CO—$NR^dR^e$;

$R^2$ is hydrogen, halogen, alkyl, haloalkyl, alkoxy, haloalkoxy, aryl, aryloxy, heteroaryl, heteroaryloxy, CO—$R^c$, CO$_2R^c$, or $CR^f{=}NOR^g$;

$R^4$ is hydrogen, cyano, nitro, nitroso, halogen, alkyl, haloalkyl, alkoxy, haloalkoxy, alkylthio, haloalkylthio, aryl, arylalkyl, aryloxy, arylalkoxy, arylthio, heteroaryl, heteroarylalkyl, heteroaryloxy, heteroarylalkoxy, heteroarylthio, or $NR^cR^d$, CO—$R^c$, CO$_2$—$R^c$ or $CR^f{=}NOR^g$;

$R^a$ and $R^b$ are hydrogen, halogen, $C_1$–$C_4$-alkyl or $C_1$–$C_4$-haloalkyl; p1 $R^c$, $R^d$ and $R^e$ are hydrogen, alkyl, alkenyl, alkynyl, aryl, arylalkyl, heteroaryl or heteroarylalkyl;

$R^f$ is hydrogen, cyano, halogen, optionally substituted alkyl, alkoxy, alkylthio, alkenyl, alkenyloxy, alkenylthio, alkynyl, alkynyloxy, alkynylthio, cycloalkyl, cycloalkoxy, cycloalkylthio, heterocyclyl, heterocyclyloxy, heterocyclylthio, aryl, aryloxy, arylthio, heteroaryl, heteroaryloxy or heteroarylthio;

$R^g$ is hydrogen, optionally substituted alkyl, alkenyl, alkynyl, cycloalkyl, heterocyclyl, aryl or heteroaryl.

2. A pyrazolo pyrimidine of the formula I as claimed in claim 1, where the substituents have the following meanings:

$R^1$ and $R^3$ are hydrogen, cyano, nitro, hydroxyl, amino, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, aryl, aryl-$C_1$–$C_4$-alkyl, aryloxy, aryl-$C_1$–$C_4$-alkoxy, arylthio, heteroaryl, heteroaryl-$C_1$–$C_4$-alkyl, heteroaryloxy, heteroaryl-$C_1$–$C_4$-alkoxy, heteroarylthio, or $NR^cR^d$, $NR^cNR^dR^e$, CO—$R^c$, CO—$NR^cR^d$, O—CO—$R^c$, O—CO$_2$—$R^c$, O—CO—$NR^cR^d$, $NR^c$—CO—$R^d$, $NR^c$—CO$_2$—$R^d$ or $NR^c$—CO—$NR^dR^e$;

$R_2$ is hydrogen, halogen, $C_1$–$C_6$-alkyl, $C_1$–$C_6$-haloalkyl, $C_1$–$C_6$-alkoxy, $C_1$–$C_6$-haloalkoxy, aryl, aryloxy, heteroaryl, heteroaryloxy, CO—$R^c$, CO$_2R^c$ or $CR^f{=}NOR^g$;

$R^4$ is hydrogen, cyano, nitro, nitroso, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, aryl, aryl-$C_1$–$C_4$-alkyl, aryloxy, aryl-$C_1$–$C_4$-alkoxy, arylthio, heteroaryl, heteroaryl-$C_1$–$C_4$-alkyl, heteroaryloxy, heteroaryl-$C_1$-$C_4$-alkoxy, heteroarylthio, or $NR^cR^d$, $CO-R^c$, $CO_2-R^c$ or $CR^f=NOR^g$;

$R^a$ and $R^b$ are hydrogen, halogen, $C_1$-$C_4$-alkyl or $C_1$-$C_4$-haloalkyl;

$R^c$, $R^d$ and $R^e$ are hydrogen, $C_1$-$C_6$-alkyl, $C_3$-$C_6$-alkenyl, $C_3$-$C_6$-alkynyl, aryl, aryl-$C_1$-$C_4$-alkyl, heteroaryl or heteroaryl-$C_1$-$C_4$-alkyl;

$R^f$ is hydrogen, cyano, halogen, $C_1$-$C_6$-alkyl, $C_1$-$C_6$-alkoxy, $C_1$-$C_6$-alkylthio, $C_3$-$C_6$-alkenyl, $C_3$-$C_6$-alkenyloxy, $C_3$-$C_6$-alkenylthio, $C_3$-$C_6$-alkynyl, $C_3$-$C_6$-alkynyloxy or $C_3$-$C_6$-alkynylthio, where these groups may be partially or completely halogenated and may carry one to three of the following radicals: cyano, nitro, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-cycloalkoxy, aryl, aryloxy, heteroaryl or heteroaryloxy, where the cyclic radicals in turn may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino and di-$C_1$-$C_4$-alkylamino; $C_3$-$C_6$-cycloalkyl, $C_3$-$C_6$-cycloalkoxy, $C_3$-$C_6$-cycloalkylthio, heterocyclyl, heterocyclyloxy, heterocyclylthio, aryl, aryloxy, arylthio, heteroaryl, heteroaryloxy or heteroarylthio, where these groups may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-cycloalkoxy, aryl, aryloxy, heteroaryl or heteroaryloxy, where the cyclic radicals in turn may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino and di-$C_1$-$C_4$-alkylamino;

$R^g$ is hydrogen, $C_1$-$C_{10}$-alkyl, $C_3$-$C_{10}$-alkenyl or $C_3$-$C_{10}$-alkynyl, where these groups may be partially or completely halogenated and may carry one to three of the following radicals: cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di-$C_1$-$C_4$-alkylamino, $C_1$-$C_4$-alkylcarbonyl, $C_1$-$C_4$-alkylcarbonyloxy, $C_1$-$C_4$-alkylcarbonylamino, $C_1$-$C_4$-alkoxycarbonyl, $C_1$-$C_4$-haloalkoxycarbonyl, $C_1$-$C_4$-alkylthiocarbonyl, $C_1$-$C_4$-haloalkylthiocarbonyl, $C_1$-$C_4$-alkylaminocarbonyl, di-$C_1$-$C_4$-alkylaminocarbonyl, $C_1$-$C_4$-alkoxycarbonyloxy, $C_1$-$C_4$-haloalkoxycarbonyloxy, $C_1$-$C_4$-alkylthiocarbonyloxy, $C_1$-$C_4$-haloalkylthiocarbonyloxy, $C_1$-$C_4$-alkylaminocarbonyloxy, di-$C_1$-$C_4$-alkylaminocarbonyloxy, $C_1$-$C_4$-alkoxycarbonylamino, $C_1$-$C_4$-haloalkoxycarbonylamino, $C_1$-$C_4$-alkylthiocarbonylamino, $C_1$-$C_4$-haloalkylthiocarbonylamino, $C_1$-$C_4$-alkylaminocarbonylamino, di-$C_1$-$C_4$-alkylaminocarbonylamino, $C_3$-$C_6$-cycloalkyl, $C_3$-$C_6$-cycloalkoxy, aryl, aryloxy, heteroaryl or heteroaryloxy, where the cyclic radicals in turn may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino and di-$C_1$-$C_4$-alkylamino; $C_3$-$C_6$-cycloalkyl, heterocyclyl, aryl or heteroaryl, where these groups may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino, di-$C_1$-$C_4$-alkylamino, $C_1$-$C_4$-alkylcarbonyl, $C_1$-$C_4$-alkylcarbonyloxy, $C_1$-$C_4$-alkylcarbonylamino, $C_1$-$C_4$-alkoxycarbonyl, $C_1$-$C_4$-haloalkoxycarbonyl, $C_1$-$C_4$-alkylthiocarbonyl, $C_1$-$C_4$-haloalkylthiocarbonyl, $C_1$-$C_4$-alkylaminocarbonyl, di-$C_1$-$C_4$-alkylaminocarbonyl, $C_1$-$C_4$-alkoxycarbonyloxy, $C_1$-$C_4$-haloalkoxycarbonyloxy, $C_1$-$C_4$-alkylthiocarbonyloxy, $C_1$-$C_4$-haloalkylthiocarbonyloxy, $C_1$-$C_4$-alkylaminocarbonyloxy, di-$C_1$-$C_4$-alkylaminocarbonyloxy, $C_1$-$C_4$-alkoxycarbonylamino, $C_1$-$C_4$-haloalkoxycarbonylamino, $C_1$-$C_4$-alkylthiocarbonylamino, $C_1$-$C_4$-haloalkylthiocarbonylamino, $C_1$-$C_4$-alkylaminocarbonylamino, di-$C_1$-$C_4$-alkylaminocarbonylamino, $C_3$-$C_6$-cycloalkyl, $C_3$-$C_6$-cycloalkoxy, aryl, aryloxy, heteroaryl or heteroaryloxy, where the cyclic radicals in turn may be partially or completely halogenated and may carry one to three of the following radicals: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylamino and di-$C_1$-$C_4$-alkylamino.

3. A process for preparing a compound of formula I as defined in claim 1, where $Y_n$ is $OCH_2^*$, $SCH_2^*$ or $NR^aCH_2^*$, which comprises reacting a benzyl derivative of the formula IIa

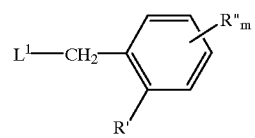

IIa where $L^1$ is a nucleophilically leaving group, in an inert organic solvent in the presence of a base with a pyrazolopyrimidine of the formula IIIa

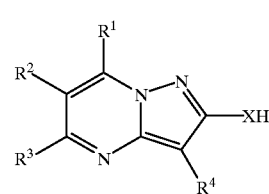

IIIa where X is O, S or $NR^a$.

4. A process for preparing a compound of formula I as defined in claim 1, where $Y_n$ is $C\equiv C$, which comprises reacting a phenylacetylene of the formula IIb

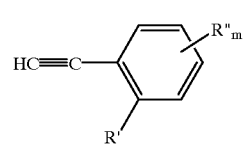

IIb in an inert solvent in the presence of a noble metal catalyst with a pyrazolopyrimidinyl halid of the formula IIIb

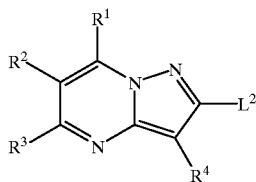

where $L^2$ is a halogen atom.

5. A process for preparing a compound of formula I as defined in claim 1, where $Y_n$ is $CH_2O^*$, $CH_2S^*$ or $CH_2NR^{a*}$, which comprises reacting a phenyl compound IIc

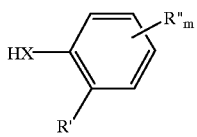

IIc where X is O, S or $NR^a$, in an inert solvent in the presence of a base with a pyrazolopyrimidinylmethylene halid of the formula IIIc

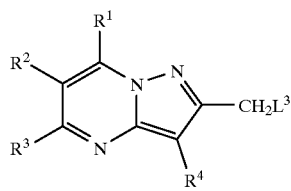

IIIc where $L^3$ is a nucleophilically replaceable leaving group.

6. A process for preparing a compound of formula I as defined in claim 1, where $Y_n$ is O, S or $NR^a$, which comprises coupling a phenyl compound of the formula IIc

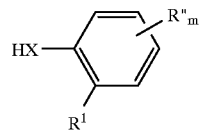

IIc where X is O, S or $NR^a$, in an inert solvent in the presence of a base with a pyrazolopyrimidinyl halid of the formula IIIb

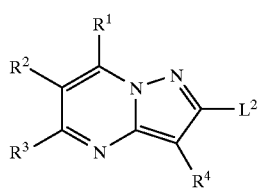

IIIb where $L^2$ is a halogen atom.

7. A process for preparing a compound of formula I as defined in claim 1, where $Y_n$ is $CR^a=CR^b$, which comprises converting a benzylphosphorous compound of the formula IId

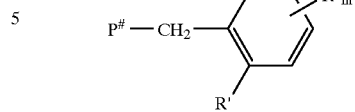

IId where $P^\#$ is a triarylphosphonium halide or dialkylphosphonate group, according to a wittig or Horner-Wittig reaction with a benzaldehyde of the formula IIId and

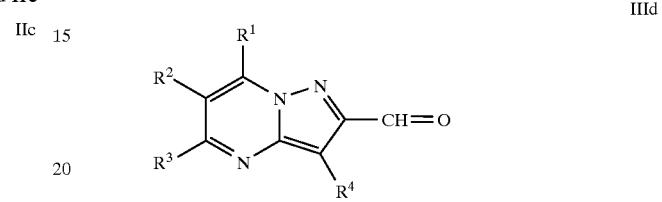

IIId into compound of formula I.

8. A process for preparing a compound of formula I as defined in claim 1, where $Y_n$ is $CR^a=CR^b$, which comprises converting a phosphorus compound IIIe

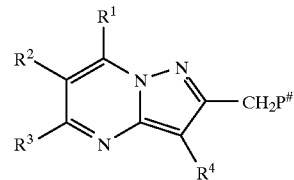

IIIe where $P^\#$ is a triarylphosphonium halide or dialkylphosphonate group, according to a wittig or Horner-Wittig reaction with a benzaldehyde of the formula IIe

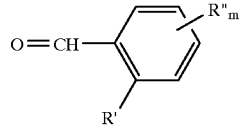

IIe into compound of formula I.

9. A composition suitable for controlling pests or harmful fungi, which comprises a solid or liquid carrier and an effective amount or a compound of the formula I as defined in claim 1.

10. A method of controlling harmful fungi, which comprises treating the fungi or the materials, plants, soil or seed to be protected from fungal attack with an effective amount of a compound of the formula I as defined in claim 1.

11. A method of controlling pests, which comprises treating the pests or the materials, plants, soil or seed to be protected from them with an effective amount of a compound of the formula I as defined in claim 1.

* * * * *

UNITED STATES PATENT AND TRADEMARK OFFICE
CERTIFICATE OF CORRECTION

PATENT NO.: 5,902,773

DATED: May 11, 1999

INVENTOR(S): BENOIT et al.

It is certified that error appears in the above-identified patent and that said Letters Patent is hereby corrected as shown below:

Col. 71, claim 1, line 30, after "pyrazolo" insert -- [1,5a]--.

Col. 72, claim 1, line 34, delete "p1".

Col. 72, claim 2, line 46, after "pyrazolo" insert -- [1,5a]--.

Col. 73, line 10, "$C_3-C^6-$" should be --$C_3-C_6$--.

Col. 73, line 16, "$C_3-C^6-$" should be --$C_3-C_6$--.

Signed and Sealed this

Sixteenth Day of November, 1999

Attest:

Q. TODD DICKINSON

*Attesting Officer*           *Acting Commissioner of Patents and Trademarks*